US012059230B2

(12) United States Patent
Strano et al.

(10) Patent No.: US 12,059,230 B2
(45) Date of Patent: Aug. 13, 2024

(54) EXTENDING FLUORESCENT ASSAYS IN VIVO FOR BIOMEDICAL SENSING: WAVELENGTH MODULATION SPECTROSCOPY

(71) Applicant: MASSACHUSETTS INSTITUTE OF TECHNOLOGY, Cambridge, MA (US)

(72) Inventors: Michael Strano, Lexington, MA (US); Volodymyr Koman, Cambridge, MA (US); Naveed Bakh, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 291 days.

(21) Appl. No.: 17/111,287

(22) Filed: Dec. 3, 2020

(65) Prior Publication Data

US 2021/0161386 A1    Jun. 3, 2021

Related U.S. Application Data

(60) Provisional application No. 62/943,169, filed on Dec. 3, 2019.

(51) Int. Cl.
*A61B 8/14* (2006.01)
*A61B 5/00* (2006.01)

(52) U.S. Cl.
CPC .......... *A61B 5/0071* (2013.01); *A61B 5/6847* (2013.01); *A61B 5/7203* (2013.01); *A61B 5/725* (2013.01); *A61B 5/4821* (2013.01); *A61B 2503/40* (2013.01); *A61B 2562/0285* (2013.01)

(58) Field of Classification Search
CPC ... A61B 5/0071; A61B 5/6847; A61B 5/7203; A61B 5/725; A61B 5/4821; A61B 2503/40; A61B 2562/0285; A61B 5/6852; A61B 5/7214

See application file for complete search history.

(56) References Cited

U.S. PATENT DOCUMENTS

| | | | |
|---|---|---|---|
| 2009/0130773 A1* | 5/2009 | Ayi | C12Q 1/6818 436/172 |
| 2009/0299228 A1* | 12/2009 | Lozier | A61F 2/36 606/92 |
| 2010/0065429 A1* | 3/2010 | Mount | G01N 33/582 204/547 |
| 2011/0250145 A1* | 10/2011 | Sharma | C12Q 1/28 424/9.6 |
| 2013/0035567 A1* | 2/2013 | Strano | G01N 33/54373 977/750 |
| 2014/0017700 A1* | 1/2014 | Fan | G01N 33/582 422/69 |
| 2016/0374556 A1* | 12/2016 | Colvin, Jr. | A61B 5/686 600/302 |
| 2017/0176338 A1* | 6/2017 | Wu | G02B 21/367 |
| 2017/0241765 A1* | 8/2017 | Adie | G01B 9/02002 |
| 2017/0370939 A1* | 12/2017 | Jones | G01N 21/6428 |

FOREIGN PATENT DOCUMENTS

WO  WO-2018090040 A1 *  5/2018  .......... A61B 5/0075

* cited by examiner

*Primary Examiner* — Joel F Brutus
(74) *Attorney, Agent, or Firm* — Honigman LLP

(57) ABSTRACT

A system and method of enhancing fluorescence assays can include signal modulation using an an excitation beam directed at a sensor having a modulation frequency and a detector configured to monitor emission from the sensor at a multiple of the modulation frequency.

31 Claims, 73 Drawing Sheets

(b)

(c)

EXTENDING FLUORESCENT ASSAYS IN VIVO FOR BIOMEDICAL SENSING: WAVELENGTH MODULATION SPECTROSCOPY

PRIORITY CLAIM

This application claims priority to U.S. Provisional Patent Application No. 62/943,169, filed Dec. 3, 2019, which is incorporated by reference in its entirety.

FIELD OF THE INVENTION

The invention relates to fluorescent assays and systems and methods of performing those assays.

BACKGROUND

Fluorescence-based assays are employed ubiquitously throughout the life sciences and medicine. However, their adaptation and translation to the in vivo environment is fundamentally hampered by unfavorable tissue scattering and intrinsic autofluorescence.

SUMMARY

In one aspect, a system for monitoring a sensor can include an excitation source directing a modulated excitation beam at a sensor, the modulated excitation beam having a modulation frequency, and a detector configured to monitor emission from the sensor, wherein the detector monitors emission at a multiple of the modulation frequency.

In another aspect, a method of detecting an emission from a sensor can include irradiating a sensor with a modulated excitation beam having a modulation frequency, and detecting an emission from the sensor, wherein the detector monitors emission at a multiple of the modulation frequency.

In certain circumstances, the modulated excitation beam can include three distinct excitation wavelengths. For example, the modulated excitation beam can include a first wavelength at or near a peak absorbance of the sensor and a second wavelength that is 20 nm to 60 nm shorter than the first wavelength. The modulated excitation beam can further include a third wavelength that is 20 nm to 60 nm longer than the first wavelength. The first wavelength can be at or near the peak absorbance and other wavelengths (for example, a second wavelength and a third wavelength) that are about 100 nm, 90 nm, 80 nm, 70 nm, 60 nm, 50 nm, 40 nm, 30 nm, 20 nm or 10 nm different from the first wavelength.

In certain circumstances, the modulation frequency can be less than 50 Hz, less than 40 Hz, less than 30 Hz, less than 20 Hz, less than 10 Hz, less than 5 Hz, less than 4 Hz, less than 3 Hz, less than 2 Hz, or less than 1 Hz. For example, the modulation frequency can be less than 0.5 Hz or less than 0.2 Hz.

In certain circumstances, the detector can evaluate a frequency that is 2, 3, 4, 5, 6, 7 or 8 times the modulation frequency.

In certain circumstances, the detector monitors emission at a wavelength greater than 1000 nm. The detector can be a band-pass filter.

In certain circumstances, the excitation source can be a continuum laser or a plurality of single wavelength lasers.

In certain circumstances, the sensor can include an emissive element. The emissive element can be a fluorescent dye, a semiconductor nanocrystal or a carbon nanotube.

In certain circumstances, the sensor can include a photoluminescent nanostructure embedded in a sensor hydrogel and an analyte-binding compound associated with the photoluminescent nanostructure. The analyte-binding compound can include a polymer.

In certain circumstances, the sensor can be in tissue. For example, the sensor can be more than 3 cm beneath a surface of the tissue, more than 4 cm beneath a surface of the tissue, or more than 5 cm beneath a surface of the tissue.

In certain circumstances, the method can improve a signal to noise ratio compared to a single excitation source by a factor of at least 10, at least 20, at least 30, at least 40 or at least 50.

Other aspects, embodiments, and features will be apparent from the following description, the drawings, and the claims.

BRIEF DESCRIPTION OF DRAWINGS

FIG. 1A is a photograph of an SKH1-E mouse under anesthesia with an implanted sensor (subcutaneous 5×5×2 mm$^3$ hydrogel) and an implanted catheter used to deliver analytes. FIG. 1B shows near-infrared images of subcutaneously implanted 5×5×2 mm$^3$ hydrogels: (i) sham (implant without a sensor), (ii) 0.1 cm deep sensor (hydrogel with 20 mg/l (AC)$_{15}$-SWNTs), and (iii) 1.5 cm deep sensor (the same implant as in (ii), but with a mouse flipped on the other side). Scale bars are 1 cm. FIG. 1C shows schematics of excitation light penetrating through a three-layered tissue to excite an implanted sensor. Tissue autofluorescence and laser reflection compete with the sensor emission.

FIG. 2A shows a graphical depiction of WIFF principle where the wavelength of excitation light is modulated at frequency f around a sensor absorption peak. FIG. 2B shows experimentally measured emission spectra (with 1100 nm long-pass filter) of the sensor (5×5×2 mm$^3$ gel with 10 mg/l (GT)$_{15}$-SWNTs) probed with three lasers used in WIFF excitation: 680 nm (red), 730 nm (black), and 780 nm (blue). FIG. 2C shows the same, as FIG. 2B, but for the background (5×5×2 cm$^3$ phantom tissue). The resulting intensity traces when the emission is collected by one channel detector for the sensor (FIG. 2D) and the background (FIG. 2E) demonstrate the emitted signal that oscillates at 2f, while the background emission—at f. The colors correspond to laser excitations as above. FIG. 2F shows a schematic of the experimental setup for 3-laser wavelength modulation. The excitation is programmed via a sequential opening of three mechanical shutters in front of the lasers, achieving a profile as in FIG. 2A. FIG. 2G shows fast Fourier transform (FFT) spectra extracted from FIG. 2D and FIG. 2E demonstrate that the signal and the background can be separated using WIFF. The intensity of 2f-component measured for different excitation peak wavelengths FIG. 2H and modulation widths FIG. 2I. Points refer to experimental measurements, while lines are the theoretical model.

FIG. 3A shows a photograph of a preserved fetal pig with a sensor (10×10×2 mm$^3$ hydrogel with 20 mg/l (AC)$_{15}$-SWNTs)) implanted into intraperitoneal space. A photograph is overlaid with a near-infrared image of the implanted sensor. The scale bar is 2.5 cm. FIG. 3B shows a cross-sectional view of the preserved fetal pig demonstrating intraperitoneal space where the sensor was implanted. The scale bar is 1 cm. FIG. 3C shows steps for WIFF: panel (i) Simultaneous tracking of f and 2f components of the signal upon the injection of 3 ml of 1 mM riboflavin at t=0 through the implanted catheter. Measurements were performed on a pig's side opposite to the sensor implantation, corresponding to 2.3 cm implantation depth; panel (ii) WIFF self-referencing reveals the response of the sensor, overlaid with the signal from the single laser excitation scheme; and panel (iii) WIFF data translated into actual riboflavin concentration as fitted to a model of analyte diffusing into the hydrogel. Similarly extracted hydrogen peroxide, $H_2O_2$ (FIG. 3D) and ascorbic acid, AA (FIG. 3E) concentrations for sensors ($10 \times 10 \times 2$ mm$^3$ hydrogel with 20 mg/l $(GT)_{15}$-SWNTs and $(ACCA)_7$-SWNTs, respectively) implanted at 3 cm depth in phantom tissue upon the addition of 100 μM analytes at 106 sec and 81 sec, respectively. The signal (FIG. 3F) and its SNR (FIG. 3G) for the sensor ($5 \times 5 \times 2$ mm$^3$ gel with 10 mg/l $(GT)_{15}$-SWNTs) implanted at various depths into the chicken breast tissue (n=5). The sensor signal was found as the difference between two measurements from a sample with and without a sensor. The single laser excitation was at 730 nm. WIFF system was modulated at 2 Hz between 680, 730, and 780 nm. The emission collection was at >1100 nm.

FIG. 4A shows excitation-emission map for a freshly-sacrificed SKH1-E mouse stomach. FIG. 4B shows a summary of autofluorescence intensity for various mice organs at 1.7 mW/cm$^2$ power of 730 nm excitation and infrared emission (>1100 nm). FIG. 4C shows an emission line extracted from (FIG. 4A) for 730 nm excitation. FIG. 4D shows estimated noise levels. FIG. 4E shows normalized absorption spectra of chlorophyll and ten fluorescent dyes. FIG. 4F shows normalized absorption (black) and emission (red) spectra for Alexa 700 dye. Dashed blue lines correspond to excitation lines and the yellow shaded region corresponds to the collection range. FIG. 4G shows signals of a sensor (2 μM of Alexa 700 in $5 \times 5 \times 2$ mm$^3$ chamber) implanted at various depth inside the phantom tissue (n=3). SNR values (FIG. 4H) and SNR improvement (FIG. 4I) when using WIFF over the single laser excitation scheme for various dyes implanted at 1 cm depth of phantom tissue.

FIG. 5A shows a photograph of an SKH1-E mouse with a sensor ($5 \times 5 \times 2$ mm$^3$ hydrogel with 20 mg/l $(AC)_{15}$-SWNTs) implanted subcutaneously near the stomach area, the respective near-infrared image, and single laser and WIFF measurements of the sensor signals (n=5). Scale bars are 5 mm. FIG. 5B shows sensitivity comparisons for the near-infrared images (grey), single laser (black), and WIFF (red) intensities (n=5) for sensors implanted as in FIG. 5A. Sham stands for gels without a sensor, flipped configuration represents a mouse laying on its back with the signal passing through the full thickness of the animal body. FIG. 5C shows: panel (i) a photograph of an SKH1-E mouse under anesthesia in the measurement setup with the implanted catheter (the scale bar is 1 cm); panels (ii) and (iii) near-infrared images of a mouse with a subcutaneously-implanted sensor ($5 \times 5 \times 2$ mm$^3$ hydrogel with 20 mg/l $(AC)_{15}$-SWNTs), demonstrating a change in intensity and sensor position before (ii) vs. after (iii) injection of 100 μl of saline. The scale bar is 5 mm. FIG. 5D shows normalized intensity profiles for single laser and WIFF excitations for the injection in (c) at t=0. FIG. 5E shows the respective WIFF 2f and f intensity components. Normalized intensity profiles for single laser and WIFF excitations (FIG. 5F) and extracted concentration (FIG. 5G) after an injection of 1 ml of riboflavin (300 μM) at t=0 through the catheter. FIG. 5H shows extracted riboflavin diffusivity. The single laser excitation was at 730 nm. WIFF system was modulated at 2 Hz between 680, 730, and 780 nm. The emission collection was at >1100 nm.

FIG. 6A shows the excitation wavelength is modulated in time with frequency f. FIG. 6B shows excitation lines are selected such that the median wavelength (green) corresponds to the absorption maximum of the sensor of interest, while the shortest (red) and the longest wavelengths (blue) fall symmetrically on two sides of the absorption peak. The intensity of the emission is proportional to the absorption. FIG. 6C shows, in contrast, the background absorption peak lies off the median excitation wavelength. Such excitation causes the fluorescent intensity of the sensor to oscillate at 2f (FIG. 6D), while the background intensity oscillates at f (FIG. 6E). The fluorescence peak positions affect only the intensity of the signal.

FIG. 8A shows sinusoidal (20%); FIG. 8B shows three-wavelength step-way (7%); FIG. 8C shows three-wavelength round-way (15%); FIG. 8D shows five-wavelength step-way (0.9%); FIG. 8E shows five-wavelength round-way (13%); and FIG. 8F shows five-wavelength round-way adapted to sinusoidal (14%).

FIG. 9A shows the intensity of signal 2f-component, FIG. 9B shows the intensity of background 2f-component, FIG. 9C shows SNR, and FIG. 9D shows SNR improvement as compared to single laser measurements. The calculations were performed for the background in the form of tissue autofluorescence from FIG. 4C. WIFF was performed around the central wavelength that coincides with the sensor absorption peak and 50 nm modulation width. The excitation linewidth was taken to be 5 nm. The extracted parameters were normalized to experimental values obtained for a sensor ($5 \times 5 \times 2$ mm$^3$ gel with 10 mg/l $(GT)_{15}$-SWNTs) implanted at 3 cm depth into the chicken breast tissue as in FIG. 3F. The noise levels for the signal and the background were estimated to both be 8 pW at 2 Hz oscillation frequency. SNR was calculated as the ratio between the sensor signal and noise contributions from both the background and the signal. The intensity decrease at high frequencies is associated with mechanical artefacts caused by shutter switching. SNR improvement was calculated when using WIFF over a single laser excitation scheme as in FIG. 3F.

FIG. 10A shows a comparison between a signal absorption lineshape and its fitting using sixth and fourteenth order Taylor expansion. FIG. 10B shows FFT amplitude intensity extracted numerically from the absorption lineshape and its comparison with an analytical expression containing terms up to $6^{th}$ and $14^{th}$ orders.

FIG. 13A shows the intensity of signal 2f-component, FIG. 13B shows the intensity of background 2f-component, FIG. 13C shows SNR, and FIG. 13D shows SNR improvement as compared to single laser measurements. The calculations were performed for the background in the form of tissue autofluorescence from FIG. 4C. WIFF was performed with a 50 nm modulation width. The excitation linewidth was taken to be 5 nm and the oscillating frequency was 2 Hz. The extracted parameters were normalized to experimental values obtained for a sensor ($5 \times 5 \times 2$ mm$^3$ gel with 10 mg/l $(GT)_{15}$-SWNTs) implanted at 3 cm depth into the chicken breast tissue as in FIG. 3F. The noise levels for the signal and the background were estimated to both be 8 pW for the central excitation at 730 nm. SNR was calculated as the ratio between the sensor signal and noise contributions from both the background and the signal. SNR improvement was calculated when using WIFF over a single laser excitation scheme as in FIG. 3F.

FIG. 14A shows the intensity of signal 2f-component, FIG. 14B shows the intensity of background 2f-component, FIG. 14C shows SNR, and FIG. 14D shows SNR improvement as compared to single laser measurements. The calculations were performed for the background in the form of tissue autofluorescence from FIG. 4C. WIFF was performed around the central wavelength that coincides with the sensor absorption peak. The excitation linewidth was taken to be 5 nm and the oscillating frequency was 2 Hz. The extracted parameters were normalized to experimental values obtained for a sensor ($5 \times 5 \times 2$ mm$^3$ gel with 10 mg/l $(GT)_{15}$-SWNTs) implanted at 3 cm depth into the chicken breast tissue as in FIG. 3F. The noise levels for the signal and the background were estimated to both be 8 pW for 50 nm modulation width. SNR was calculated as the ratio between the sensor signal and noise contributions from both the background and the signal. SNR improvement was calculated when using WIFF over a single laser excitation scheme as in FIG. 3F.

FIG. 15A shows the intensity of signal 2f-component, FIG. 15B shows the intensity of background 2f-component, FIG. 15C shows SNR, and FIG. 15D shows SNR improvement as compared to single laser measurements. The calculations were performed for the sensor with the background in the form of tissue autofluorescence from FIG. 4C. WIFF was performed around the central wavelength that coincides with the sensor absorption peak and 50 nm modulation width. The oscillating frequency was 2 Hz. The extracted parameters were normalized to experimental values obtained for a sensor ($5 \times 5 \times 2$ mm$^3$ gel with 10 mg/l $(GT)_{15}$-SWNTs) implanted at 3 cm depth into the chicken breast tissue as in FIG. 3F. The noise levels for the signal and the background were estimated to both be 8 pW for 5 nm excitation linewidth. SNR was calculated as the ratio between the sensor signal and noise contributions from both the background and the signal. SNR improvement was calculated when using WIFF over a single laser excitation scheme as in FIG. 3F.

FIG. 16A shows the intensity of signal 2f-component, FIG. 16B shows the intensity of background 2f-component, FIG. 16C shows SNR, and FIG. 16D shows SNR improvement as compared to single laser measurements. The calculations were performed for the background in the form of tissue autofluorescence from FIG. 4C. The sensor absorption peak was placed at a particular distance from the background absorption peak. WIFF was performed around the central wavelength that coincides with the sensor absorption peak and 50 nm modulation width. The excitation linewidth was taken to be 5 nm. The extracted parameters were normalized to experimental values obtained for a sensor ($5 \times 5 \times 2$ mm$^3$ gel with 10 mg/l $(GT)_{15}$-SWNTs) implanted at 3 cm depth into the chicken breast tissue as in FIG. 3F. For comparison, the sensor signal was assumed to be constant at various wavelengths (excluding light propagation in the tissue). The noise levels for the signal and the background were estimated to both be 8 pW for 70 nm distance between the background and the sensor absorption peaks. SNR was calculated as the ratio between the sensor signal and noise contributions from both the background and the signal. SNR improvement was calculated when using WIFF over a single laser excitation scheme as in FIG. 3F.

FIG. 18A shows normalized intensities for a single laser (black) and WIFF (red), corrected for the background signal. Five replicas on biologically independent animals. Sensors ($10 \times 10 \times 2$ mm$^3$ gel with 20 mg/l $(AC)_{15}$-SWNTs)) were implanted into the intraperitoneal space of preserved fetal pigs. Animals were monitored for 600 sec and then an injection of 3 ml of 1 mM riboflavin was performed through an implanted catheter. FIG. 18B shows extracted concentrations after analyte injections (red) and a fit to the diffusion model (dashed blue). The time t=0 corresponds to the time of injection.

FIG. 19A shows a calibration curve for nanosensors in solution. The red line represents a fit to the sigmoidal function to extract the parameters presented in Table 1. FIG. 19B shows a response comparison between control and analyte groups after t=600 sec post-injection. Sensors ($10 \times 10 \times 2$ mm$^3$ gel with 20 mg/l $(AC)_{15}$-SWNTs)) were implanted into the intraperitoneal space of preserved fetal pigs. An injection of 3 ml of saline for the control group and 3 ml of 1 mM riboflavin for the analyte group was performed through an implanted catheter.

FIG. 20A shows a calibration curve for nanosensors in solution. The red line represents a fit to the sigmoidal function to extract the parameters presented in Table 1. The normalized response of a sensor ($10 \times 10 \times 2$ mm$^3$ gel with 20 mg/l $(GT)_{15}$-SWNTs) implanted at 3 cm depth in phantom tissue upon the addition of 100 μM of hydrogen peroxide ($H_2O_2$) at: t=55 sec (FIG. 20B), t=98 sec (FIG. 20D), and t=106 sec (FIG. 20F) and the extracted $H_2O_2$ concentrations (FIG. 20C), (FIG. 20E), (FIG. 20G), respectively. For this, WIFF data were fitted to a diffusion model with diffusivity, proportionality constant, and dissociation constant, all as fit parameters. The extracted parameters, their uncertainties, and the calibration curve were used to calculate concentrations.

FIG. 21A shows a calibration curve for nanosensors in solution. The red line represents a fit to the sigmoidal function to extract the parameters presented in Table 1. The normalized response of a sensor (10×10×2 mm$^3$ gel with 20 mg/l (ACCA)$_7$-SWNTs) implanted at 3 cm depth in phantom tissue upon the addition of 100 µM of ascorbic acid (AA) at: t=81 sec (FIG. 21B), 1=37 sec (FIG. 21D), and t=84 sec (FIG. 21F) and the extracted AA concentrations (FIG. 21C), (FIG. 21E), (FIG. 21G), respectively. For this, WIFF data were fitted to a diffusion model with diffusivity, proportionality constant, and dissociation constant, all as fit parameters. The extracted parameters, their uncertainties, and the calibration curve were used to calculate AA concentrations.

FIG. 23 depicts signal detection from an implanted sensor. The signal from a sensor (5×5×10 mm$^3$ gel of 10 mg/l (GT)$_{15}$-SWNTs) implanted at various depth into a phantom tissue that mimics a mouse brain (top) and chicken tissue (bottom) (n=5). Monte Carlo simulations with tissue parameters as mouse brain (black line) match well experimental data points, underlying the absence of spurious reflections, and that the phantom tissue successfully mimics the targeted tissue. Light excitation 730 nm, emission collection >1100 nm. The detection is limited to 3 cm depth where the signal drops to 3× Noise level (dashed black). The shot noise from tissue autofluorescence (red) is considerably lower than that.

FIG. 26A shows signal RMS for different incident signals excited by a laser (1/500 sec integration time, no lock-in amplifier). The trend follows square root-dependence, allowing us to retrieve shot noise contribution of ~5 pW and read noise of ~40 pW. FIG. 26B shows lock-in amplifier RMS values for the signal modulated at different frequencies demonstrate 1/f dependence, corresponding to the electronic read-out noise behavior (1/500 sec integration time, 10 nW input signal produces 1 pW RMS shot noise). The red dashed line depicts read noise decreased to 4 pW. FIG. 26C shows integration time increases noise with the square root dependence. Since the signal grows proportionally to the integration time, this eventually improves SNR. The extracted noise contributions are: the read noise of 4 pW and shot noise of 5 pW at 0.002 sec and 111 pW at 1 sec integration. As the given photodetector does not allow the control of time integration, the latter results were obtained numerically by co-adding signal samples of the respective intervals.

FIGS. 27A-27J show normalized absorption (black) and emission (red) spectra for dyes. Dashed blue lines correspond to excitation lines and yellow shaded regions correspond to the collection regions. FIG. 27K shows a comparison between the chlorophyll absorption spectrum and dye absorption.

FIG. 28G shows an intensity time trace of TO-PRO-1 fluorescent signal when the excitation was modulated between three respective laser lines. FIG. 28H shows normalized intensity for a single laser (black) and WIFF (red) traces for 10 µM of TO-PRO-1 in a 5×5×2 mm$^3$ chamber implanted 1 cm deep inside the phantom tissue. At t=150 sec, 5 µl of NaOH (1 mM) was injected.

FIG. 29A shows representative bright-field and near-infrared images of implanted gels. Scale bars are 5 mm. Extracted values of cumulative (FIG. 29B) and peak intensities (FIG. 29C) (n=5, some points overlap). Sham stands for gels without carbon nanotubes, flipped represents a mouse laying on its back with the sensor signal passing through the full thickness of the animal body. The camera detects carbon nanotube signal when a gel is facing the camera but fails to do that in the case of a flipped mouse (asterisk denotes a two-tailed value, $p<0.01$, tilde—$p>0.01$).

FIG. 32A shows normalized intensities for a single laser (black) and WIFF (red), corrected for the background signal. Five replicas on biologically independent animals. Sensors ($10 \times 10 \times 2$ mm$^3$ gel with 20 mg/l $(AC)_{15}$-SWNTs)) were implanted into the intraperitoneal space of mice. Animals were monitored for 600 sec and then an injection of 1 ml of riboflavin (300 μM) was performed through an implanted catheter. FIG. 32B shows extracted concentrations after analyte injections (red) and a fit to the diffusion model (dashed blue). The time t=0 corresponds to the time of injection.

FIG. 34A shows a Monte Carlo simulations of the normalized light intensity traveling through phantom tissue for three excitation wavelengths. The intensity of 680 nm laser needs to be corrected by ~3× at 5 cm implantation. FIG. 34B shows a simulated ratio of 2f and f-components of a sensor as a function of the relative side laser intensity (680 nm) as compared to the central laser intensity (730 nm). The curve demonstrates that one can maximize the 2f/f ratio as feedback to tune the relative laser intensity to avoid the effect of unequal excitation power as in FIG. 34A.

DETAILED DESCRIPTION

Herein, a wavelength-induced frequency filtering (WIFF), or wavelength modulation spectroscopy (WMS), is described whereby the fluorescence excitation wavelength is modulated across the absorption cross-section of a target probe, allowing the emission signal to be separated from the autofluorescent background, increasing the desired signal relative to noise, and internally referencing it to protect against artefacts. For example, using highly scattering tissue phantoms, an SKH1-E mouse model, and other complex tissue types, WIFF significantly improves the in vivo signal to noise ratio (SNR) of fluorescent probes and sensors up to 52 fold for commonly employed chromophores in the visible spectrum. WIFF extends measurements to extremely deep implants up to 5.5±0.1 cm depth in chicken breast tissue when using probes excited at 730 nm and emitting between 1150 and 1300 nm. Near-infrared fluorescent carbon nanotube sensors for $H_2O_2$, riboflavin, and ascorbic acid are benchmarked in vivo with 2 Hz temporal resolution in real-time allowing new tissue permeability measurements of the intraperitoneal cavity at significantly extended tissue depths. These results based on WIFF open up new avenues of biomedical research by extending a large number of fluorescent sensing assays to previously inaccessible in vivo environments.

Figure 35:
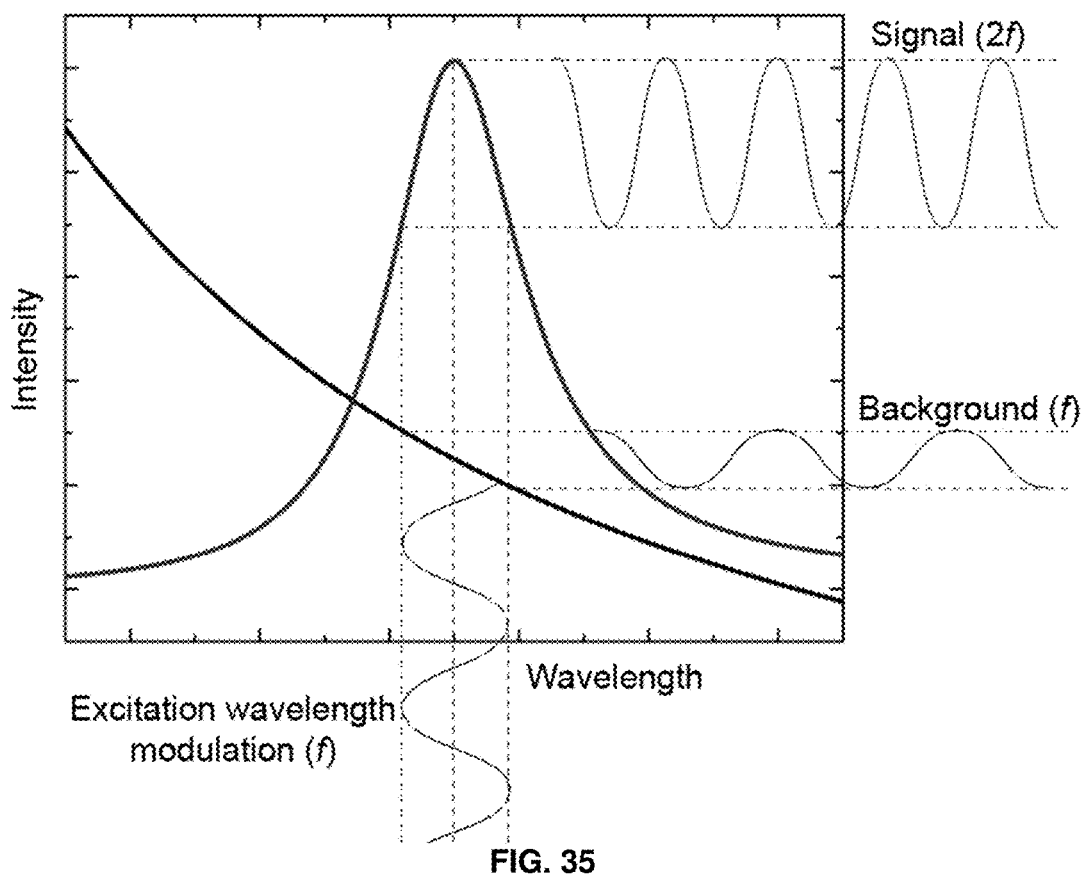
FIG. 35 depicts a schematic showing excitation with a modulated source and corresponding emissions at f and 2f.

Referring to FIG. 35, a schematic is shown, which depicts a method of providing excitation with a modulated source and corresponding emissions of a background and signal at a first frequency, f, and at a second frequency, 2f, respectively. The second frequency can be twice the first frequency. In certain embodiments, the second frequency can be 3, 4, 5, 6, 7 or 8 times the first frequency. The source excites an emissive element in a sample, for example, a sensor. The emissive element emits an emission wavelength in response to the excitation wavelength. The modulated source can have two, three, four, or more excitation wavelengths, which can be selected to be within 100 nm of a peak absorption wavelength for the emissive element. The excitation wavelengths can be selected to include a first wavelength at or near the peak absorbance and other wavelengths (for example, a second wavelength and a third wavelength) that are about 100 nm, 90 nm, 80 nm, 70 nm, 60 nm, 50 nm, 40 nm, 30 nm, 20 nm or 10 nm different from the first wavelength. The modulated source can provide the excitation wavelengths as a frequency modulated combination, modulating between the excitation wavelengths at low frequency, for example, less than 50 Hz, less than 40 Hz, less than 30 Hz, less than 20 Hz, less than 10 Hz, less than 5 Hz, less than 4 Hz, less than 3 Hz, less than 2 Hz, or less than 1 Hz. Emission can be monitored and the emission can be evaluated by fast Fourier transform of the emission signal and background. In the context of in vivo monitoring, the emission wavelength can be greater than 800 nm, for example, greater than 900 nm, greater than 1000 nm, greater than 1100 nm or greater than 1200 nm. The emission wavelength can be a near infrared wavelength. The evaluated emission at the second frequency can have an enhanced signal to noise ratio, allowing the method to detect a signal in a high noise environment, for example, in an in vivo environment through tissue that can otherwise make it difficult to directly monitor the emission intensity.

Figure 36A:
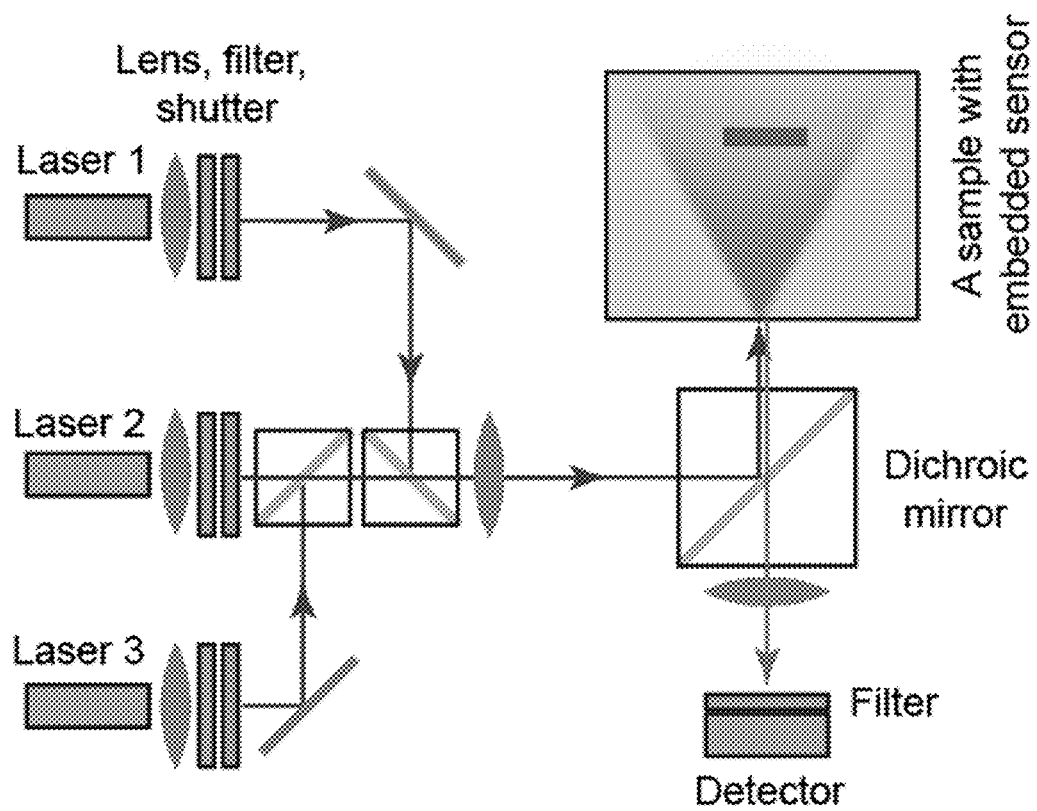
FIG. 36A-36B depict systems for enhanced fluorescent assay.
Figure 36B:
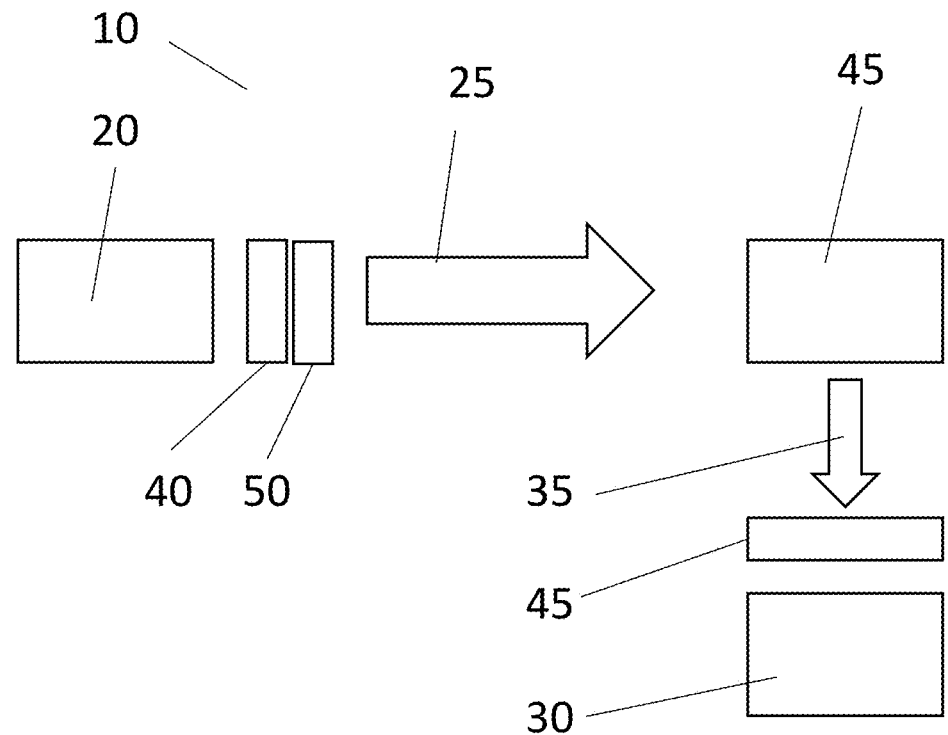

Referring to FIGS. 36A-36B, a system for fluorescent sensing assay can include a modulated excitation source and a detector. The modulated excitation source can be directed at a sample including a sensor, which can contain an emissive element. As specifically shown in FIG. 36A, for example, three lasers can provide the excitation wavelengths, which can be selected as described above. The excitation wavelengths can be modulated with shutters prior to interacting with the sample. The shutters can be controlled to provide a modulation pattern, examples of which are described below. A detector can be oriented to monitor an emission from the sensor, for example, the emissive element. The detector can employ a filter to improve monitoring of the emission wavelength.

FIG. 36B shows a system 10, which includes a modulated excitation source 20, a detector 30 and a sample holder 40. Source 20 is oriented to supply modulated excitation beam 25 to a sample in holder 40. Detector 30 is oriented to monitor an emission 35 from the sample in holder 40. Modulated excitation beam 25 can be generated by using optional combinations of one or more filters 45 and shutters 50 and mirrors (not shown). The source 20 can be a laser, for example, a continuum laser which can provide multiple wavelengths of light from a single source, or a plurality of lasers, for example, two, three, four or five lasers. The detector 30 can receive emission 35 through an optional filter 45.

Figure 37:
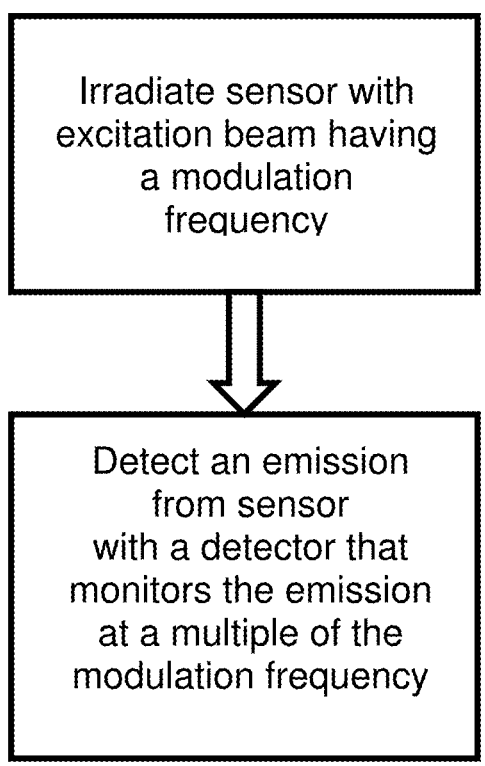
FIG. 37 depicts a method of detecting an emission from a sensor.

FIG. 37 depicts a method of detecting an emission from a sensor including irradiating a sensor with a modulated excitation beam having a modulation frequency, and detecting an emission from the sensor, wherein the detector monitors emission at a multiple of the modulation frequency.

The excitation wavelengths can be selected to include a first wavelength at or near the peak absorbance and other wavelengths (for example, a second wavelength and a third wavelength) that are about 100 nm, 90 nm, 80 nm, 70 nm, 60 nm, 50 nm, 40 nm, 30 nm, 20 nm or 10 nm different from the first wavelength.

The emission wavelength can be 800 nm, for example, greater than 900 nm, greater than 1000 nm, greater than 1100 nm or greater than 1200 nm. The emission wavelength can be at least 50 nm, at least 100 nm, at least 200 nm, or at least 300 nm longer than the excitation wavelengths.

A filter can be a band-pass filter or a tunable filter. A filter at the detector can be a band-pass filter, for example, allowing wavelengths longer than 1000 nm to pass to the detector.

The modulation frequency can be less than 50 Hz, less than 40 Hz, less than 30 Hz, less than 20 Hz, less than 10 Hz, less than 5 Hz, less than 4 Hz, less than 3 Hz, less than 2 Hz, less than 1 Hz, less than 0.5 Hz, or less than 0.2 Hz. The detector can evaluate the intensity of the emission wavelength at a multiple of the modulation frequency. The emission intensity can indicate concentration of analyte.

The system and method can improve the signal to noise ratio compared to a single excitation source by a factor of at least 10, at least 20, at least 30, at least 40 or at least 50. As a result, emissive elements can be detected in high noise environments, such as tissue, more readily, with higher accuracy.

Biological assays based on fluorescence sensing have had a tremendous impact on the life sciences and clinical research. See, for example, A. T. Aron, K. M. Ramos-Torres, J. A. Cotruvo, C. J. Chang, Recognition- and Reactivity-Based Fluorescent Probes for Studying Transition Metal Signaling in Living Systems, Accounts of Chemical Research 48 (2015) 2434-2442; V. S. Lin, W. Chen, M. Xian, C. J. Chang, Chemical probes for molecular imaging and detection of hydrogen sulfide and reactive sulfur species in biological systems, Chemical Society Reviews 44 (2015) 4596-4618; and J. J. A. Cotruvo, A. T. Aron, K. M. Ramos-Torres, C. J. Chang, Synthetic fluorescent probes for studying copper in biological systems, Chemical Society Reviews 44 (2015) 4400-4414, each of which is incorporated by reference in its entirety. High throughput screening using fluorescent sensors and probes has enabled preclinical evaluation and clinical trials of drug efficacy, biodistribution, and pharmacokinetics. Fluorescent sensors are routinely used to aid the diagnoses of arthritis, viral infections, cardiovascular, and inflammatory diseases, as well as cancer and metastasis. See, for example, K. A. Giuliano, D. L. Taylor, Fluorescent-protein biosensors: New tools for drug discovery, Trends in Biotechnology 16 (1998) 135-140; M. Wolff, J. Wiedenmann, G. U. Nienhaus, M. Valler, R. Heilker, Novel fluorescent proteins for high-content screening, Drug Discovery Today 11 (2006) 1054-1060; K. Bera, A. Kamajaya, A. V. Shivange, A. K. Muthusamy, A. L. Nichols, P. M. Borden, S. Grant, J. Jeon, E. Lin, I. Bishara, T. M. Chin, B. N. Cohen, C. H. Kim, E. K. Unger, L. Tian, J. S. Marvin, L. L. Looger, H. A. Lester, Biosensors Show the Pharmacokinetics of S-Ketamine in the Endoplasmic Reticulum, Frontiers in Cellular Neuroscience 13 (2019); W.-T. Chen, U. Mahmood, R. Weissleder, C.-H. Tung, Arthritis imaging using a near-infrared fluorescence folate-targeted probe, Arthritis Res Ther 7 (2005) R310; D. Xie, Fluorescent dye labeled influenza virus mainly infects innate immune cells and activated lymphocytes and can be used in cell-mediated immune response assay, Journal of Immunological Methods 343 (2009) 42-48; J. C. Cruz Hernández, O. Bracko, C. J. Kersbergen, V. Muse, M. Haft-Javaherian, M. Berg, L. Park, L. K. Vinarcsik, I. Ivasyk, D. A. Rivera, Y. Kang, M. Cortes-Canteli, M. Peyrounette, V. Doyeux, A. Smith, J. Zhou, G. Otte, J. D. Beverly, E. Davenport, Y. Davit, C. P. Lin, S. Strickland, C. Iadecola, S. Lorthois, N. Nishimura, C. B. Schaffer, Neutrophil adhesion in brain capillaries reduces cortical blood flow and impairs memory function in Alzheimer's disease mouse models, Nature Neuroscience 22 (2019) 413-420; M. H. Lee, H. M. Jeon, J. H. Han, N. Park, C. Kang, J. L. Sessler, J. S. Kim, Toward a Chemical Marker for Inflammatory Disease: A Fluorescent Probe for Membrane-Localized Thioredoxin, Journal of the American Chemical Society 136 (2014) 8430-8437; K. Midde, N. Sun, C. Rohena, L. Joosen, H. Dhillon, P. Ghosh, Single-Cell Imaging of Metastatic Potential of Cancer Cells, iScience 10 (2018) 53-65; and P. Mehrotra, Biosensors and their applications—A review, Journal of Oral Biology and Craniofacial Research 6 (2016) 153-159, each of which is incorporated by reference in its entirety. Such probes are also considered potent tools for early detection of biomarkers, for providing kinetic information on disease progression and response to therapeutics. See, for example, A. Sieron, K. Sieron-Stoltny, A. Kawczyk-Krupka, W. Latos, S. Kwiatek, D. Straszak, A. M. Bugaj, The role of fluorescence diagnosis in clinical practice, Onco Targets Ther 6 (2013) 977-982; and G. Emanuel, J. R. Moffitt, X. Zhuang, High-throughput, image-based screening of pooled genetic-variant libraries, Nature Methods 14 (2017) 1159-1162, each of which is incorporated by reference in its entirety. However, the vast majority are performed either in vitro or, in some instances, with sensors implanted in superficial tissue layers of a few mm depth. The latter include FDA-approved glucose sensors nominally implanted in adipose tissue. See, for example, M. Mortellaro, A. DeHennis, Performance characterization of an abiotic and fluorescent-based continuous glucose monitoring system in patients with type 1 diabetes, Biosensors and Bioelectronics 61 (2014) 227-231; and A. E. Colvin, H. Jiang, Increased in vivo stability and functional lifetime of an implantable glucose sensor through platinum catalysis, Journal of Biomedical Materials Research Part A 101A (2013) 1274-1282, each of which is incorporated by reference in its entirety. Potentially translating the large number of florescent assays used in the life sciences to animal and human in vivo studies requires significantly deeper sensor implantation, motivating the need for novel photonic or spectroscopic solutions. In this work, a Wavelength-Induced Frequency Filtering (WIFF) is developed as a technique to detect optical emission from fluorescent sensors embedded deeply within strongly scattering tissue. WIFF modulates the fluorescence excitation wavelength across the absorption cross section of the probe to separate the autofluorescent background, increase the signal to noise ratio (SNR), and drastically reduce noise levels. These aims and applications are distinct from the problem of improved spatial resolution in bioimaging, where, among others, Hong et al., Ghosh et al., and Bruns et al. have achieved significant progress. See, for example, M. Koch, P. Symvoulidis, V. Ntziachristos, Tackling standardization in fluorescence molecular imaging, Nature Photonics 12 (2018) 505-515; G. Hong, J. C. Lee, J. T. Robinson, U. Raaz, L. Xie, N. F. Huang, J. P. Cooke, H. Dai, Multifunctional in vivo vascular imaging using near-infrared II fluorescence, Nature Medicine 18 (2012) 1841; D. Ghosh, A. F. Bagley, Y. J. Na, M. J. Birrer, S. N. Bhatia, A. M. Belcher, Deep, noninvasive imaging and surgical guidance of submillimeter tumors using targeted M13-stabilized single-walled carbon nanotubes, Proceedings of the National Academy of Sciences 111 (2014) 13948-13953; and O. T. Bruns, T. S. Bischof, D. K. Harris, D. Franke, Y. Shi, L. Riedemann, A. Bartelt, F. B. Jaworski, J. A. Carr, C. J. Rowlands, M. W. B. Wilson, O. Chen, H. Wei, G. W. Hwang, D. M. Montana, I. Coropceanu, O. B. Achorn, J. Kloepper, J. Heeren, P. T. C. So, D. Fukumura, K. F. Jensen, R. K. Jain, M. G. Bawendi, Next-generation in vivo optical imaging with short-wave infrared quantum dots, Nature Biomedical Engineering 1 (2017) 0056, each of which is incorporated by reference in its entirety.

Several recent studies have improved signal to noise for in vivo sensing using a variety of hardware and material science approaches. Wang et al. demonstrated gastric pH sensing in the stomach of ICR mice using molecular fluorophores with penetration depth up to 4 mm and 84 μm spatial resolution. See, for example, S. Wang, Y. Fan, D. Li, C. Sun, Z. Lei, L. Lu, T. Wang, F. Zhang, Anti-quenching NIR-II molecular fluorophores for in vivo high-contrast imaging and pH sensing, Nature Communications 10 (2019) 1058, which is incorporated by reference in its entirety. As the implantation depth increases, spatial information is scrambled and the total signal attenuates. To maximize SNR, Zheng et al. assessed only the cumulative signal intensity when measuring pH levels and oxygen contents using polymer-iridium probes in the mammary glands of nude mice. See, for example, X. Zheng, H. Mao, D. Huo, W. Wu, B. Liu, X. Jiang, Successively activatable ultrasensitive probe for imaging tumour acidity and hypoxia, Nature Biomedical Engineering 1 (2017) 0057, each of which is incorporated by reference in its entirety. Several studies explored the limits of deep implantation, led by Chen et al. with 3.2 cm depth in pig tissue achieved using $NaYbF_4$ upconversion nanoparticles. See, for example, H. Yi, D. Ghosh, M.-H. Ham, J. Qi, P. W. Barone, M. S. Strano, A. M. Belcher, M13 Phage-Functionalized Single-Walled Carbon Nanotubes As Nanoprobes for Second Near-Infrared Window Fluorescence Imaging of Targeted Tumors, Nano Letters 12 (2012) 1176-1183; J. Yang, Y. Hu, J. Tan, L. Jia, Y.-H. Zhu, J.-S. Yu, Ultra-bright near-infrared-emitting HgS/ZnS core/shell nanocrystals for in vitro and in vivo imaging, Journal of Materials Chemistry B 3 (2015) 6928-6938; and G. Chen, J. Shen, T. Y. Ohulchanskyy, N. J. Patel, A. Kutikov, Z. Li, J. Song, R. K. Pandey, H. Ågren, P. N. Prasad, G. Han, ($\alpha$-NaYbF4:Tm3+)/CaF2 Core/Shell Nanoparticles with Efficient Near-Infrared to Near-Infrared Upconversion for High-Contrast Deep Tissue Bioimaging, ACS Nano 6 (2012) 8280-8287, each of which is incorporated by reference in its entirety. However, these results focused on spatially local-izing the probe, and not low noise temporal signal transmission as one needs for optical sensing at extreme depths. Iverson et al. used carbon nanotubes to measure nitric oxide in mouse liver but worked either with extracted organs or optical windows for in situ measurements to circumvent the limitations associated with thick tissue. See, for example, N. M. Iverson, P. W. Barone, M. Shandell, L. J. Trudel, S. Sen, F. Sen, V. Ivanov, E. Atolia, E. Farias, T. P. McNicholas, N. Reuel, N. M. A. Parry, G. N. Wogan, M. S. Strano, In vivo biosensing via tissue-localizable near-infrared-fluorescent single-walled carbon nanotubes, Nature Nanotechnology 8 (2013) 873, which is incorporated by reference in its entirety. Similarly, Bec et al. employed a fiber optic sensor to detect morphological and biochemical species within the coronary arteries of swine, to solve the problem of optical transmission through the tissue itself. See, for example, J. Bec, J. E. Phipps, D. Gorpas, D. Ma, H. Fatakdawala, K. B. Margulies, J. A. Southard, L. Marcu, In vivo label-free structural and biochemical imaging of coronary arteries using an integrated ultrasound and multispectral fluorescence lifetime catheter system, Scientific Reports 7 (2017) 8960, which is incorporated by reference in its entirety.

Several works have investigated the performance of implanted optical sensors in vivo. Del Rosal et al. found that tissue autofluorescence limits signal detection from an implanted sensor by lowering its SNR in five different mouse strains. See, for example, B. del Rosal, I. Villa, D. Jaque, F. Sanz-Rodríguez, In vivo autofluorescence in the biological windows: the role of pigmentation, Journal of Biophotonics 9 (2016) 1059-1067, which is incorporated by reference in its entirety. Neumann et al. proposed photo-bleaching techniques to temporally eliminate the contribution of autofluorescence, but this necessarily affects the underlying tissue. Muller et al. and Rao et al. utilized excitation-emission maps and synchronous spectra, respectively, to spectrally deconvolute autofluorescence, yet their collection remains time-consuming and hence prohibitive for most continuous sensing measurements. See, for example, M. Neumann, D. Gabel, Simple Method for Reduction of Autofluorescence in Fluorescence Microscopy, Journal of Histochemistry & Cytochemistry 50 (2002) 437-439; M. G. Müller, I. Georgakoudi, Q. Zhang, J. Wu, M. S. Feld, Intrinsic fluorescence spectroscopy in turbid media: disentangling effects of scattering and absorption, Applied Optics 40 (2001) 4633-4646; and C. M. Rao, Synchronous scan fluorescence spectroscopy of proteins and human eye lenses, Biochemical and Biophysical Research Communications 176 (1991) 1351-1357, each of which is incorporated by reference in its entirety. Collier et al. reviewed available lifetime techniques capable of filtering out autofluorescence either in the temporal or frequency domain. See, for example, B. B. Collier, M. J. McShane, Time-resolved measurements of luminescence, Journal of Luminescence 144 (2013) 180-190, which is incorporated by reference in its entirety. Among them, Fan et al. utilized lifetime measurements in the temporal domain to filter out autofluorescence to identify tumor subtypes up to 8 mm deep in living mice, while Medina-Rodriguez et al. used the multifrequency phase-modulation method to improve noise levels up to 13-fold on an example of conventional porphyrin sensor. See, for example, Y. Fan, P. Wang, Y. Lu, R. Wang, L. Zhou, X. Zheng, X. Li, J. A. Piper, F. Zhang, Lifetime-engineered NIR-II nanoparticles unlock multiplexed in vivo imaging, Nature Nanotechnology 13 (2018) 941-946; and S. Medina-Rodríguez, Á. de la Torre-Vega, F. J. Sainz-Gonzalo, M. Marín-Suárez, C. Elosúa, F. J. Arregui, I. R. Matias, J. F. Fernández-Sánchez, A. Fernández-Gutiér- rez, Improved Multifrequency Phase-Modulation Method That Uses Rectangular-Wave Signals to Increase Accuracy in Luminescence Spectroscopy, Analytical Chemistry 86 (2014) 5245-5256, each of which is incorporated by reference in its entirety. Nevertheless, challenges with pulse stability for prolonged measurements remain. See, for example, Time-Domain Lifetime Measurements, in: J. R. Lakowicz (Ed.), Principles of Fluorescence Spectroscopy, Springer US, Boston, MA, 2006, pp. 97-155, which is incorporated by reference in its entirety. Huang et al. highlighted that tissue movement from breathing, the circulatory system or other mechanical artefacts often distorts the optical signal and reviewed the proposed ratiometric solutions. See, for example, X. Huang, J. Song, B. C. Yung, X. Huang, Y. Xiong, X. Chen, Ratiometric optical nanoprobes enable accurate molecular detection and imaging, Chemical Society Reviews 47 (2018) 2873-2920, which is incorporated by reference in its entirety. However, ratiometric approaches require the development and integration of reference components. Jena et al. and Budhathoki-Uprety et al. used sensors based on wavelength-shift responses that are theoretically immune to intensity variations to detect endolysosomal lipids and microalbuminuria, respectively. See, for example, P. V. Jena, D. Roxbury, T. V. Galassi, L. Akkari, C. P. Horoszko, D. B. Iaea, J. Budhathoki-Uprety, N. Pipalia, A. S. Haka, J. D. Harvey, J. Mittal, F. R. Maxfield, J. A. Joyce, D. A. Heller, A Carbon Nanotube Optical Reporter Maps Endolysosomal Lipid Flux, ACS Nano 11 (2017) 10689-10703; and J. Budhathoki-Uprety, J. Shah, J. A. Korsen, A. E. Wayne, T. V. Galassi, J. R. Cohen, J. D. Harvey, P. V. Jena, L. V. Ramanathan, E. A. Jaimes, D. A. Heller, Synthetic molecular recognition nanosensor paint for microalbuminuria, Nature Communications 10 (2019) 3605, each of which is incorporated by reference in its entirety. However, the process of light dispersion over the required spectrometer grating necessarily decreases intensity, hindering signal detection in these wavelength-shift measurements. From these studies, it is clear that no technique to date simultaneously addresses the effects of tissue movement and autofluorescence. Finally, many researchers focus on boosting either excitation or collection efficiencies, fluorophore quantum yield, or work with probes in the near-infrared region, where absorption and scattering are significantly lower (see below). See, for example, G. Hong, A. L. Antaris, H. Dai, Near-infrared fluorophores for biomedical imaging, Nature Biomedical Engineering 1 (2017) 0010; and N. M. Iverson, G. Bisker, E. Farias, V. Ivanov, J. Ahn, G. N. Wogan, M. S. Strano, Quantitative Tissue Spectroscopy of Near Infrared Fluorescent Nanosensor Implants, J Biomed Nanotechnol 12 (2016) 1035-1047, each of which is incorporated by reference in its entirety. These efforts address the problem of signal attenuation, being complementary to tissue autofluorescence and movement that WIFF focuses on.

Herein, wavelength-induced frequency filtering (WIFF) is introduced to extend the application of ubiquitous fluorescent sensors in vivo for biomedical applications. WIFF modulates the fluorescence excitation wavelength across the absorption cross-section of the probe to separate the autofluorescent background, increase SNR, and reduce noise levels. This allows us to experimentally improve SNR by up to 52-fold and to recover signals even from a depth up to $5.5\pm0.1$ cm in chicken breast tissue using carbon nanotubes as a model fluorophore excited at 730 nm and emitting in 1150-1300 nm range. The advantages of WIFF are demonstrated for ten common fluorescent probes across several complex tissue types, including widely employed tissue phantoms, a fetal pig model of composite tissues, and live SKH1-E mice. A separated autofluorescence background was used as an internal reference, a feature valuable for successfully correcting for tissue movement. Such self-referencing enables WIFF to reliably track real-time sensor responses to riboflavin, ascorbic acid, and hydrogen peroxide from deep implants within the living SKH1-E mouse and preserved fetal pig—a milestone not heretofore demonstrated from any existing method in biomedical optics. Overall, WIFF enables real-time biochemical sensing from previously inaccessible, deep tissue locations, of considerable interest for fundamental biochemistry studies, therapeutics, and medical diagnostics.

A sensor can include an emissive structure, optionally embedded in a hydrogel. The emissive structure can be a photoluminescent dye, a semiconductor nanocrystal, or an emissive carbon nanotube. Some embodiments can be particularly advantageous due to the biocompatible nature of hydrogels. Hydrogels are particularly resistant to biological fouling. When sensors are used in vitro, biological entities (e.g., endothelial cells, proteins, etc.) may adhere to the sensor and block and/or consume the compound to be detected (e.g., glucose). When this occurs, the sensor may fail to detect the presence of the compound, or may detect a concentration of the compound that is lower than the amount in the surrounding fluid (e.g., blood), thus rendering the sensor inaccurate or unusable. Because hydrogels can be resistant to biological fouling, such disadvantages can be mitigated. In addition, in some embodiments where the hydrogels are not biodegradable, undesired leaching of nanostructures may be prevented.

As used herein, the term "hydrogel" is given its ordinary meaning in the art and refers to a material comprising a polymer network that is able to trap and contain water. The hydrogel may include polymer chains that are crosslinked, either directly or via a crosslinking agent. The degree of crosslinking may be varied, in some cases, to tailor the extent to which the gel absorbs or retains fluids. Examples of polymers capable of forming hydrogels include, but are not limited to, collagen, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups.

The hydrogel can be a porous structure. The pore sizes in the porous structure can be determined by factors including the concentration of polymers and crosslinks in the hydrogel. A hydrogel having a desired pore size or desired pore size distribution can be prepared by selecting the concentrations of monomers and crosslinkers present during polymerization to form a hydrogel. It can be advantageous for the hydrogel pores to be large enough to permit free access of analytes to components embedded in the hydrogel, e.g., to photoluminescent nanostructures. The pore size can be in the range of, for example, 10 nm to 1,000 nm, 20 nm to 500 nm, 50 nm to 250 nm, or 10 nm to 100 nm. When the analyte is a macromolecule (e.g., a protein, such as an immunoglobulin), a pore size greater than 10 nm, greater than 20 nm, greater than 30 nm, greater than 40 nm, greater than 50 nm, greater than 60 nm, greater than 70 nm, greater than 80 nm, greater than 90 nm, or 100 nm or greater can be desirable.

As used herein, the term "nanostructure" refers to articles having at least one cross-sectional dimension of less than about 1 µm, less than about 500 nm, less than about 250 nm, less than about 100 nm, less than about 75 nm, less than about 50 nm, less than about 25 nm, less than about 10 nm, or, in some cases, less than about 1 nm. Examples of nanostructures include nanotubes (e.g., carbon nanotubes), nanowires (e.g., carbon nanowires), graphene, and quantum dots, among others. In some embodiments, the nanostructures include a fused network of atomic rings.

A "photoluminescent nanostructure," as used herein, refers to a class of nanostructures that are capable of exhibiting photoluminescence. Examples of photoluminescent nanostructures include, but are not limited to, single-walled carbon nanotubes ("SWNT"), double-walled carbon nanotubes, semi-conductor quantum dots, semi-conductor nanowires, and graphene, among others. In some embodiments, photoluminescent nanostructures exhibit fluorescence. In some instances, photoluminescent nanostructures exhibit phosphorescence.

If the nanostructure is a carbon nanotube, the carbon nanotube can be classified by its chiral vector (n,m), which can indicate the orientation of the carbon hexagons. The orientation of carbon hexagons can affect interactions of the nanotube with other molecules, which in turn, can affect a property of the nanostructure.

A polymer can be associated with the nanostructure. The association can be a bond, for example, a covalent, ionic, van der Waals, dipolar or hydrogen bond. The association can be a physical association. For example, at least a portion of the nanostructure can be embedded in the polymer or a portion of the polymer can encompass the nanostructure.

A polymer can include a polypeptide, a polynucleotide or a polysaccharide. Examples of polysaccharides include dextran and chitosan. A polymer can include a plastic, for example, polystyrene, polyamide, polyvinyl chloride, polyethylene, polyester, polypropylene, polycarbonate, polyacrylamide or polyvinyl alcohol.

A polymer can be biocompatible, which can mean that the polymer is well tolerated by an organism. More specifically, biocompatibility can mean that a polymer does not elicit an immune response when it is brought in contact with an organism. It can also mean that a polymer can integrate into cell structures, cells, tissues or organs of an organism. The organism can be mammal, in particular, a human.

An exemplary polymer can exhibit minimal binding with other molecules. In certain circumstances, a polymer can have a protein adsorption of less than 5 $\mu g/cm^2$, less than 1 $\mu g/cm^2$, less than 0.5 $\mu g/cm^2$, less than 0.1 $\mu g/cm^2$, less than 0.05 $\mu g/cm^2$, or less than 0.01 $\mu g/cm^2$.

The association of a polymer with a nanostructure can change a property of the nanostructure. The property can be conductivity, polarity, or resonance. The property can be photoluminescence, including fluorescence or phosphorescence. More specifically, the property can be fluorescence with a wavelength in the near infrared spectrum. The property can be an emission wavelength, an emission intensity, a conductance, an electromagnetic absorbance or an emittance.

A polymer can be configured to interact with an analyte-binding compound. The analyte-binding compound undergoes a specific and typically reversible binding with an analyte. One class of suitable analyte binding compounds are polymers or proteins.

The polymer of the sensor can include protein, a polypeptide, a peptide, an oligonucleotide or a polynucleotide. In another embodiment, the polymer can include polyvinyl alcohol, poly(acrylic acid), poly(ethylene oxide), poly(vinyl pyrrolidinone), poly(allyl amine), poly(2-vinylpyridine), or poly(maleic acid).

The interaction of an analyte with a polymer that is interacting with a linker associated with a nanostructure can change a property of the nanostructure. The property can be conductivity, polarity, or resonance. The property can be photoluminescence, including fluorescence or phosphorescence. More specifically, the property can be a fluorescent emission within the near infrared spectrum. The property can be an emission wavelength, an emission intensity, a conductance, an electromagnetic absorbance or an emittance.

The interaction of an analyte with a polymer can be reversible, meaning that the analyte can bind to the polymer and then release and be free of binding. The change in a property of the nanostructure due to the interaction of an analyte with a polymer can also be reversible. For example, the property of a nanostructure can have a first value, the analyte can bind to the polymer and alter the property to a second value, then the analyte can release from the polymer and the property can return to the first value.

The analyte can be a small molecule, protein, biomolecule, drug, biologic, or a metabolite thereof. For example, the analyte can be a monosaccharide, a polysaccharide, an amino acid, peptide, polypeptide, protein, a nucleotide, an oligonucleotide, a lipid, a polylipid, or a combination thereof.

A method of detecting protein binding can include determining the presence of an analyte in the sample based on the monitored property. Determining the presence of an analyte can include evaluating when the analyte is absent. In some embodiments, determining the presence of an analyte can include determining the concentration of the analyte, determining the purity of the analyte or determining the quantity of the analyte. In some embodiments, relatively low concentrations or quantities of an analyte can be determined. The ability to determine low concentrations of an analyte may be useful, for example, in detecting trace pollutants or trace amounts of toxins within a subject. In some embodiments, analyte concentrations of less than about 100 micromolar, less than about 10 micromolar, less than about 1 micromolar, less than about 100 nanomolar, less than about 10 nanomolar, or less than about 1 nanomolar can be determined. The quantity of the analyte that can be determined can be less than 1 mole, less than 1 millimole, less than 1 micromole, less than 1 nanomole, less than 1 picomole, less than 1 femtomole, less than 1 attomole or less than 1 zeptomole. In some cases, a single molecule of an analyte can be determined. The purity of the analyte can be greater than 25% pure, greater than 50%, greater than 75% pure, greater than 80%, greater than 85% pure, greater than 90% pure, greater than 95% pure, greater than 99% pure or greater than 99.9% pure.

A sensor complex can be imbedded in a hydrogel. Some embodiments can be particularly advantageous due to the biocompatible nature of hydrogels. Hydrogels are particularly resistant to biological fouling. When sensors are used in vitro, biological entities (e.g., endothelial cells, proteins, etc.) may adhere to the sensor and block and/or consume the compound to be detected (e.g., glucose). When this occurs, the sensor may fail to detect the presence of the compound, or may detect a concentration of the compound that is lower than the amount in the surrounding fluid (e.g., blood), thus rendering the sensor inaccurate or unusable. Because hydrogels can be resistant to biological fouling, such disadvantages can be mitigated. In addition, in some embodiments where the hydrogels are not biodegradable, undesired leaching of nanostructures may be prevented.

As used herein, the term "hydrogel" is given its ordinary meaning in the art and refers to a material including a polymer network that is able to trap and contain water. The hydrogel may include polymer chains that are crosslinked, either directly or via a crosslinking agent. The degree of crosslinking may be varied, in some cases, to tailor the extent to which the gel absorbs or retains fluids. Examples of polymers capable of forming hydrogels include, but are not limited to, collagen, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups. A hydrogel can be an alginate hydrogel.

The hydrogel can be a porous structure. The pore sizes in the porous structure can be determined by factors including the concentration of polymers and crosslinks in the hydrogel. A hydrogel having a desired pore size or desired pore size distribution can be prepared by selecting the concentrations of monomers and crosslinkers present during polymerization to form a hydrogel. It can be advantageous for the hydrogel pores to be large enough to permit free access of analytes to components embedded in the hydrogel, e.g., to photoluminescent nanostructures. The pore size can be in the range of, for example, 10 nm to 1,000 nm, 20 nm to 500 nm, 50 nm to 250 nm, or 10 nm to 100 nm. When the analyte is a macromolecule (e.g., a protein, such as an immunoglobulin), a pore size greater than 10 nm, greater than 20 nm, greater than 30 nm, greater than 40 nm, greater than 50 nm, greater than 60 nm, greater than 70 nm, greater than 80 nm, greater than 90 nm, or 100 nm or greater can be desirable.

PEG hydrogels are widely used due to their variability and ease of use, allowing for the equal distribution of functional groups and a large degree of flexibility.

A sensor array can include a plurality of analysis regions on a support. A support can be glass or plastic. An analysis region can be a divot, a tube, a tray, a well, or a similar compartment for suitable for containing a liquid sample. In some cases, an analysis region can include a droplet or spot on the surface of a support (e.g., a flat support). In those cases, an analysis region can be formed by spotting the composition on a support. A plurality of analysis regions can be arranged in a pattern on a support. A pattern can include concentric circles, a spiral, a row, a column or a grid.

In some embodiments, the plurality of analysis regions can include two or more subsets of analysis regions. For example, a first subset of analysis regions can differ from a second subset of analysis regions by including a different nanostructure, a different linker, a different binding partner, a different polymer, a different analyte or a different sample. Additionally, a first subset of analysis regions can differ from a second subset of analysis regions by including a different environmental factor including a buffer, a reagent, a nutrient, a serum, an exposure to light, an oxygen concentration, a temperature or a pH.

Separation of Signal and Background Using WIFF

Figure 1A:
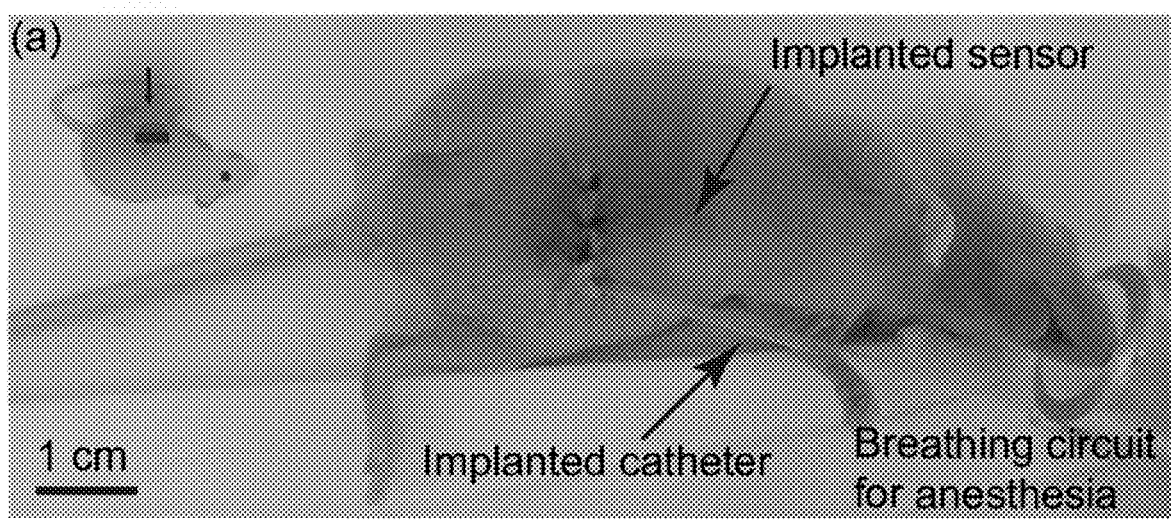
FIGS. 1A-1C depict challenges for deep-tissue sensing.
Figure 1B:
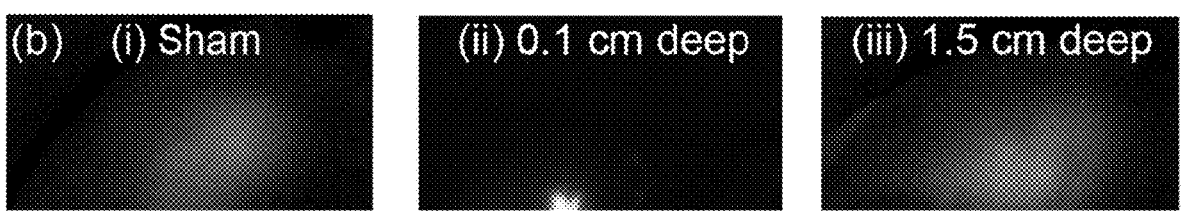
Figure 1C:
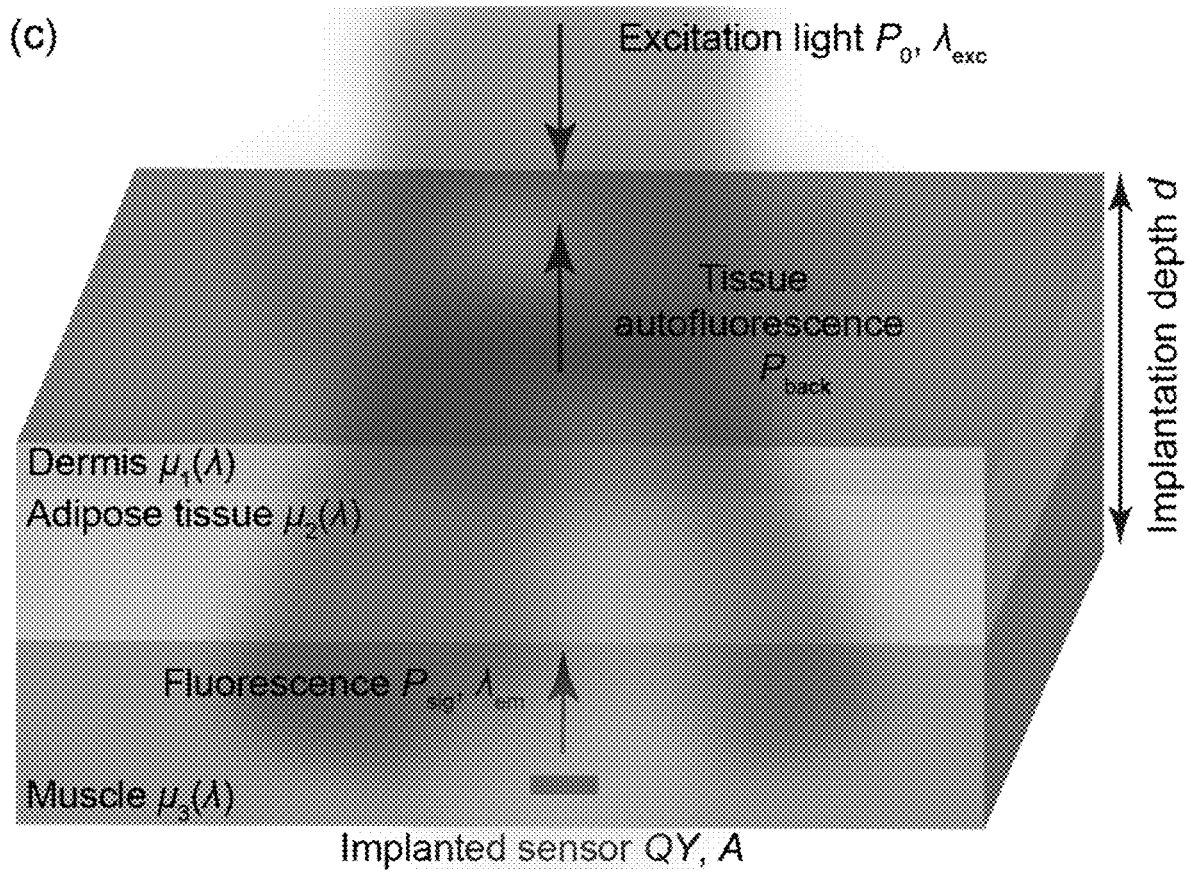

Light decays exponentially through biological tissue imposing a substantial limit on the detection depth. The near-infrared fluorescence image of a subcutaneously implanted model sensor, in the form of a hydrogel containing single-walled carbon nanotubes, in an SKH1-E mouse (FIGS. 1A and 1C) is readily visible from the site of implantation (FIG. 1B, panel (ii)) 1 mm deep. See, for example, A. A. Boghossian, J. Zhang, P. W. Barone, N. F. Reuel, J.-H. Kim, D. A. Heller, J.-H. Ahn, A. J. Hilmer, A. Rwei, J. R. Arkalgud, C. T. Zhang, M. S. Strano, Near-Infrared Fluorescent Sensors based on Single-Walled Carbon Nanotubes for Life Sciences Applications, ChemSusChem 4 (2011) 848-863; and J. Zhang, M. P. Landry, P. W. Barone, J.-H. Kim, S. Lin, Z. W. Ulissi, D. Lin, B. Mu, A. A. Boghossian, A. J. Hilmer, A. Rwei, A. C. Hinckley, S. Kruss, M. A. Shandell, N. Nair, S. Blake, F. Şen, S. Şen, R. G. Croy, D. Li, K. Yum, J.-H. Ahn, H. Jin, D. A. Heller, J. M. Essigmann, D. Blankschtein, M. S. Strano, Molecular recognition using corona phase complexes made of synthetic polymers adsorbed on carbon nanotubes, Nature Nanotechnology 8 (2013) 959, each of which is incorporated by reference in its entirety. The signal, however, vanishes when imaged through a 1.5 cm optical path (FIG. 1B, panel (iii)), becoming indistinguishable from the autofluorescent and scattering background of a sham implant (FIG. 1B, panel (i)). As the spatial information from deep implantation sites is scrambled, this work utilizes a single channel detector to collect the signal, minimizing noise that arises from spreading light over a pixel array (see below).

Figure 2A:
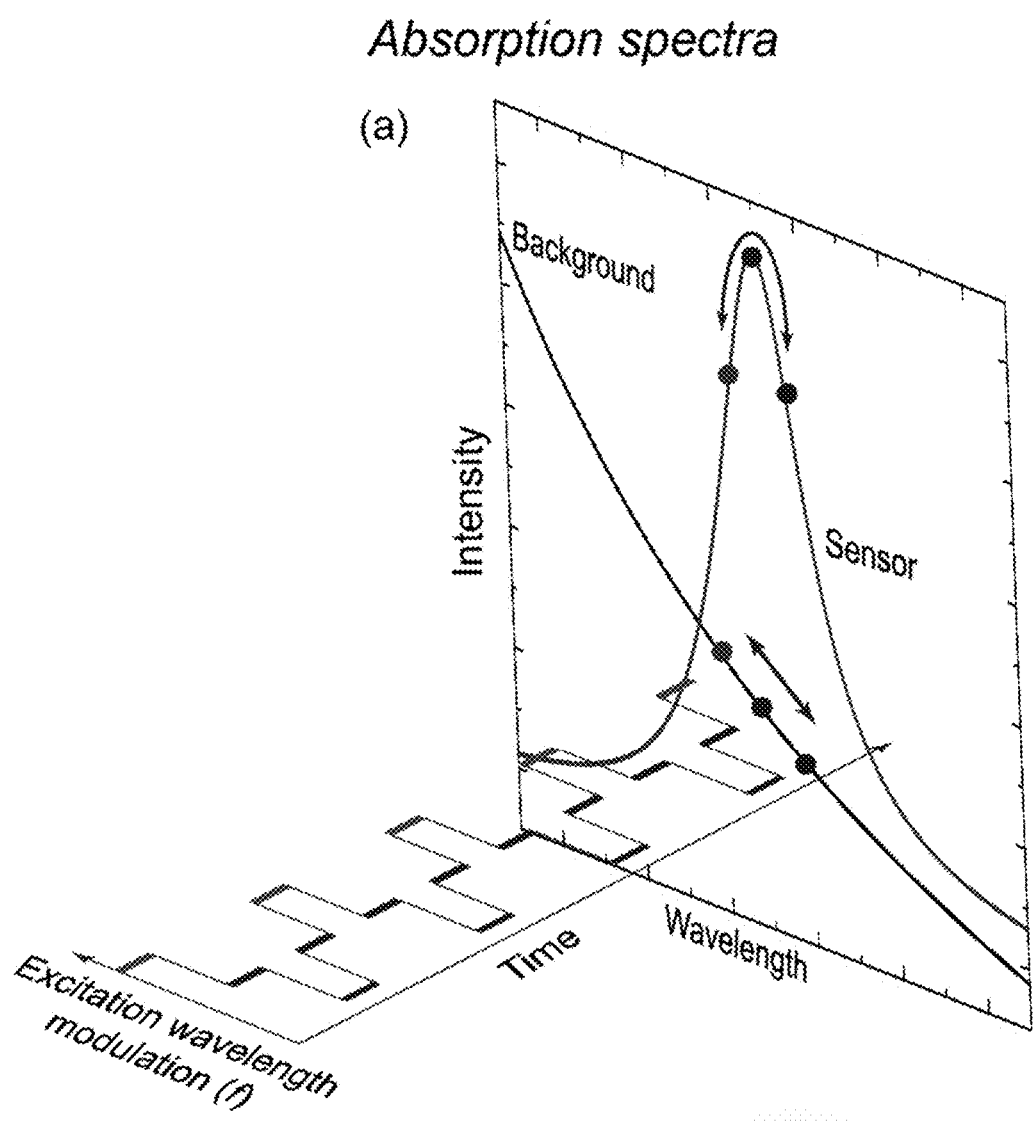
FIGS. 2A-2I depict principles of wavelength-induced frequency filtering.
Figure 2B:
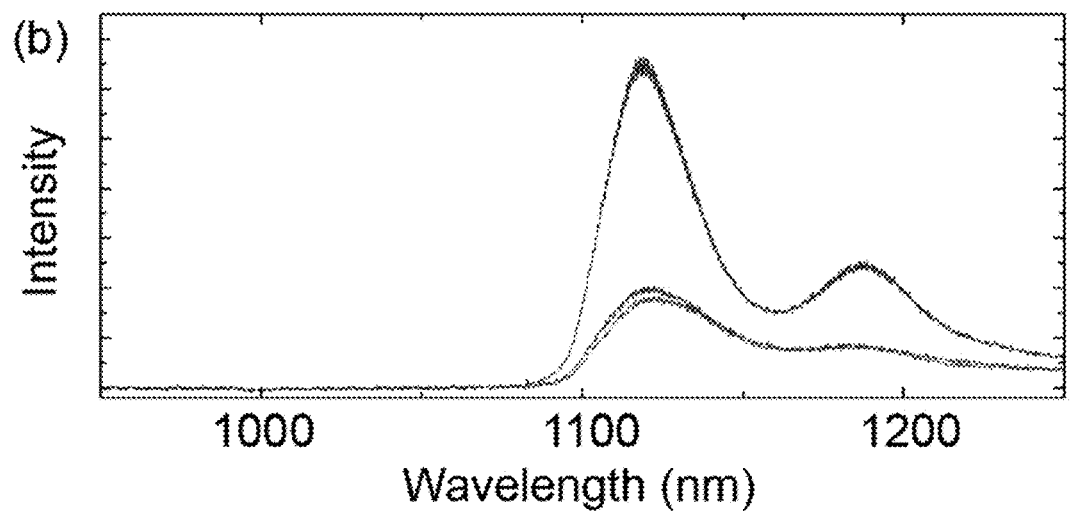
Figure 2C:
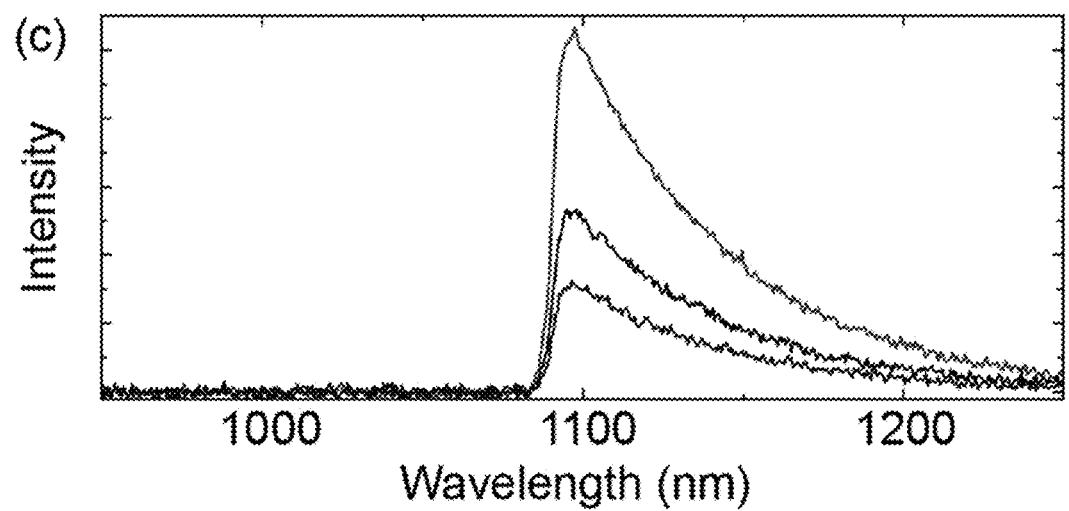
Figure 2D:
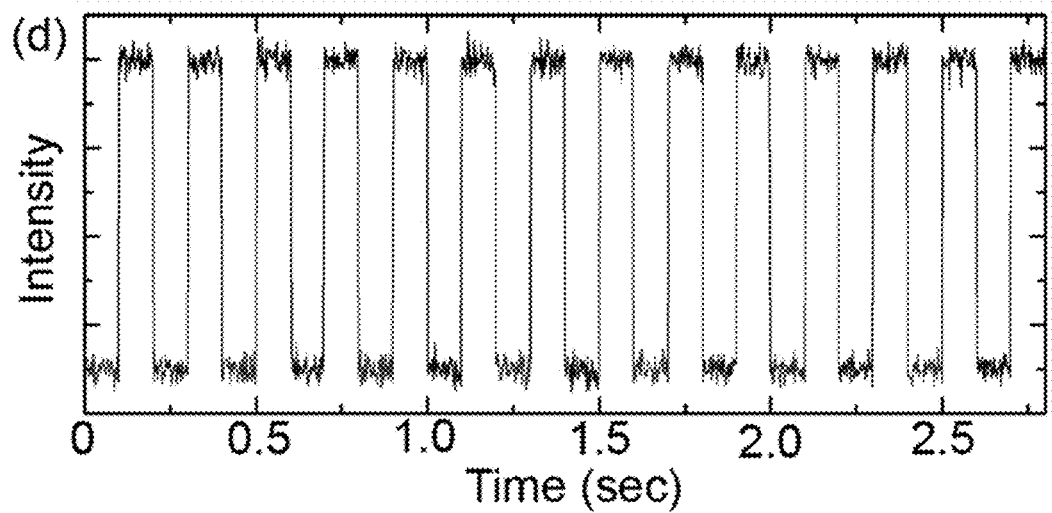
Figure 2E:
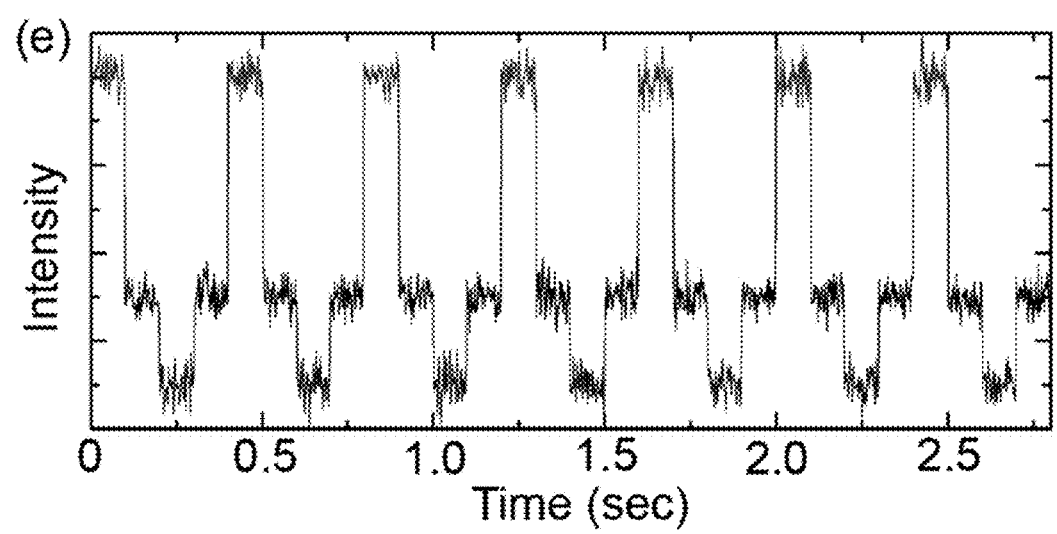

In a pursuit to lower the noise level, wavelength-induced frequency filtering (WIFF) is introduced. WIFF oscillates the excitation wavelength around the sensor absorption peak with a constant frequency f (FIG. 2A). This excitation profile produces a sensor signal that oscillates at 2f, while any monotonous background in this range will have a dominant f component that is easily filtered. The technique relies on the difference between the sensor and the background absorption peaks. The effect can be illustrated graphically (FIG. 2A, FIGS. 6A-6E). The resulting emission intensity can be found at the intersection of the excitation wavelength trace and the absorption spectrum, while the emission spectral ranges of a sensor and background overlap (FIGS. 2B and 2B). A sweep in excitation wavelength leads to a peak in the sensor signal and a monotonic trace in the background. Oscillating the excitation wavelength continuously will hence produce twice as many peaks in the sensor signal as compared to the background (FIGS. 2D and 2E). This principle allows WIFF to separate the overlapping sensor and background signals in the frequency domain.

Figure 7:
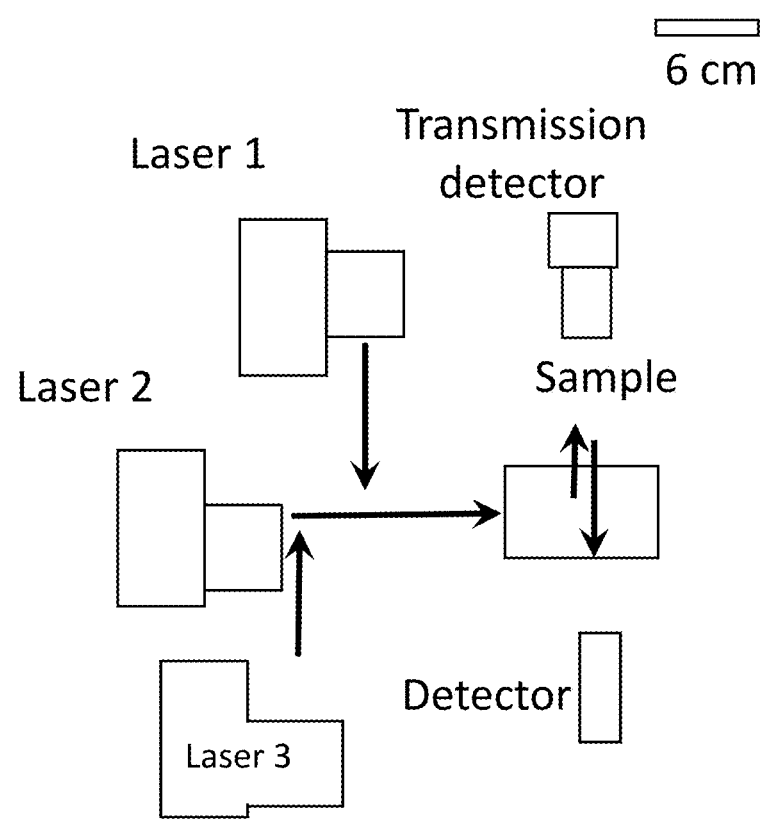
FIG. 7 depicts a photograph of the experimental setup for 3-laser WIFF. The excitation is programmed via a sequential opening of three mechanical shutters in front of the lasers. Red arrows show the excitation path, while a green (downward) arrow—collection.
Figure 8A:
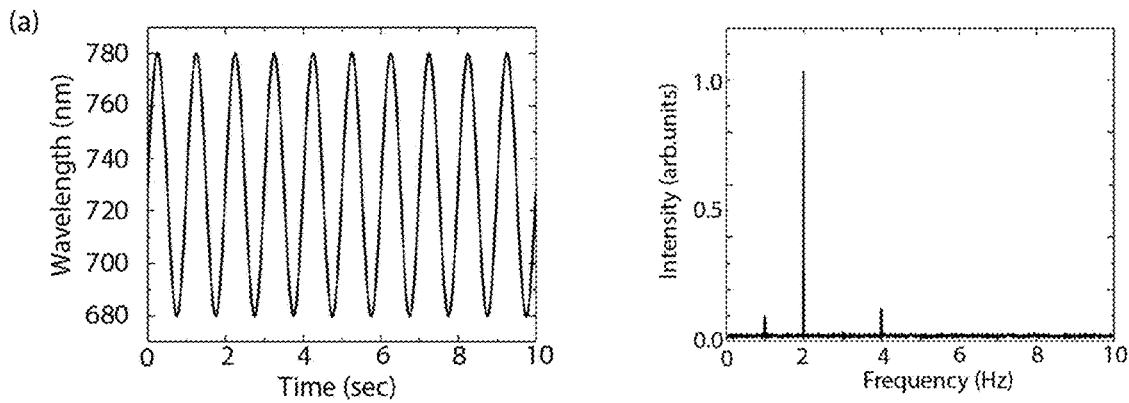
FIGS. 8A-8F depict types of wavelength modulation. Comparison of the simulated wavelength modulated signals over the carbon nanotube spectrum (peak 1150 nm) and their Fourier transforms (the percent of 2f component over the total power is given in brackets)
Figure 8B:
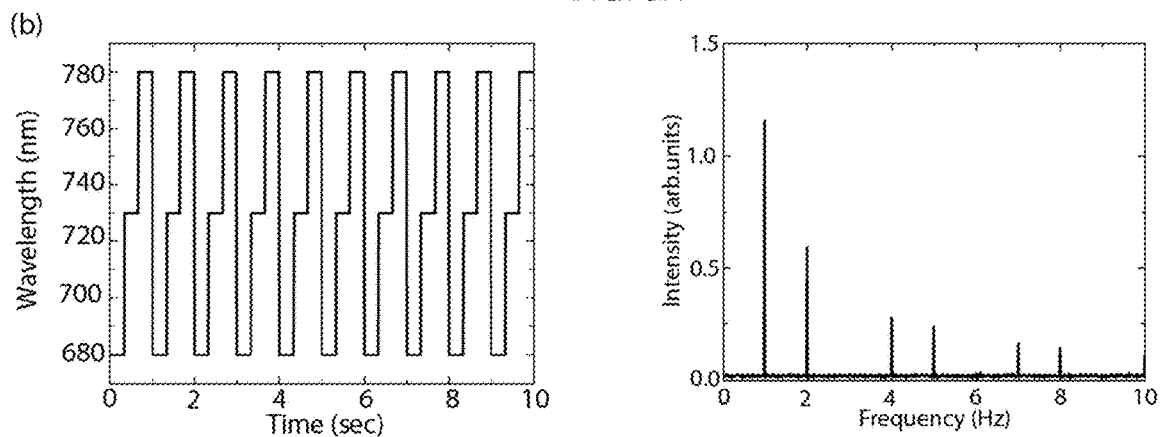
Figure 8C:
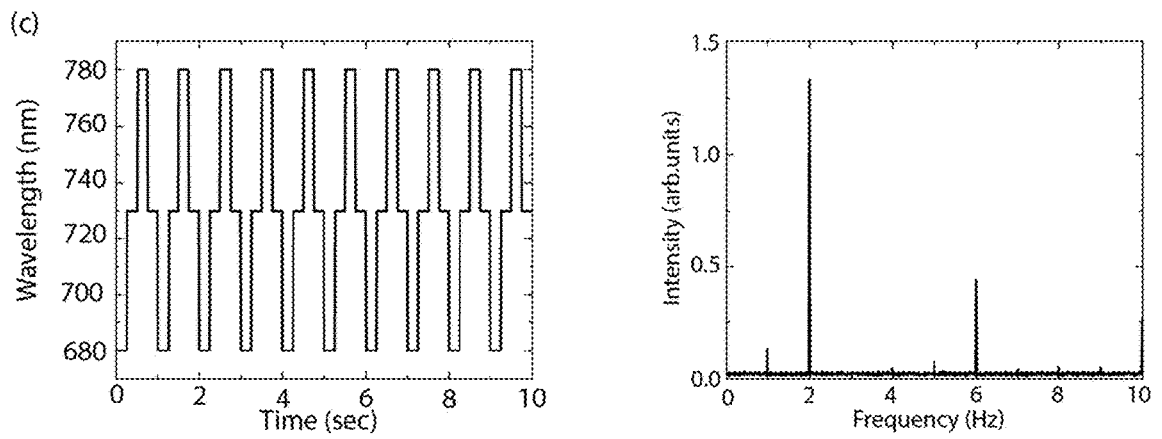
Figure 8D:
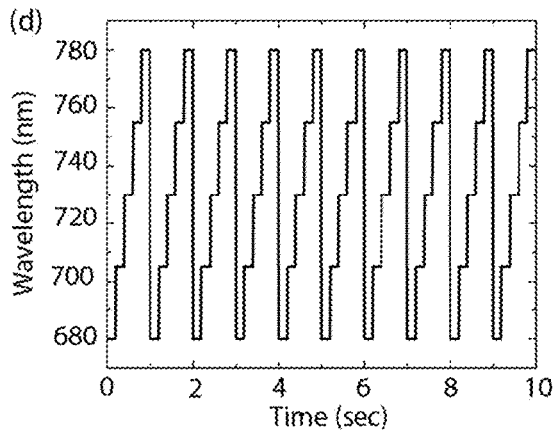
Figure 8D:
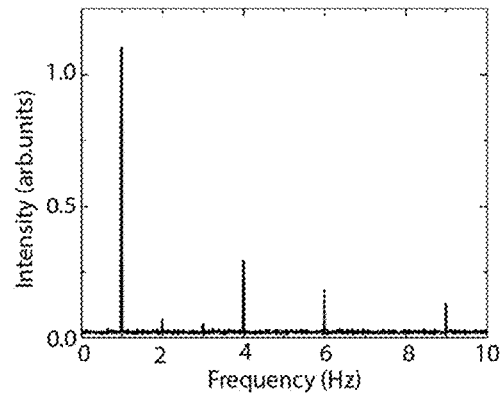
Figure 8E:
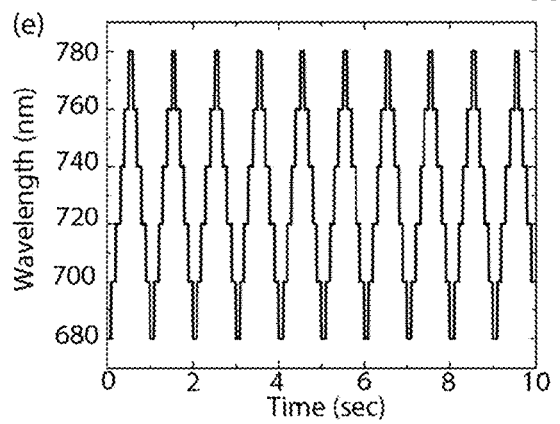
Figure 8E:
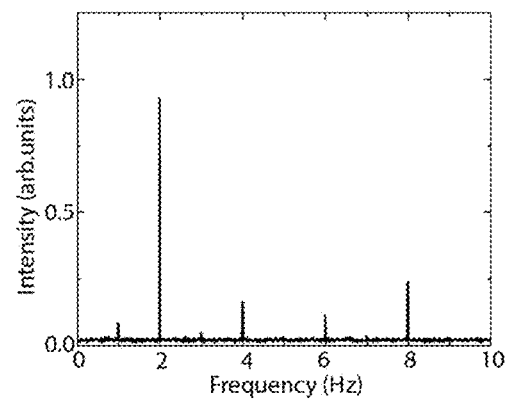
Figure 8F:
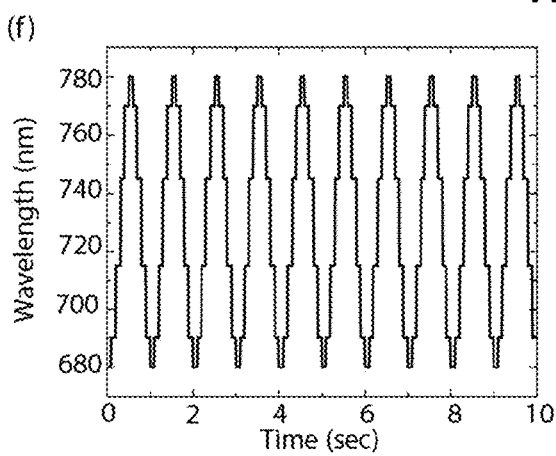
Figure 8F:
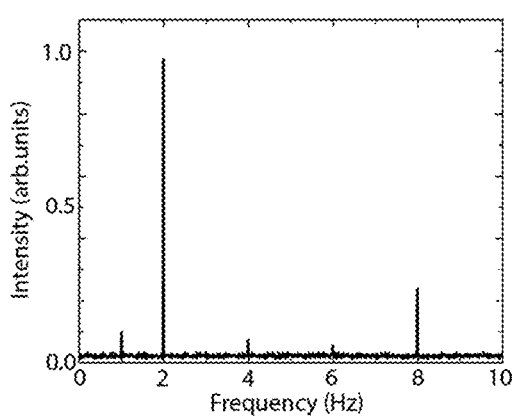
Figure 9A:
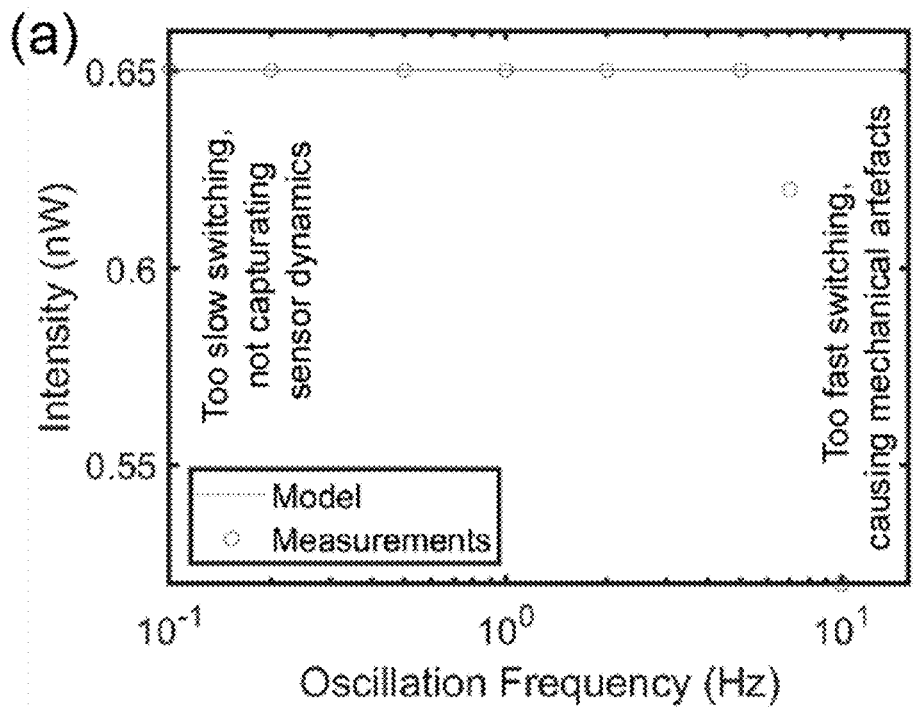
FIGS. 9A-9D depict numerical simulation and experimental results for tuning WIFF oscillation frequency.
Figure 9B:
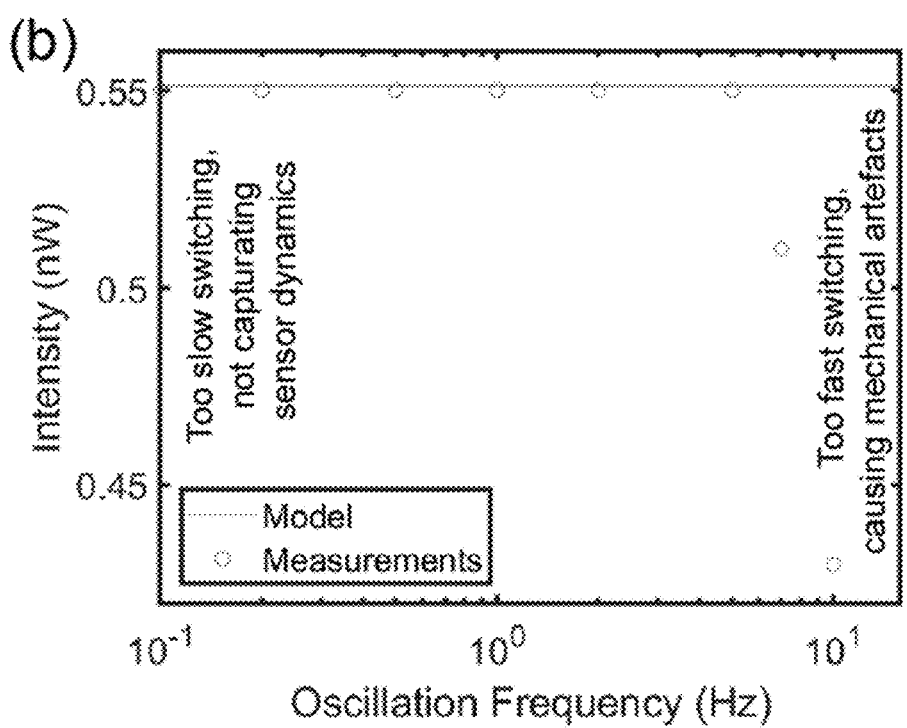
Figure 9C:
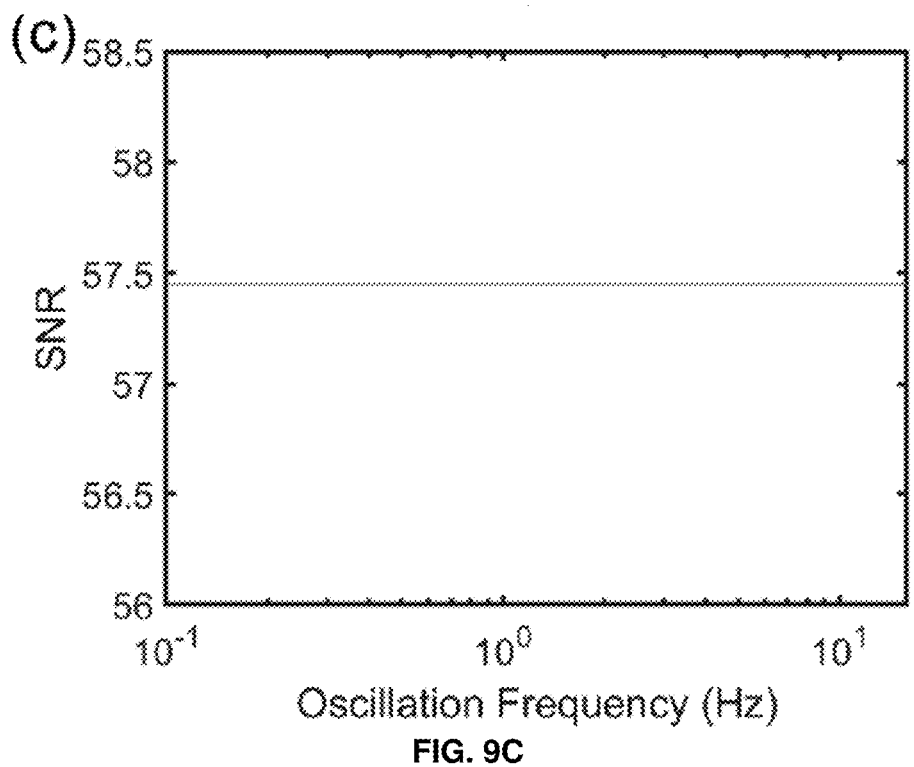
Figure 9D:
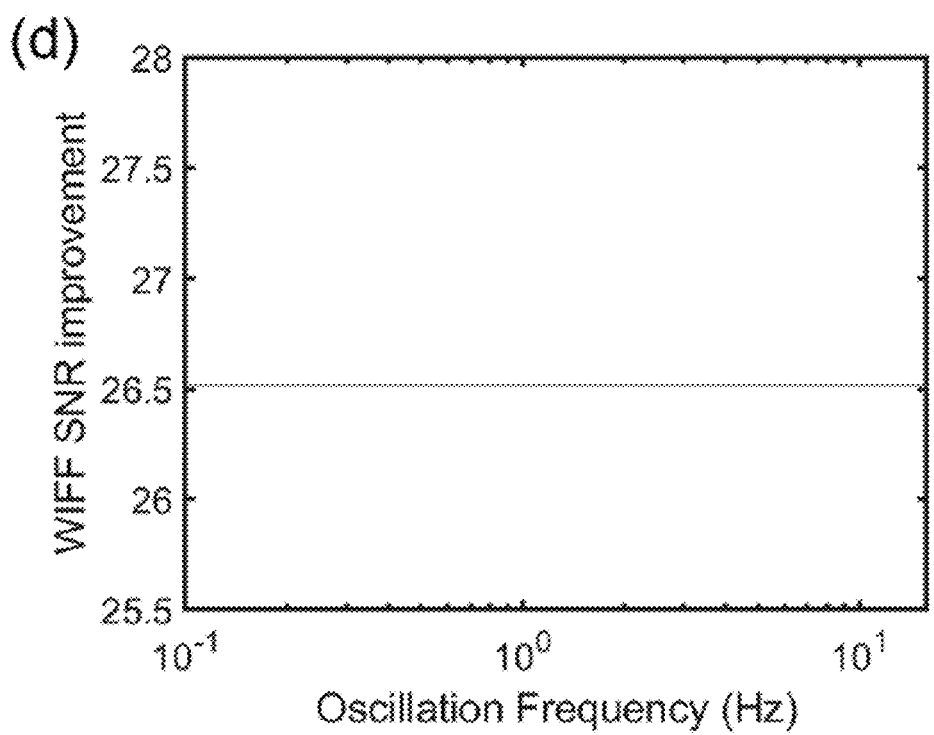

The main technical challenge associated with the experimental implementation of WIFF lies in the ability to perform wavelength modulation with amplitudes comparable to the absorption linewidths and repetition rates fast enough to capture sensor dynamics. Currently, tunable lasers and filters provide milliseconds of tuning times for MHz wavelength ranges that are used in probing narrow gas absorption lines. See, for example, G. B. Rieker, J. B. Jeffries, R. K. Hanson, Measurements of high-pressure CO2 absorption near 2.0 µm and implications on tunable diode laser sensor design, Applied Physics B 94 (2009) 51-63, which is incorporated by reference in its entirety. For fluorescent sensors that typically have their absorption lines in the range of 20-50 nm, the tuning times are limited to a few seconds. To implement WIFF, a system based on three lasers with equally spaced wavelengths and mechanical shutters programmed to open sequentially (FIG. 2F and FIG. 7) was developed. As a result, this setup allows changing excitation wavelengths that are 50 nm apart faster than 10 Hz to collect up to 15% of the signal in the 2f component with other modulation schemes less effective (FIGS. 8A-8F).

Figure 2F:
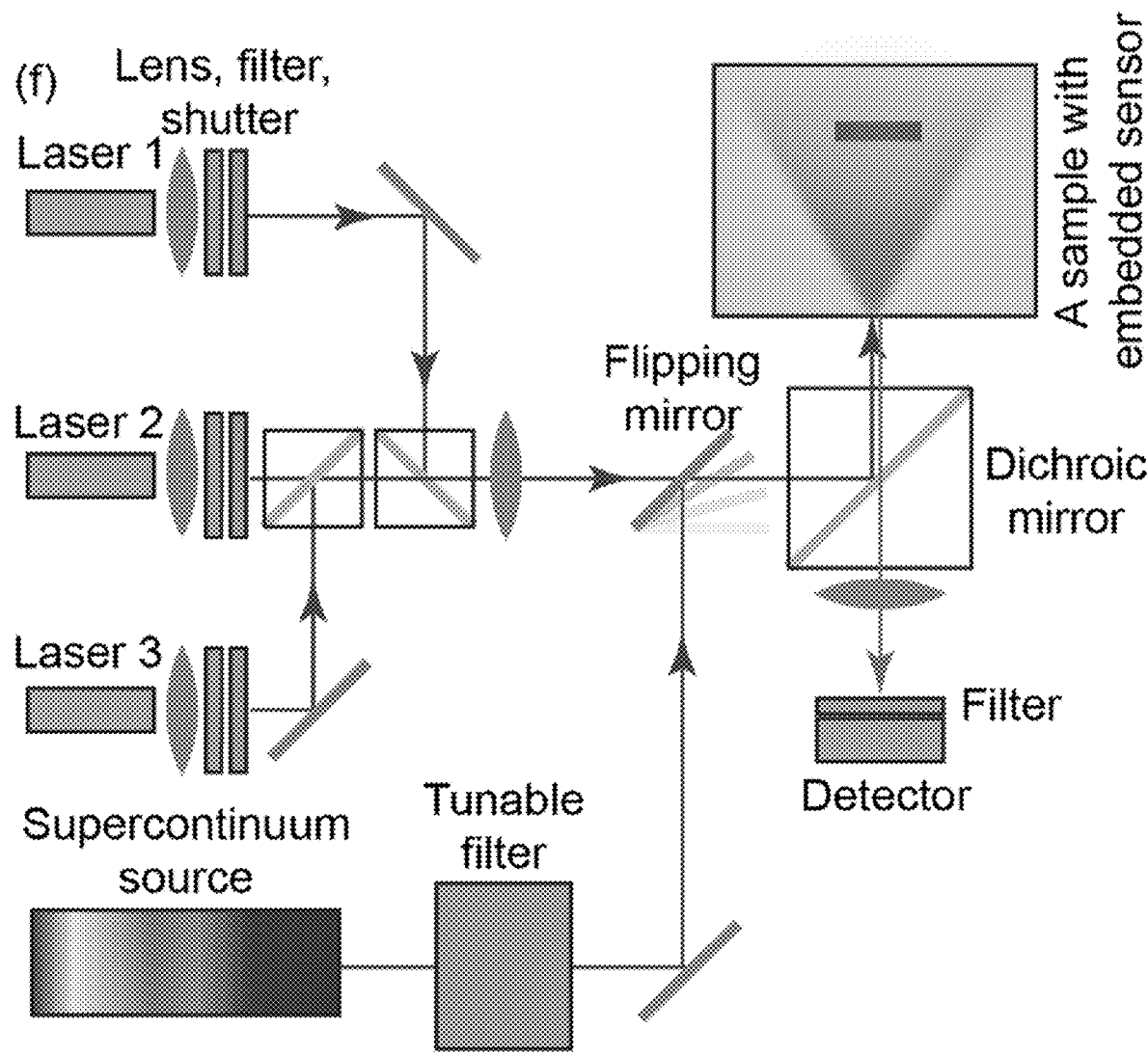
Figure 2G:
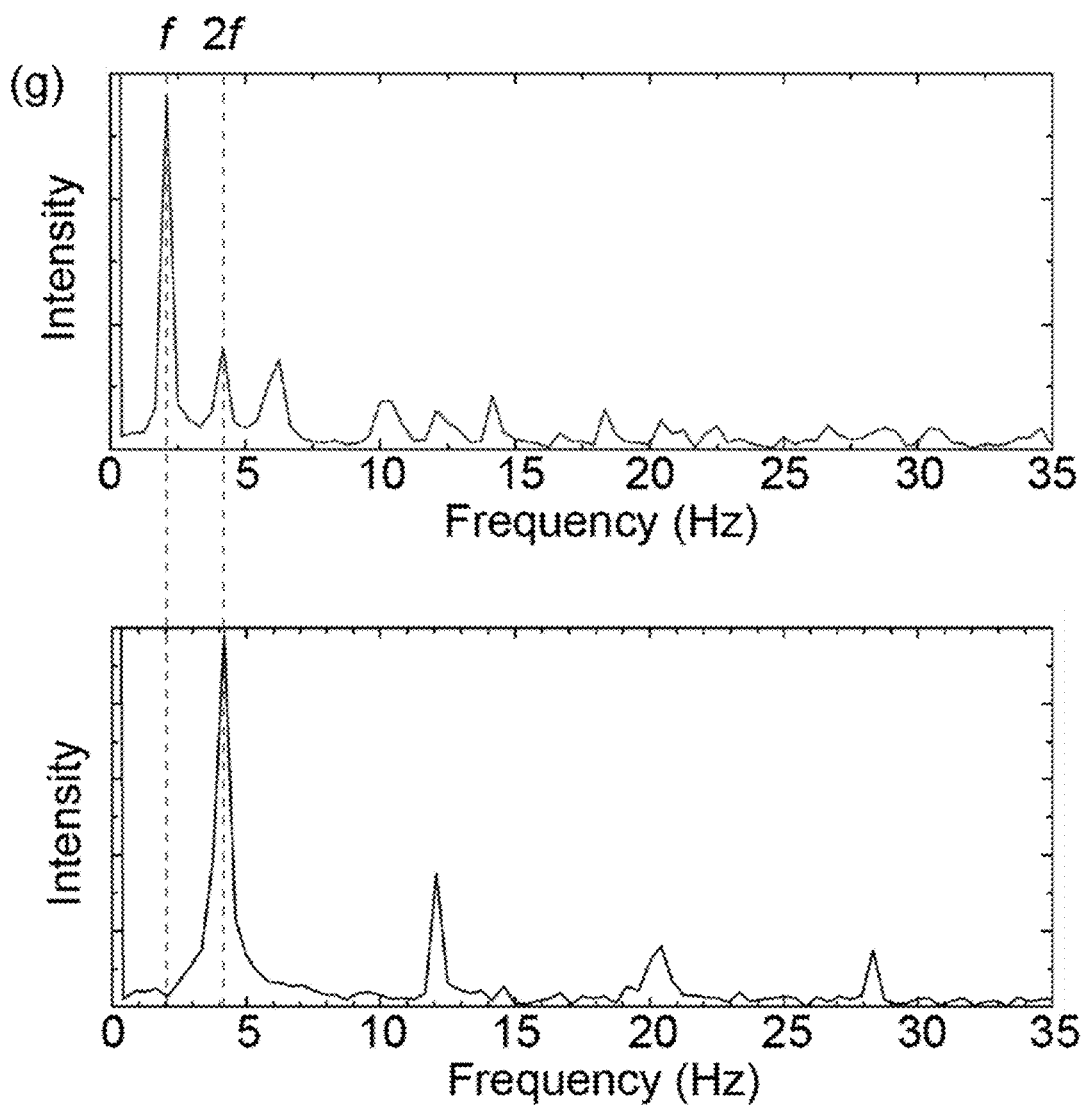
Figure 10A:
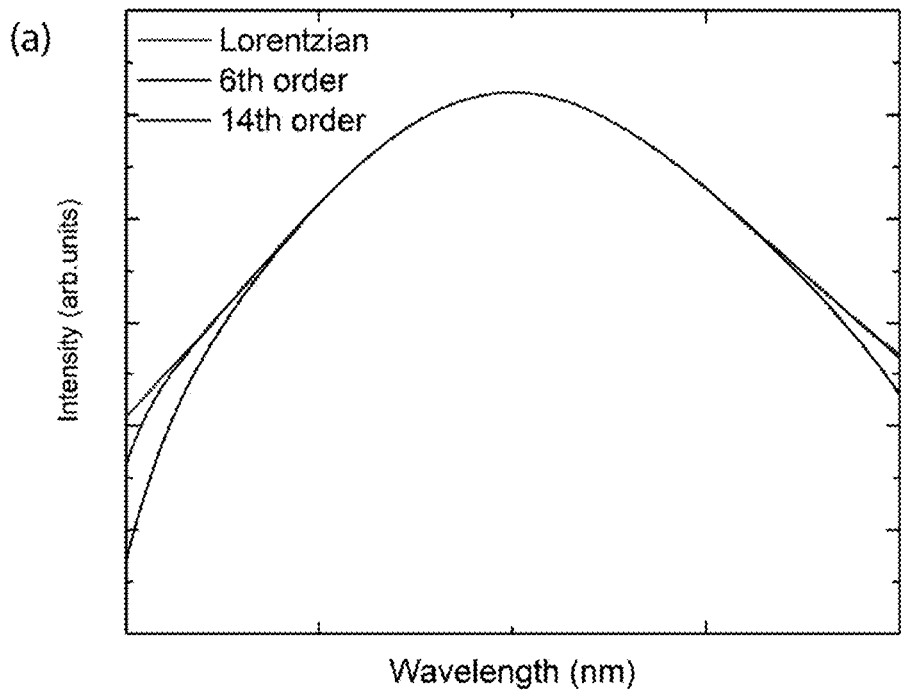
FIGS. 10A-10B depict Taylor expansion for the nanosensor absorption line.
Figure 10B:
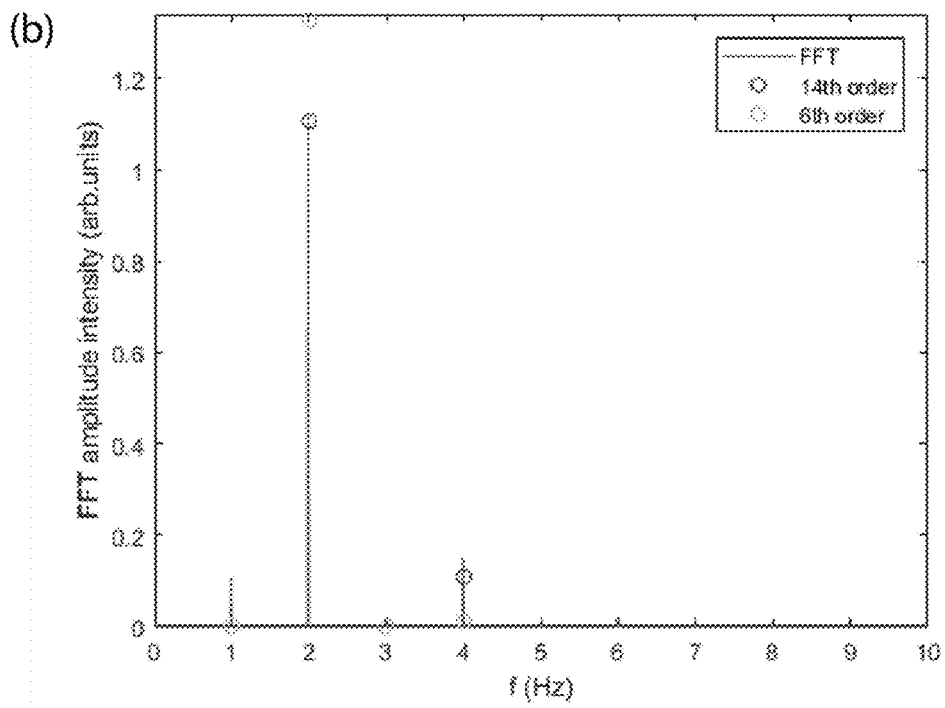
Figure 11:
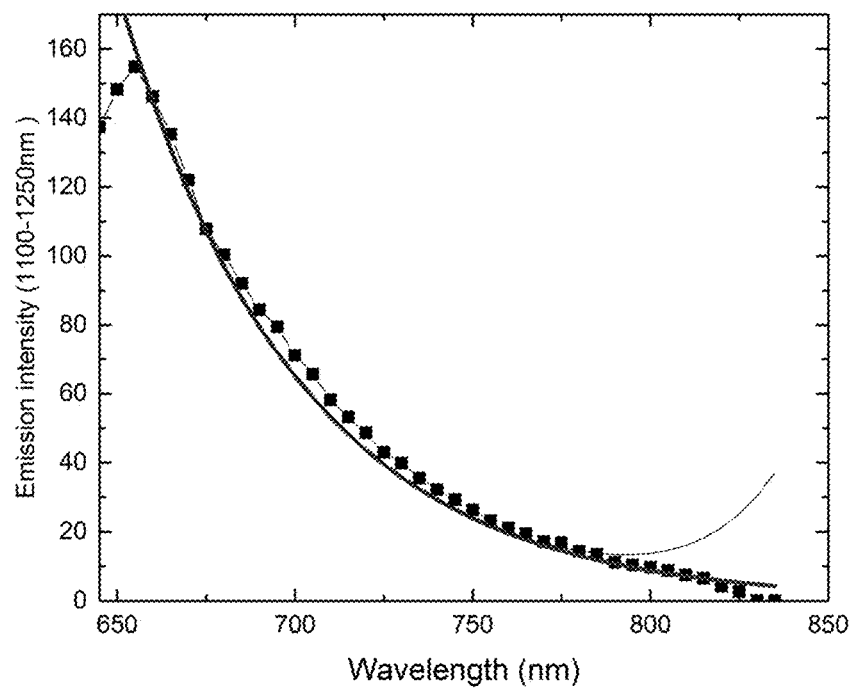
FIG. 11 depicts tissue autofluorescence absorption spectrum. The spectrum was extracted as the total emitted power in the 1100-1250 nm region for a given excitation wavelength for the stomach mouse tissue. The red line is the exponential fit with the rate α=0.02. The blue line is the Taylor expansion approximation.
Figure 12:
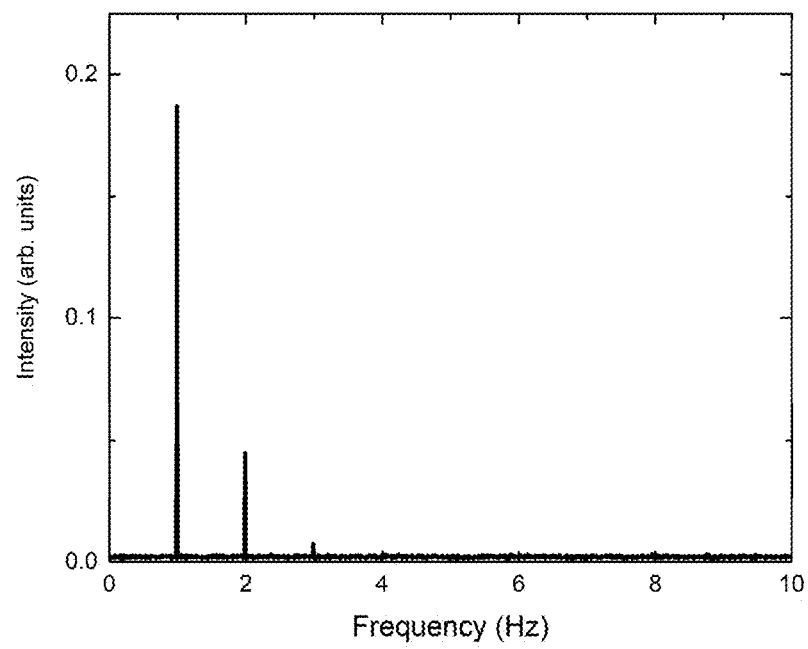
FIG. 12 depicts a numerical estimation of FFT from the background signal. FFT amplitude intensity extracted numerically from the background signal with 10% of intensity contained in 2f component and G being 0.25.

The experimental implementation uses three lasers of 680 nm, 730 nm, and 780 nm that excite the fluorescent sensor in a stepwise manner at f=2 Hz and a single channel detector to collect the emitted fluorescence (FIG. 2F). As evident from time traces (FIGS. 2D and 2E) and Fourier analysis (FIG. 2G), this excitation drives the fluorescence signal at 2f, while the background has a dominant f component, deconvolving the two. In the system, mechanical artefacts caused by shutter vibrations become considerable above 5 Hz modulation (FIGS. 9A-9D), well above the dynamics of various biomedical processes. See, for example, N. M. Iverson, P. W. Barone, M. Shandell, L. J. Trudel, S. Sen, F. Sen, V. Ivanov, E. Atolia, E. Farias, T. P. McNicholas, N. Reuel, N. M. A. Parry, G. N. Wogan, M. S. Strano, In vivo biosensing via tissue-localizable near-infrared-fluorescent single-walled carbon nanotubes, Nature Nanotechnology 8 (2013) 873, which is incorporated by reference in its entirety. Approximating the absorption profile of the probe with a Lorentzian lineshape, the fluorescent signal $P_s$ can be found as (FIGS. 10A-10B):

$$P_S(\lambda) = A \frac{1}{(\lambda - \lambda_{11})^2 + \gamma^2}, \quad (1)$$

where A is an amplitude constant, $\lambda$ and $\lambda_{11}$ are excitation and peak center wavelengths, respectively, $\gamma$ is another constant that determines peak linewidth. The background signal $P_b$ can be approximated as (FIG. 11):

$$P_b(\lambda) = B \exp[-\alpha(\lambda - \lambda_0)], \quad (2)$$

where B and $\alpha$ are fitting parameters (found to be 0.02 for SKH1-E mouse tissues in 680-800 nm region), and $\lambda_0$ is the absorption peak of autofluorescence (taken to be 655 nm). Expanding Eq. (1) and (2) into a Taylor series and taking the Fourier transform, expressions for the signal harmonics can be found (FIGS. 10A-10B and 12, and see below). It can be further shown that a ratio between f and 2f background components:

$$G = \frac{P_b(2f)}{P_b(f)}, \quad (3)$$

depends only on the spectral shape of the tissue and the excitation modulation, but is invariant to the excitation power or collection efficiency. For the modulation width of 50 nm, G was estimated being 0.27 for SKH1-E mouse tissues as in FIG. 11. Although different organs have some variations in absorption profiles, G remains constant for whole-animal experiments when measured from the animal side as will be shown below. Assuming that the sensor provides no f component (or it is very low compared to that of the background), one can effectively filter out background contribution to the signal:

$$P_{WIFF} = |P_{s+b}(2f) - GP_{s+b}(f)|. \quad (4)$$

Eq. (4) allows performing self-referenced measurements where 2f-component is corrected by f-component that mostly bears the background signal.

Figures 2H, 2I:
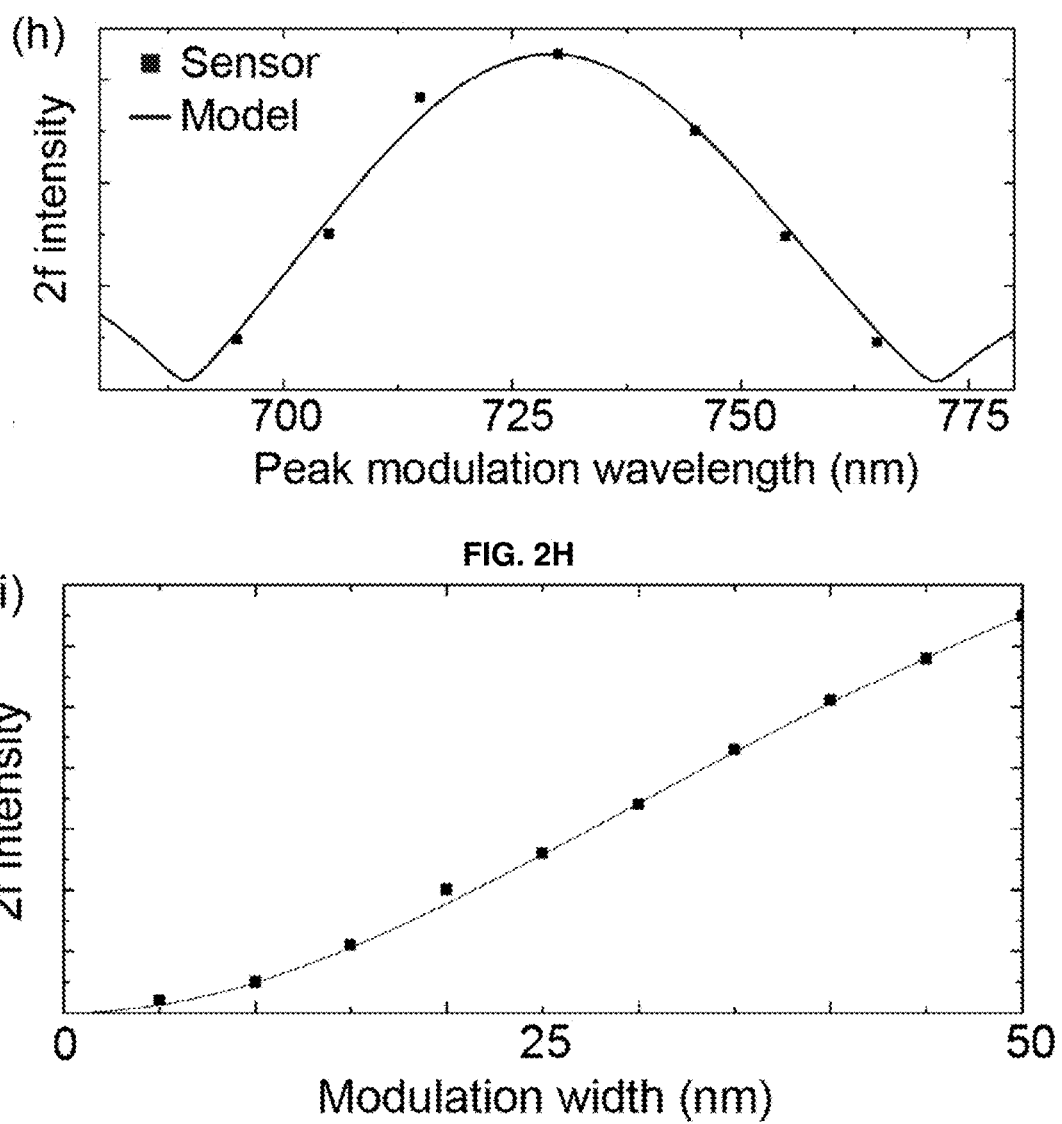
Figure 13A:
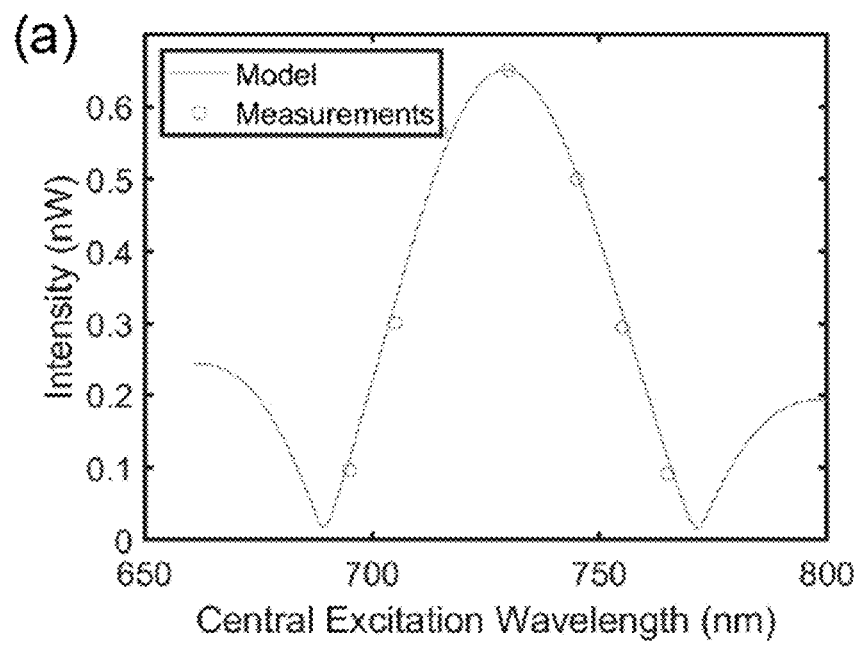
FIGS. 13A-13D depict numerical simulation and experimental results for tuning the WIFF central excitation wavelength.
Figure 13B:
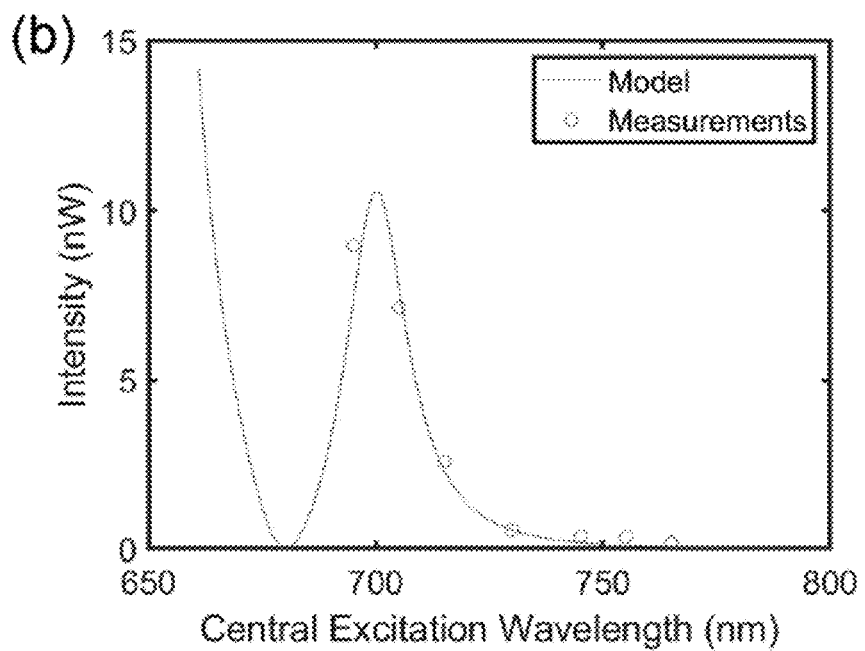
Figure 13C:
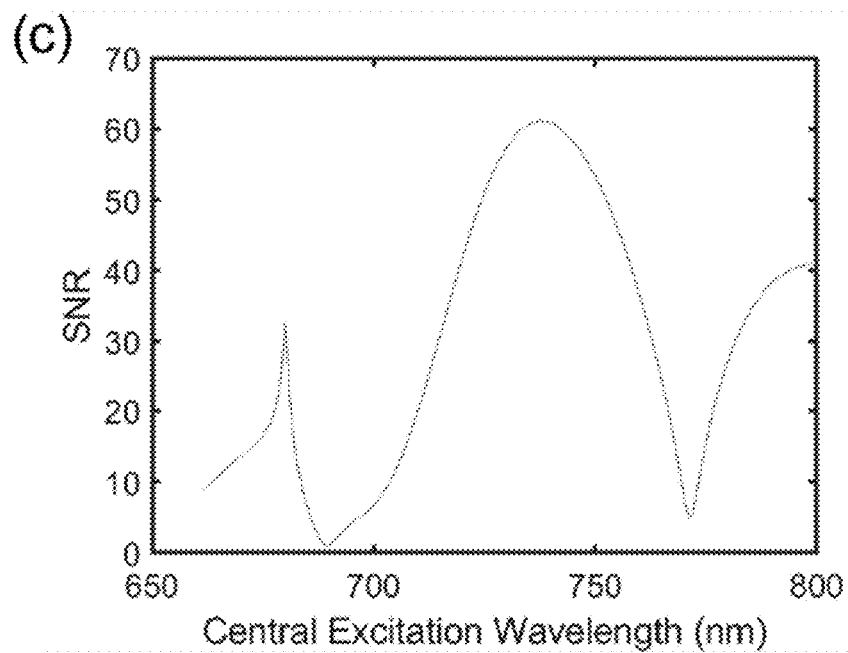
Figure 13D:
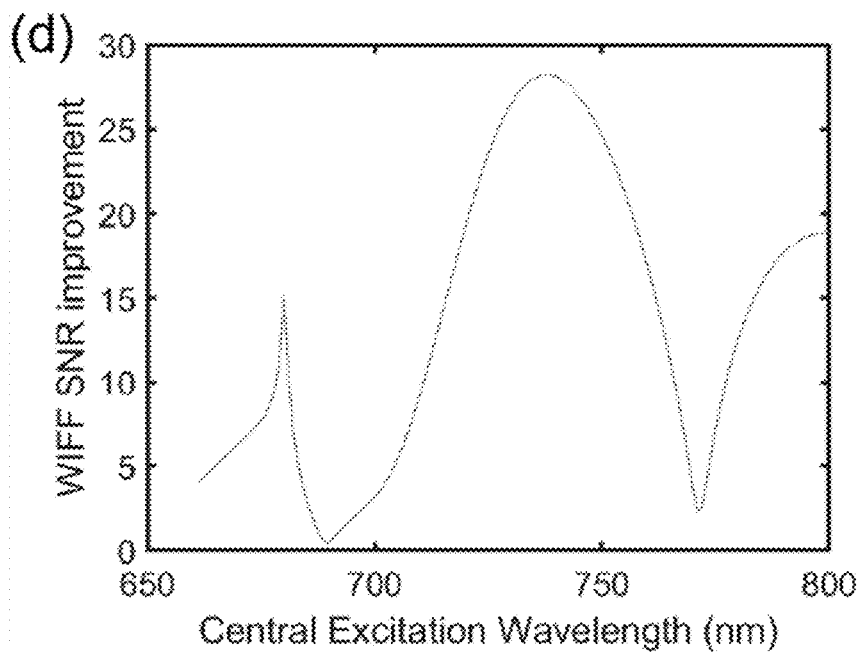
Figure 14A:
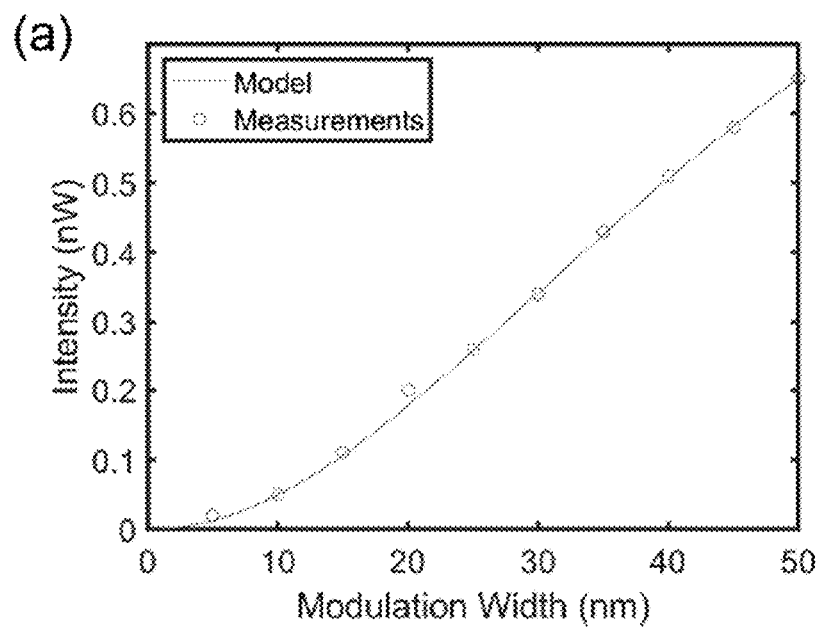
FIG. 14A-14D depict numerical simulations and experimental results for tuning WIFF modulation width.
Figure 14B:
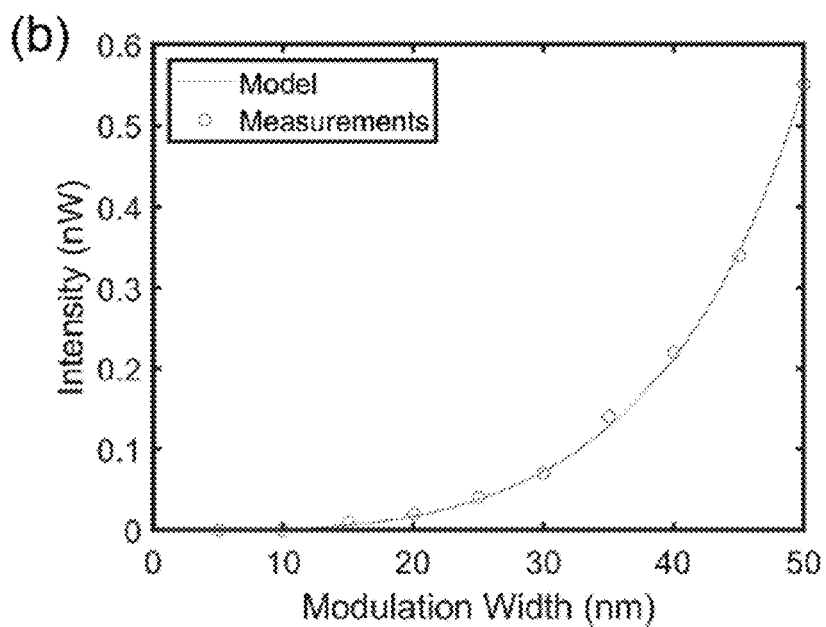
Figure 14C:
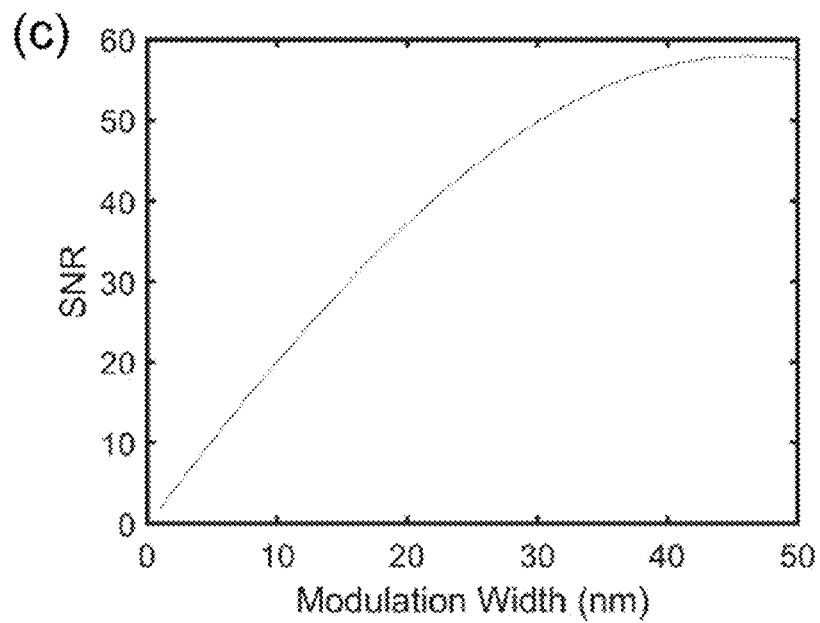
Figure 14D:
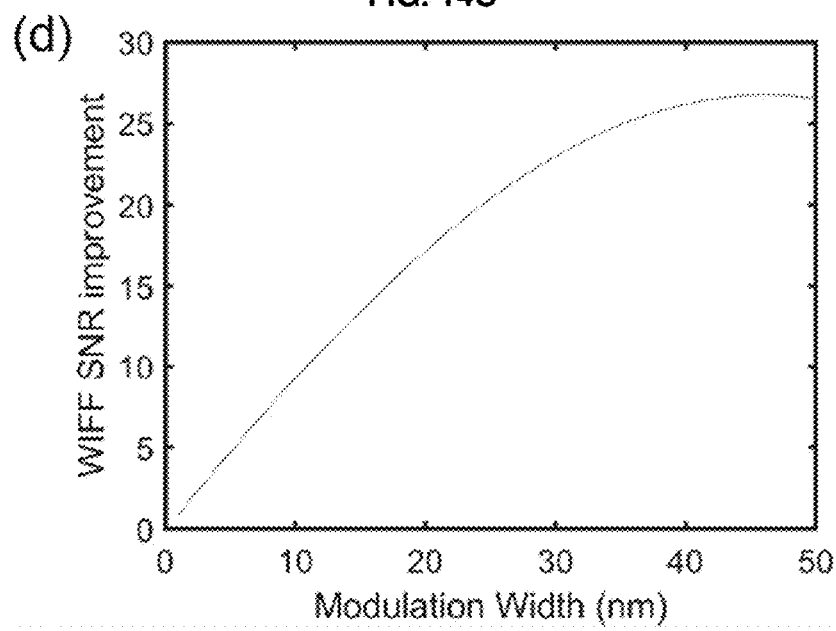
Figure 15A:
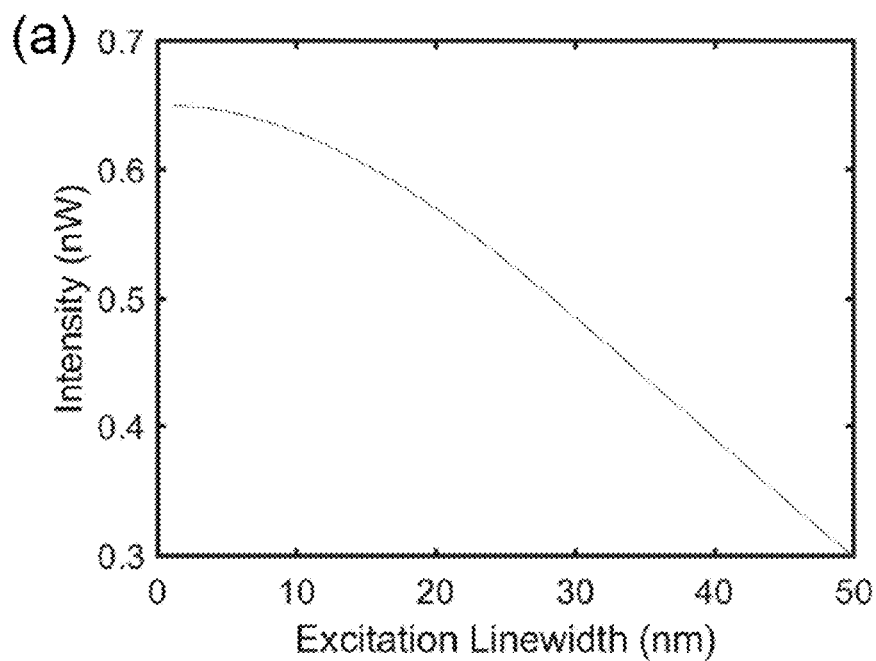
FIGS. 15A-15D depict numerical simulation for tuning WIFF excitation linewidth.
Figure 15B:
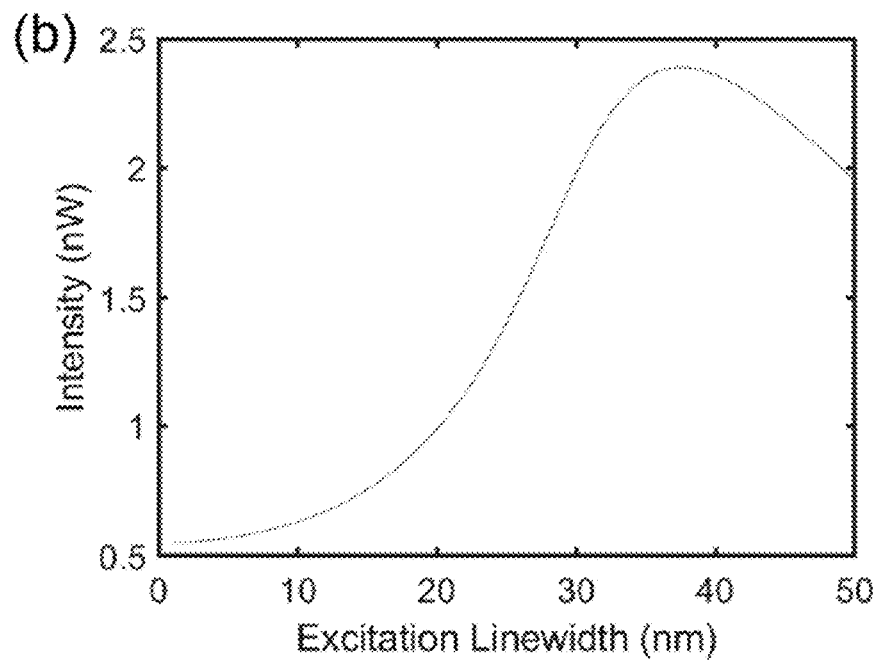
Figure 15C:
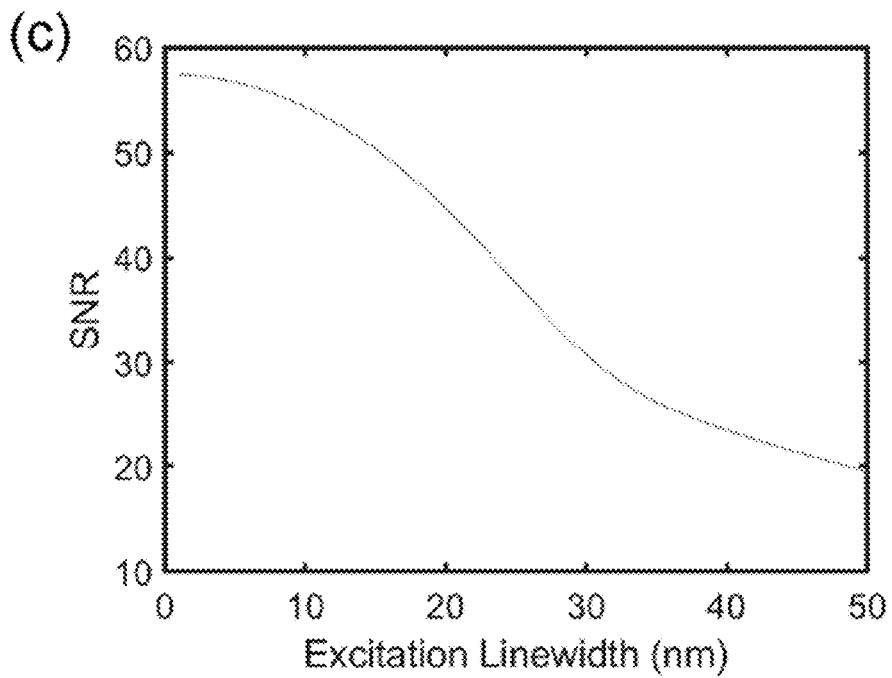
Figure 15D:
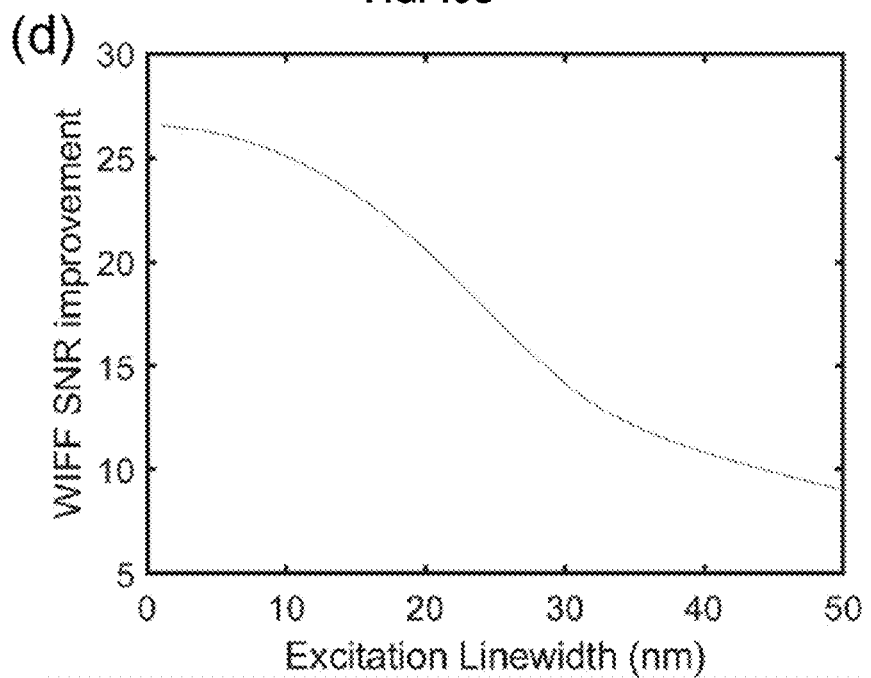
Figure 16A:
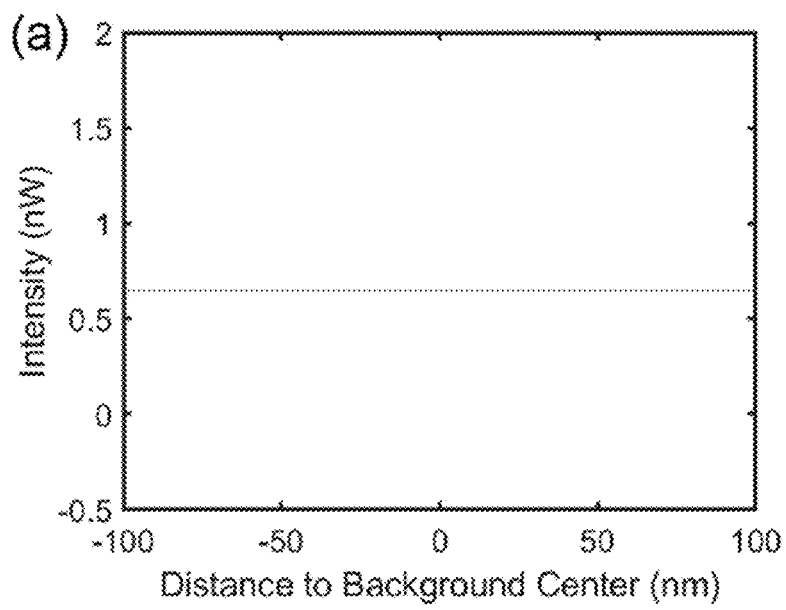
FIGS. 16A-16D show numerical simulation for tuning the distance between a fluorophore absorption peak and the background absorption peak.
Figure 16B:
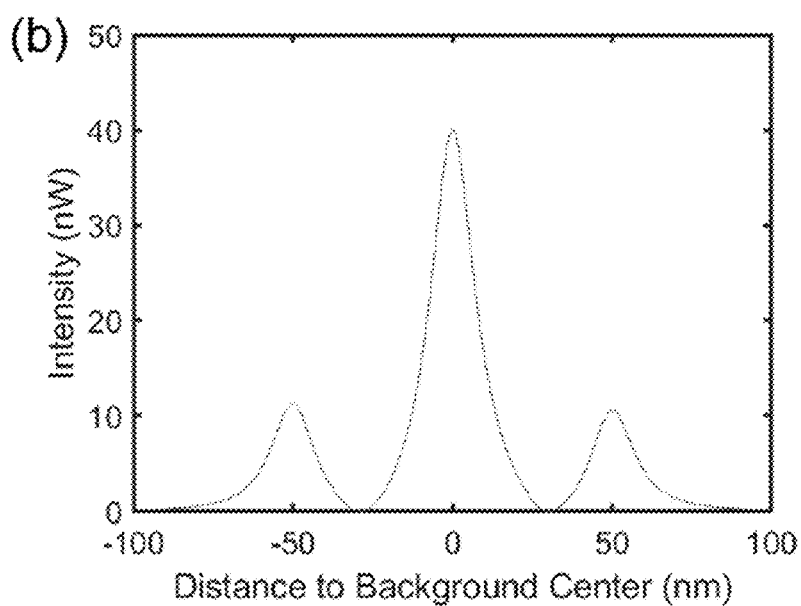
Figure 16C:
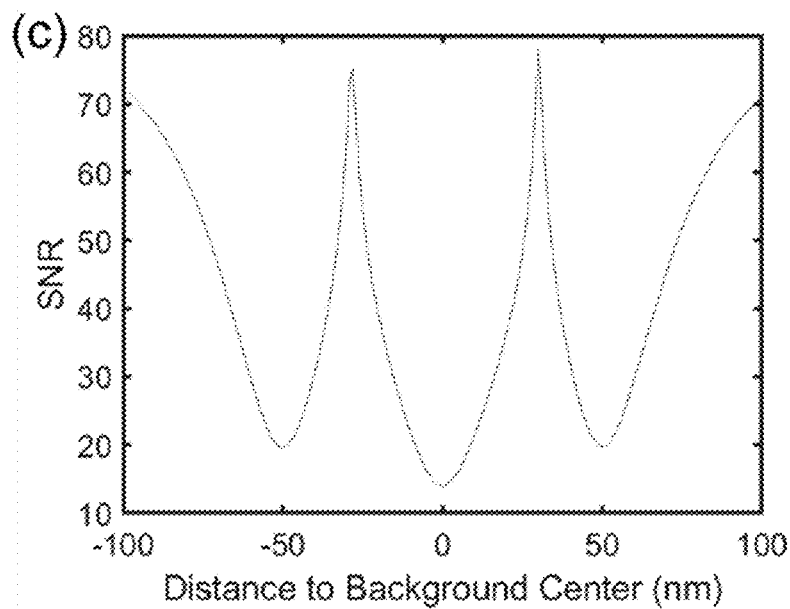
Figure 16D:
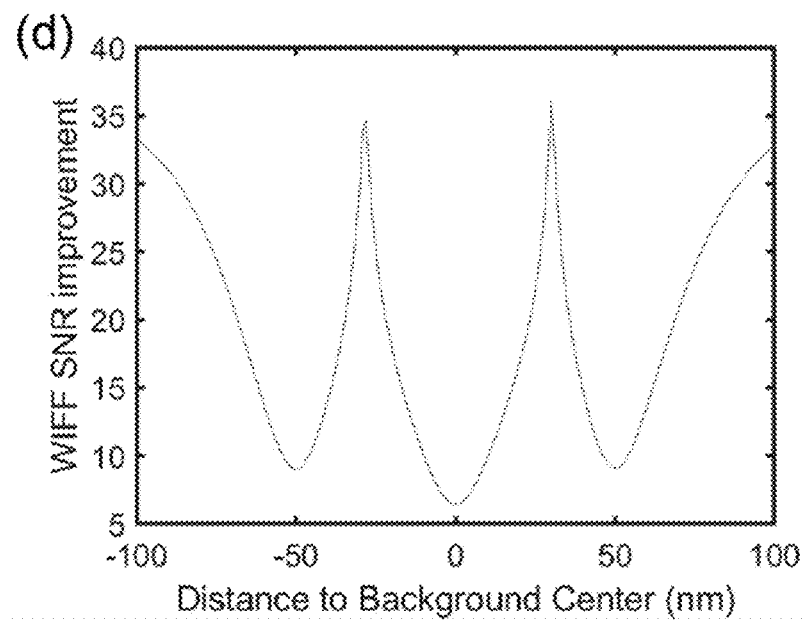

To understand the limits of WIFF application, a supercontinuum laser (or continuum laser) was employed with a tunable filter to tune the wavelength modulation excitation (this source allows for greater tunability, but with much lower modulation frequencies of only 0.1 Hz). The intensity of 2f-component strongly depends on the excitation wavelength and, as expected, peaks at the absorption maximum (FIG. 2H, FIGS. 13A-13B, and see below). By providing a better contrast between the power at the peak and sidebands, both the modulation width (FIG. 2I and FIGS. 14A-14D) and narrow laser linewidth (FIGS. 15A-15D) further increase the 2f-component. Finally, to minimize background 2f-component, the distance between the background and the signal absorption peaks needs to exceed the modulation width, ensuring the monotonicity of the background (FIGS. 16A-16D).

WIFF Enables Extremely Deep Tissue Sensing

Figure 3A:
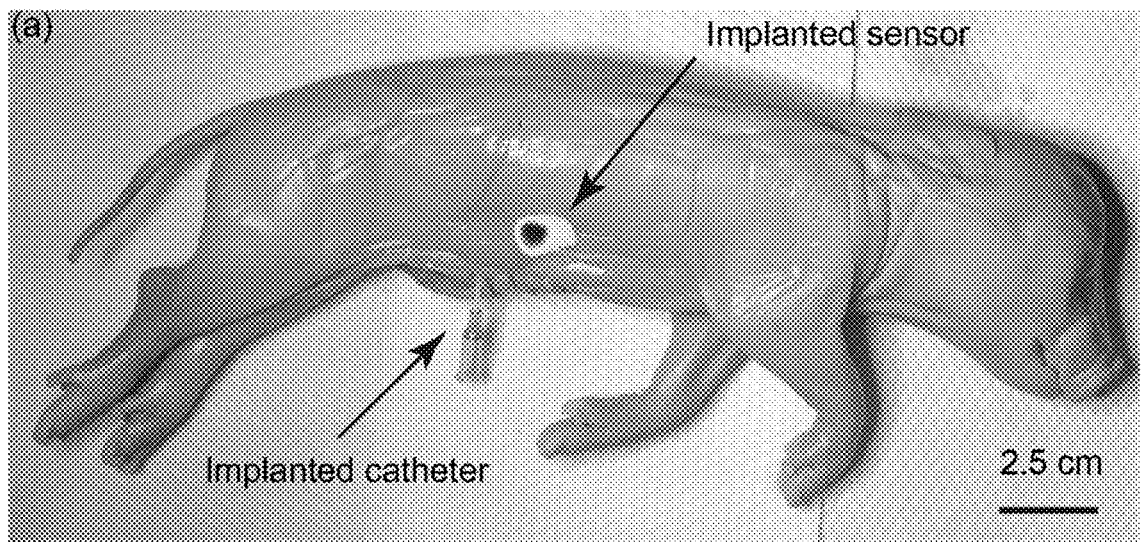
FIGS. 3A-3G depict WIFF performance in a complex tissue.
Figure 3B:
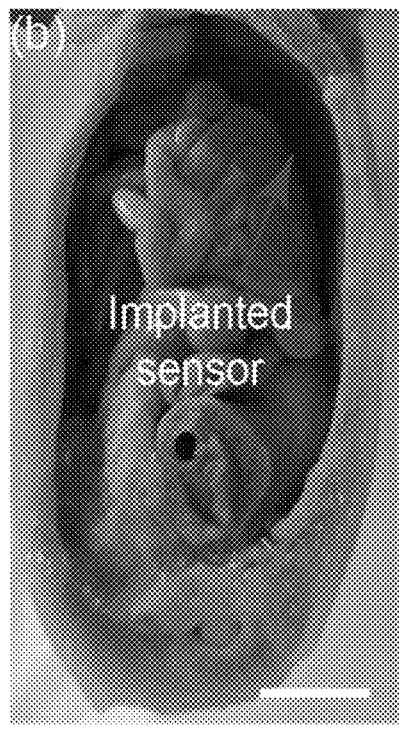

To better understand how WIFF increases the SNR and improves sensing, model fluorescent sensors were implanted into the intraperitoneal space from the ventral side of the preserved fetal pigs (FIGS. 3A and 3B). The intraperitoneal space is often used for injections in veterinary medicine as well as for the administration of chemotherapeutic drugs in humans. See, for example, T. Shimada, M. Nomura, K. Yokogawa, Y. Endo, T. Sasaki, K.-i. Miyamoto, Y. Yonemura, Pharmacokinetic advantage of intraperitoneal injection of docetaxel in the treatment for peritoneal dissemination of cancer in mice, Journal of Pharmacy and Pharmacology 57 (2005) 177-181; and Z. Lu, J. Wang, M. G. Wientjes, J. L. S. Au, Intraperitoneal therapy for peritoneal cancer, Future Oncol 6 (2010) 1625-1641, each of which is incorporated by reference in its entirety. In this geometry, light has to travel through layers of tissue and fluids with various refractive indexes, such as dermis, adipose, muscle, and peritoneum, to reach the implanted sensor. As an example, a model optical sensor was used for riboflavin, a vitamin in the body that can be administered in case of its deficiency, with sensitivities down to 10 nM concentrations. See, for example, J. Zempleni, J. R. Galloway, D. B. McCormick, Pharmacokinetics of orally and intravenously administered riboflavin in healthy humans, The American Journal of Clinical Nutrition 63 (1996) 54-66; and M. Park, D. P. Salem, D. Parviz, X. Gong, K. S. Silmore, T. T. S. Lew, D. T. Khong, M. C.-Y. Ang, S.-Y. Kwak, M. B. Chan-Park, M. S. Strano, Measuring the Accessible Surface Area within the Nanoparticle Corona Using Molecular Probe Adsorption, Nano Letters 19 (2019) 7712-7724, each of which is incorporated by reference in its entirety.

Figure 3C:
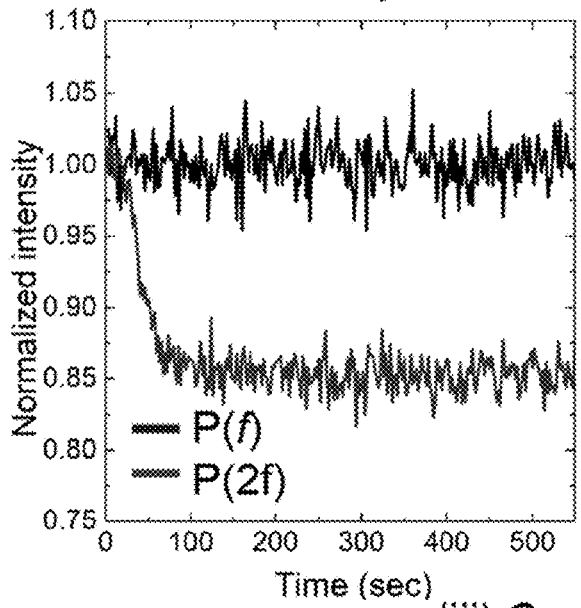
Figure 3C:
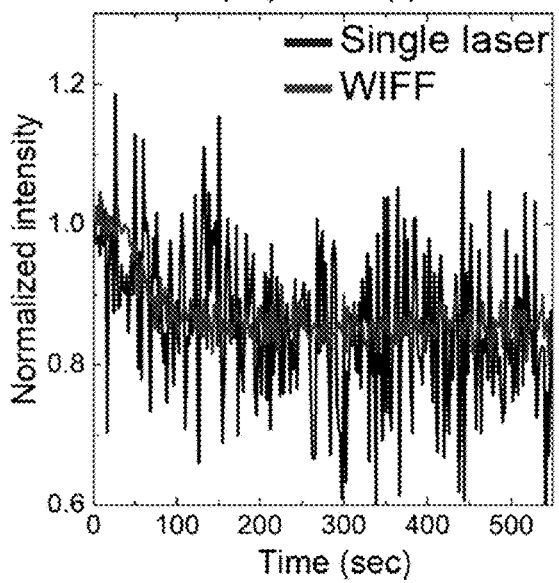
Figure 3C:
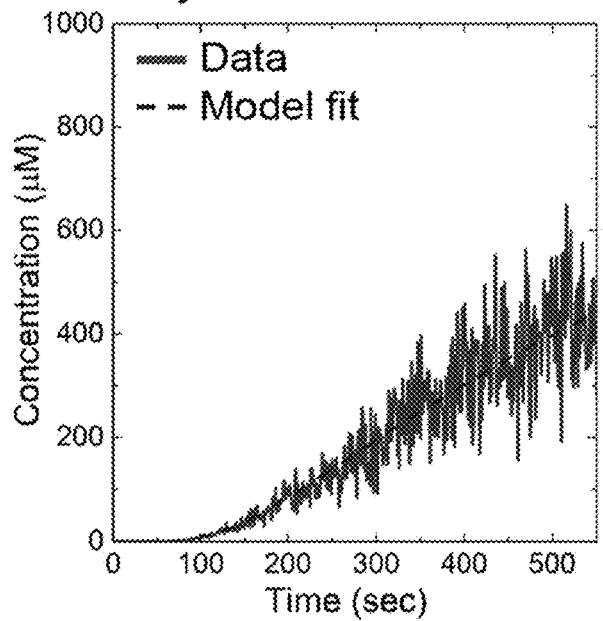
Figure 3D:
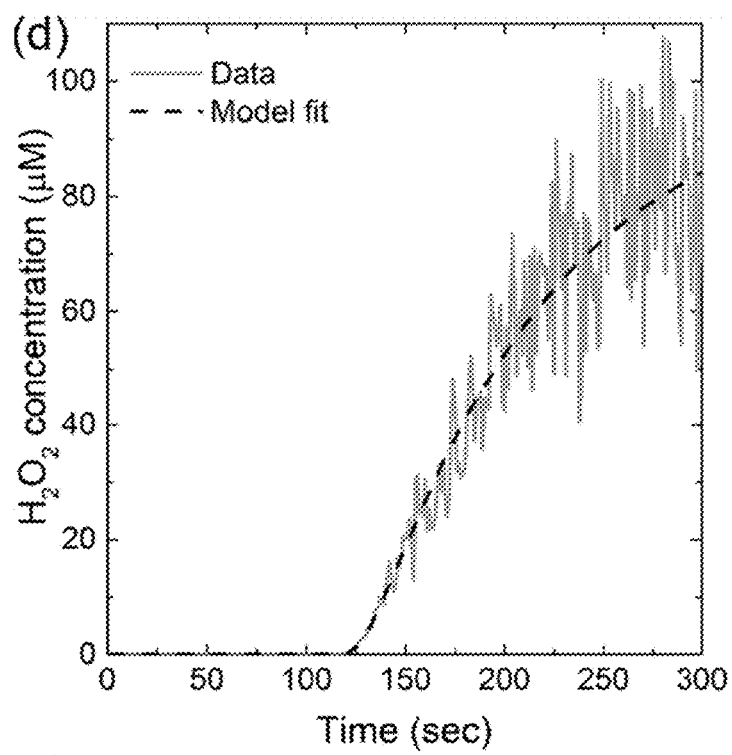
Figure 3E:
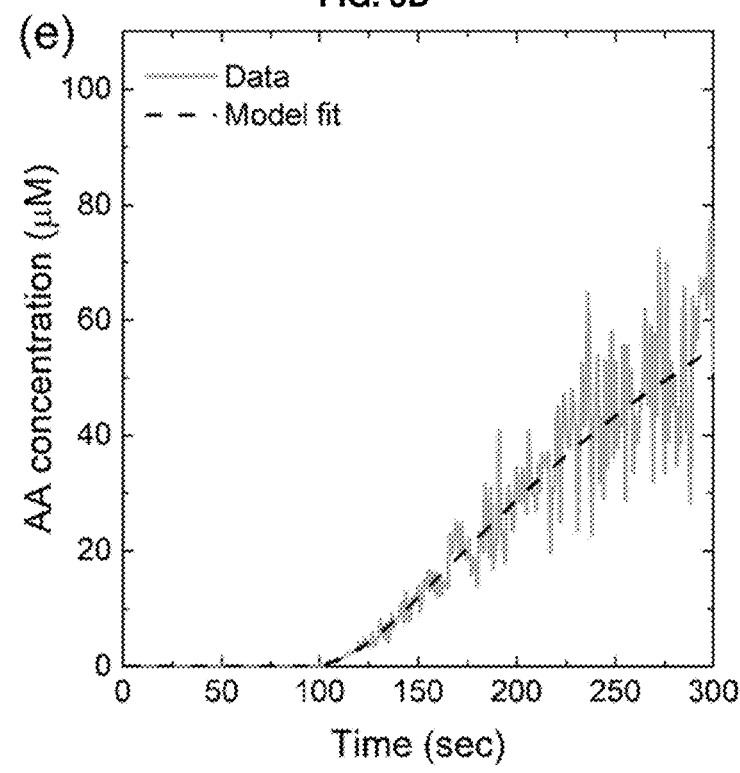
Figure 17:
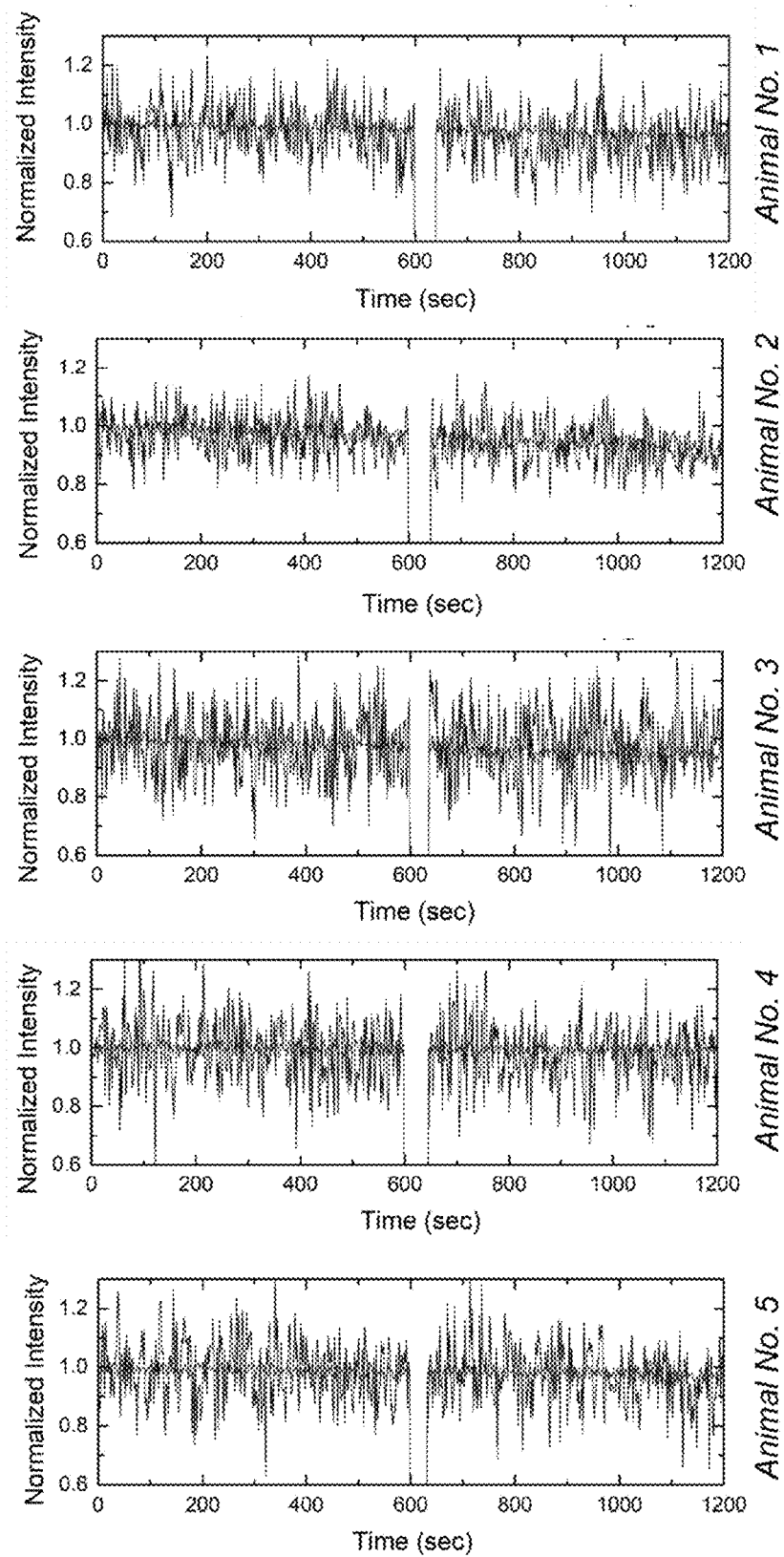
FIG. 17 depicts control experiments with preserved fetal pigs. Normalized intensities for a single laser (black) and WIFF (red), corrected for the background signal, show no drift above 4% over the course of experiments. Five replicas on biologically independent animals. Sensors ($10 \times 10 \times 2$ mm$^3$ gel with 20 mg/l $(AC)_{15}$-SWNTs)) were implanted into the intraperitoneal space of preserved fetal pigs. Animals were monitored for 600 sec and then an injection of 3 ml of saline was performed through an implanted catheter.
Figure 18A:
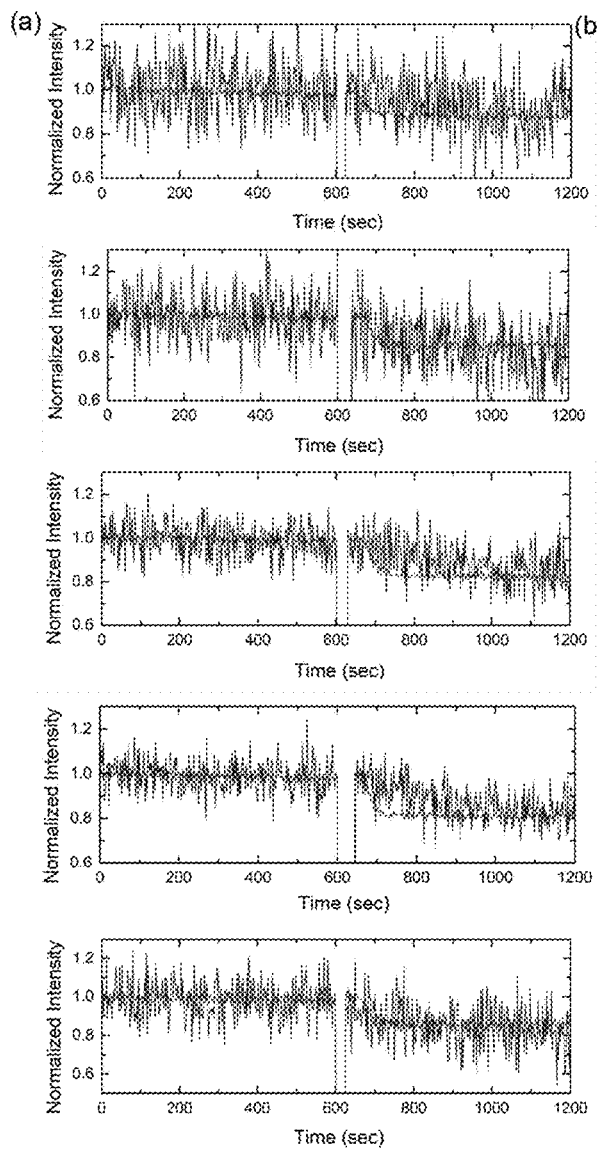
FIGS. 18A-18B depict analyte experiments with preserved fetal pigs.
Figure 18B:
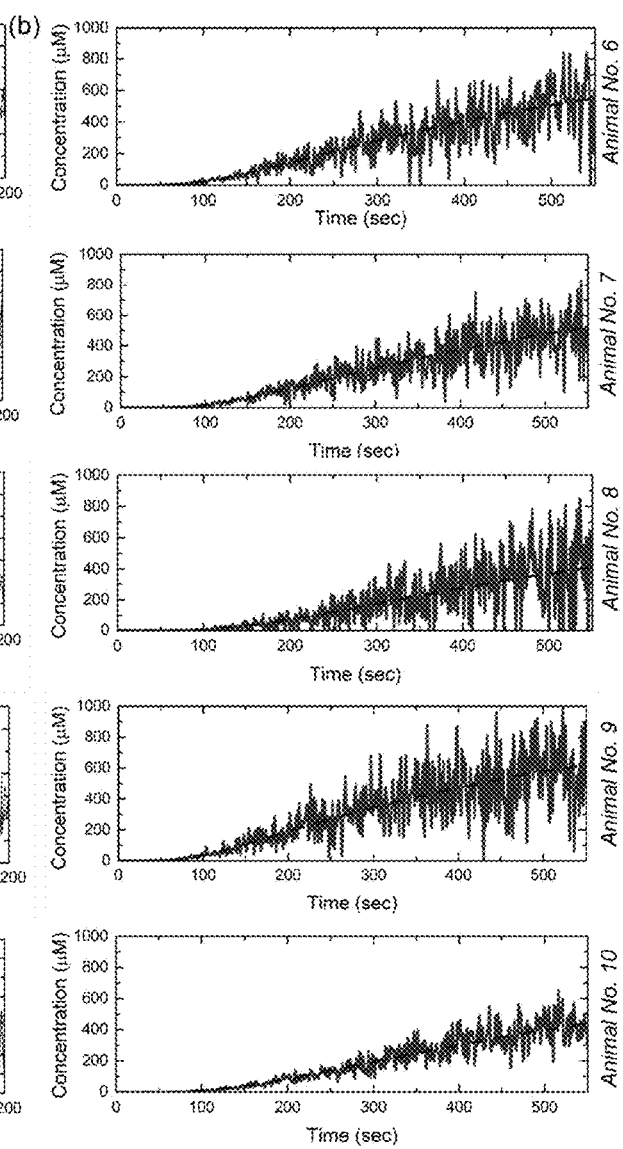
Figure 19A:
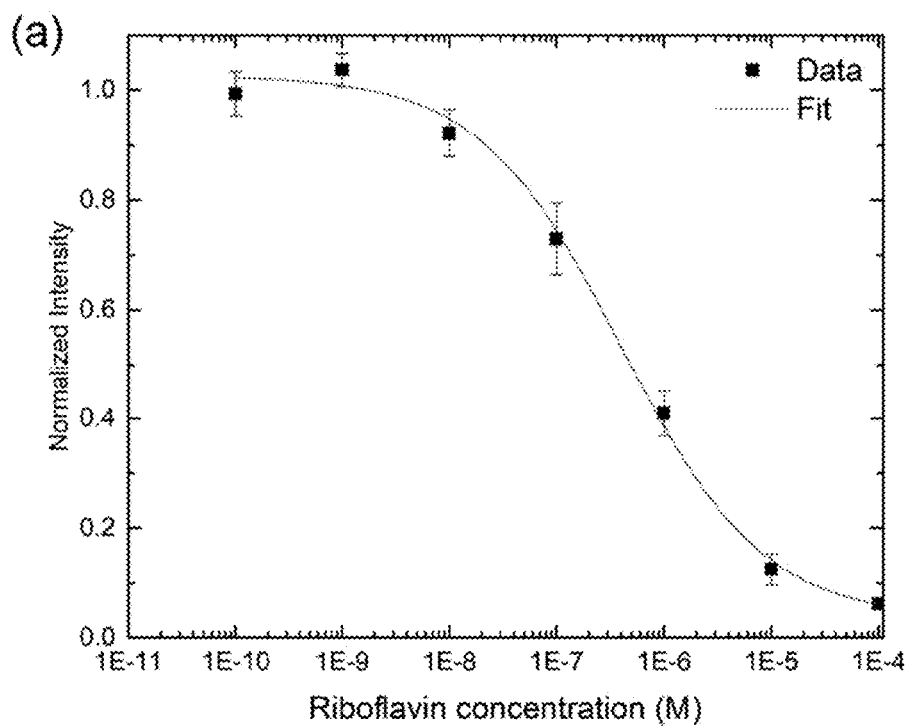
FIGS. 19A-19B depict analyte experiments with preserved fetal pigs.
Figure 19B:
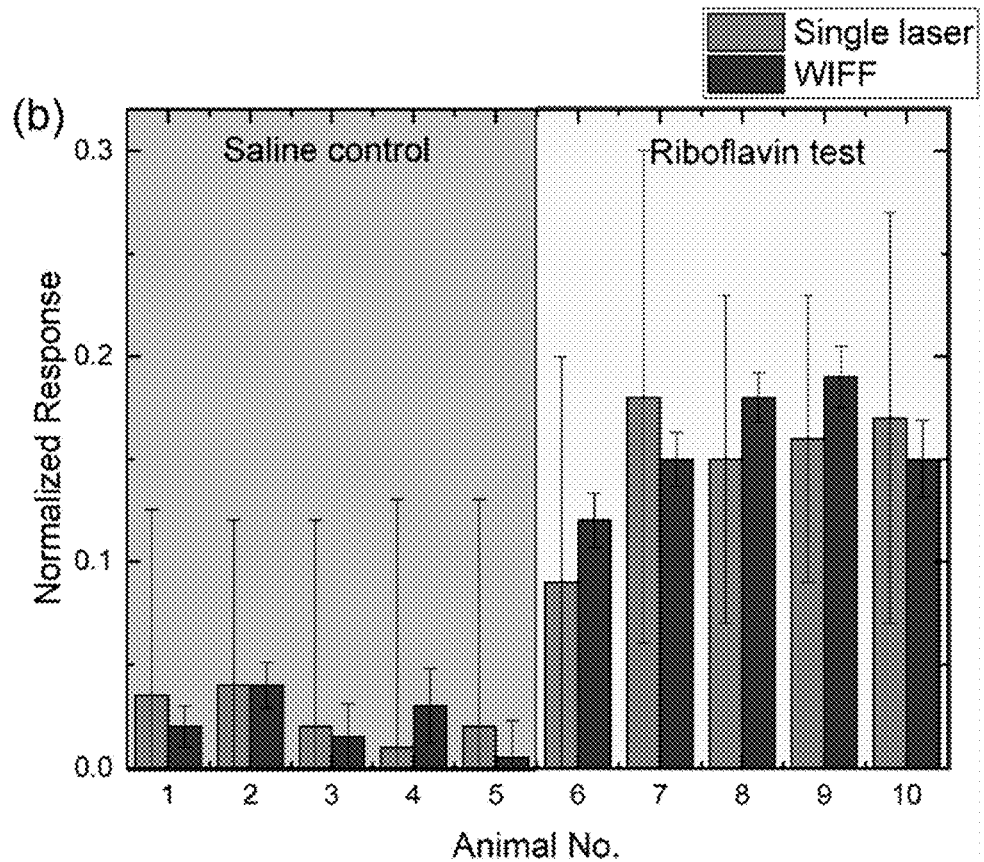
Figure 20A:
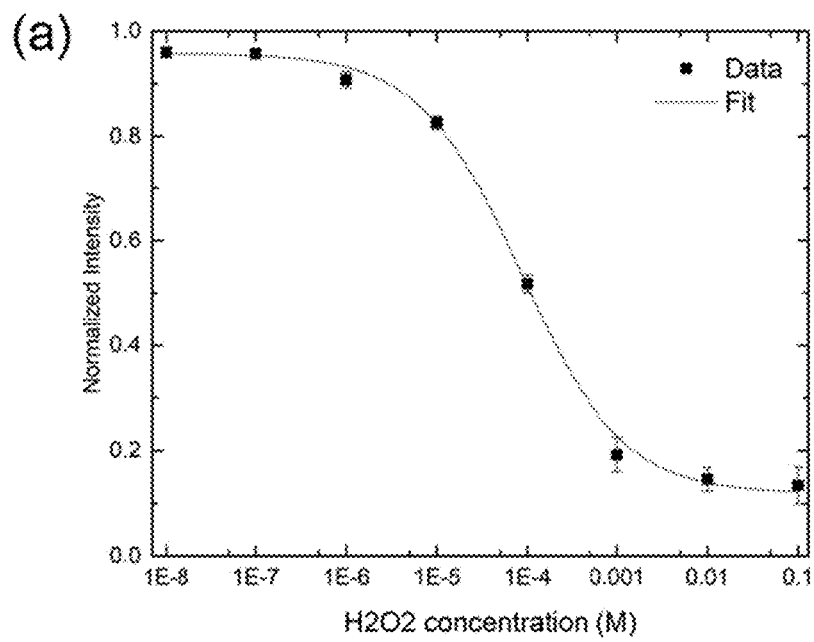
FIGS. 20A-20G depict hydrogen peroxide ($H_2O_2$) sensing.
Figure 20B:
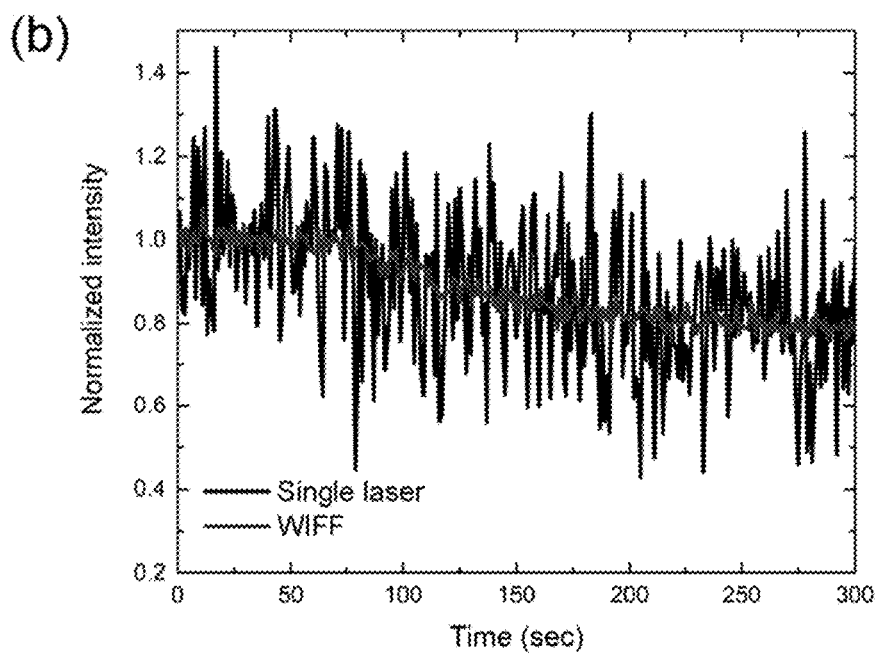
Figure 20C:
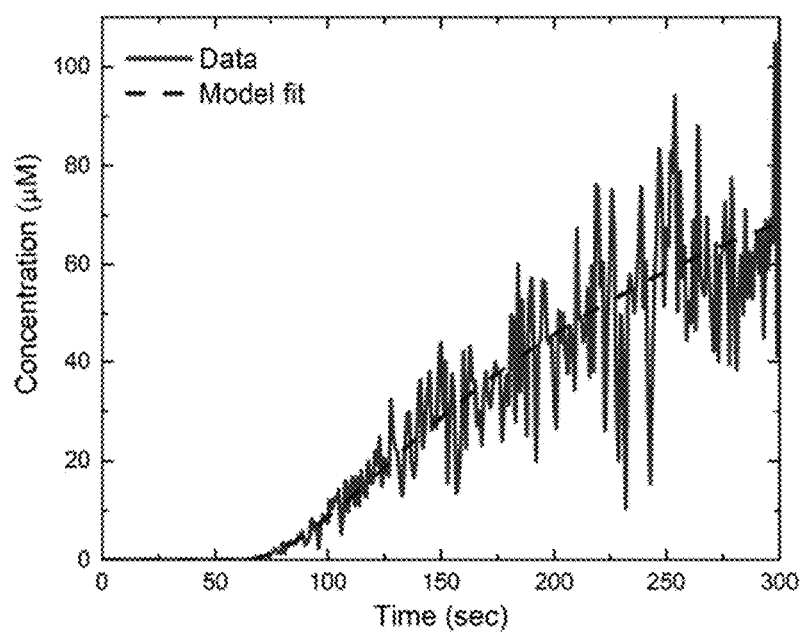
Figure 20D:
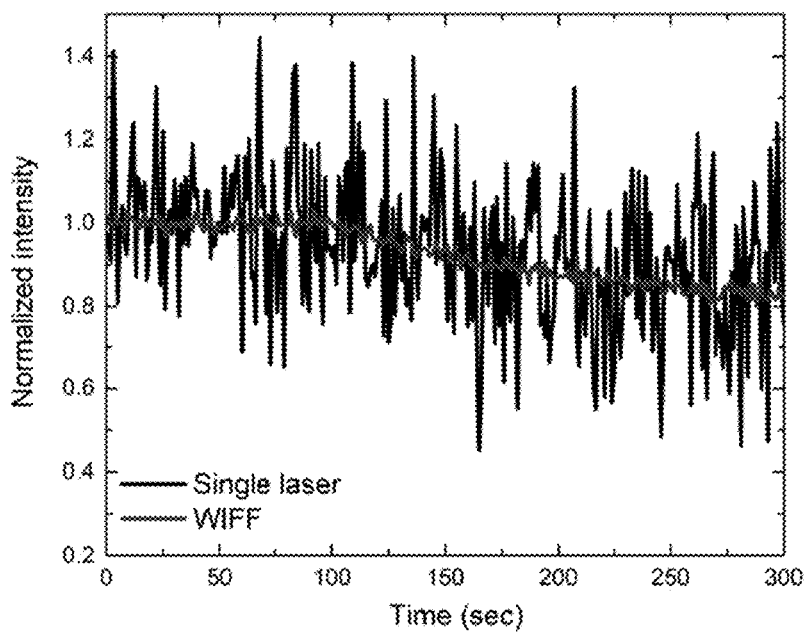
Figure 20E:
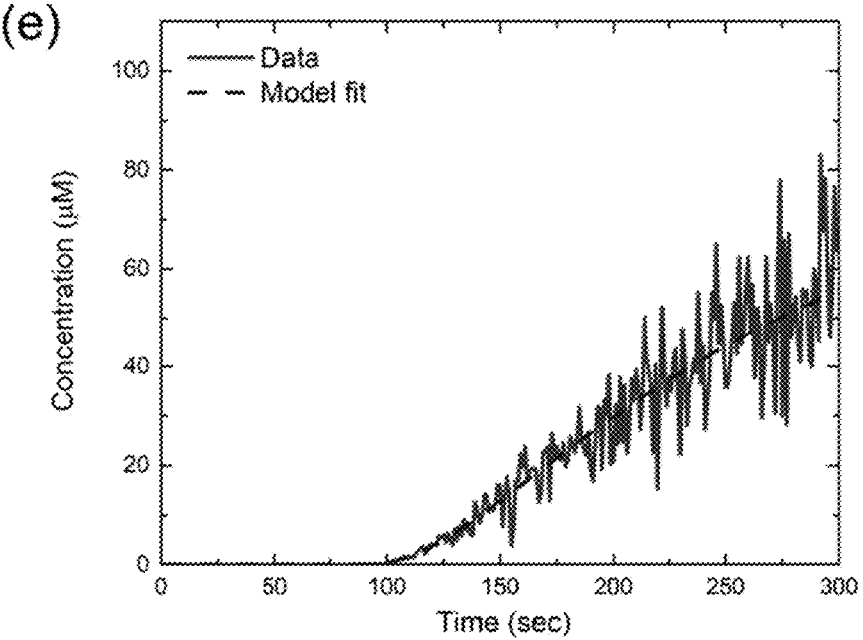
Figure 20F:
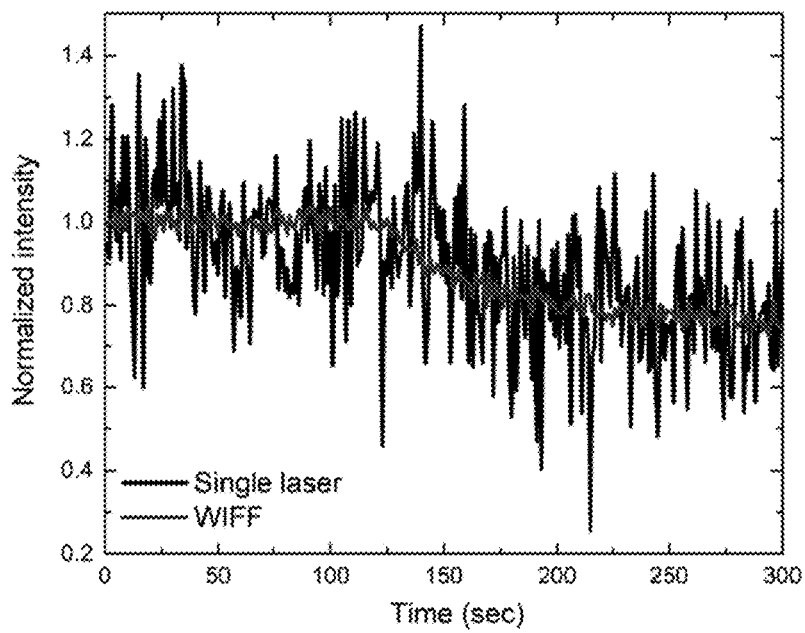
Figure 20G:
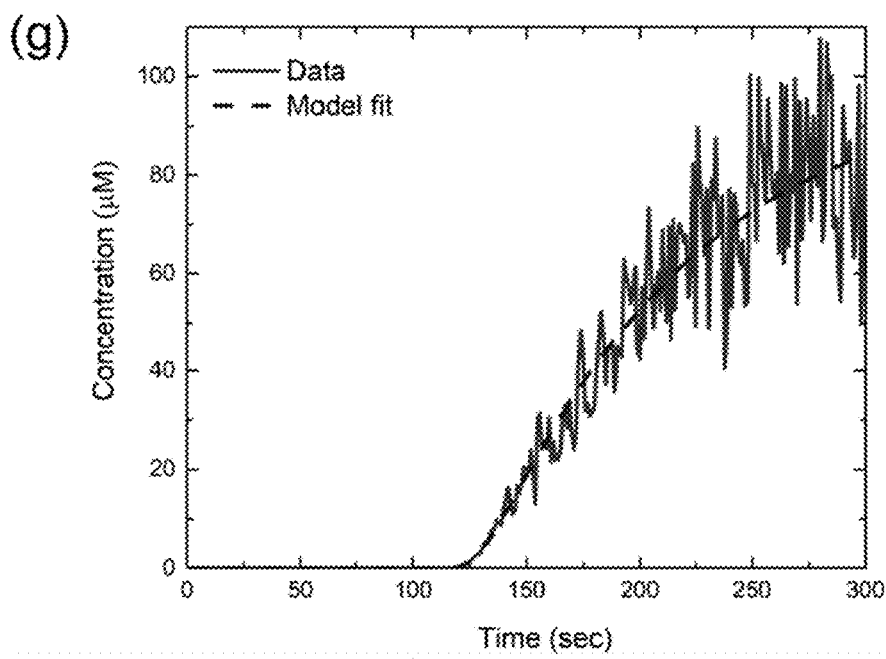
Figure 21A:
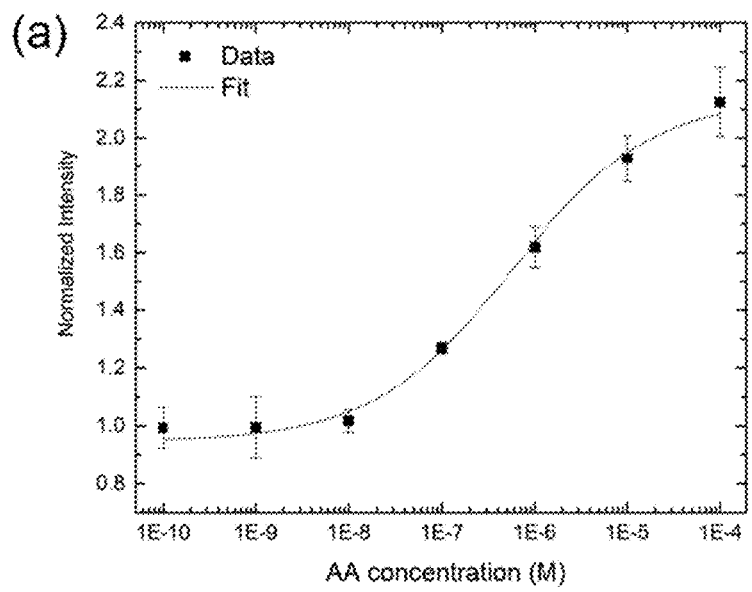
FIGS. 21A-21G depict ascorbic acid (AA) sensing.
Figure 21B:
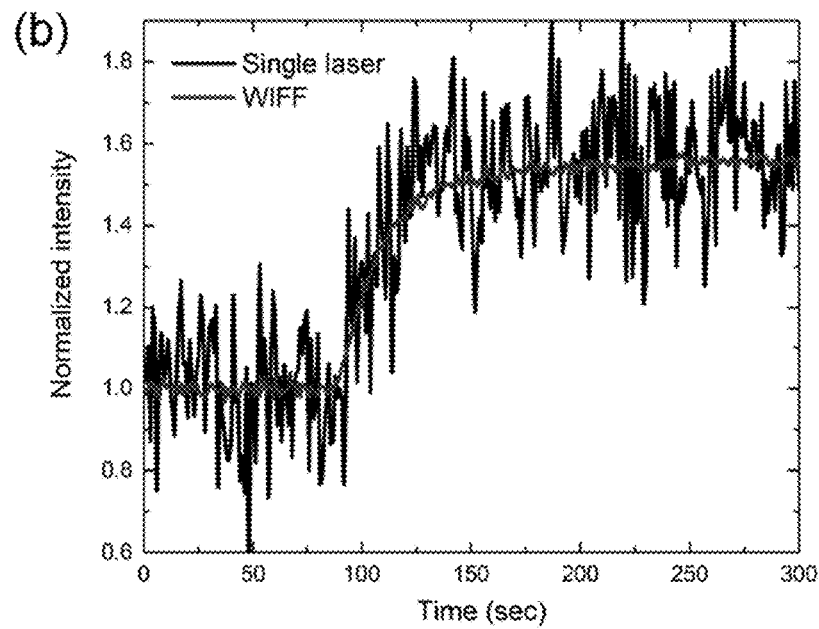
Figure 21C:
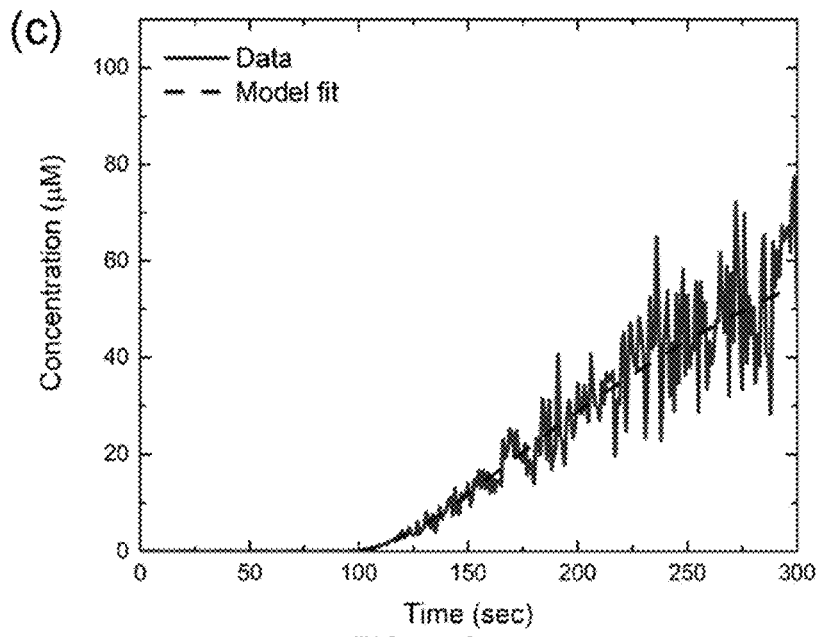
Figure 21D:
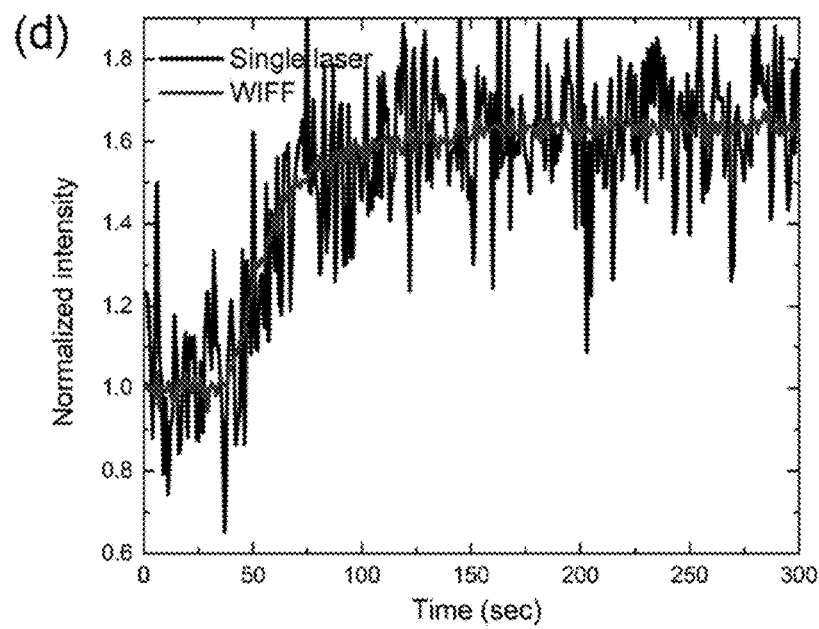
Figure 21E:
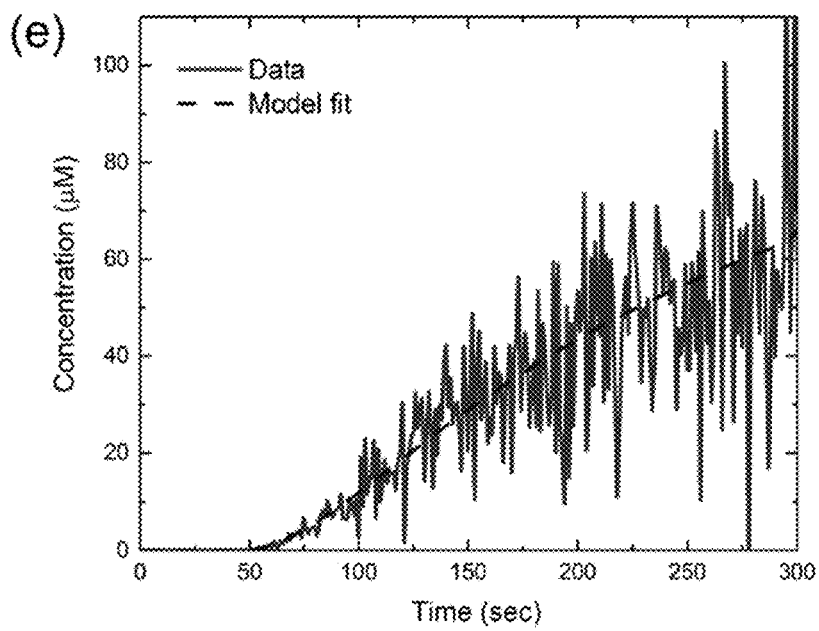
Figure 21F:
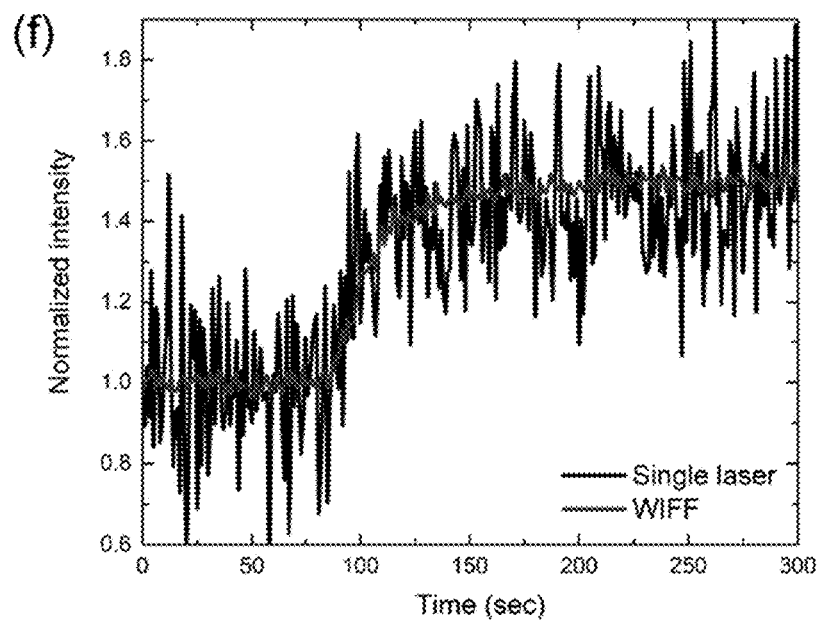
Figure 21G:
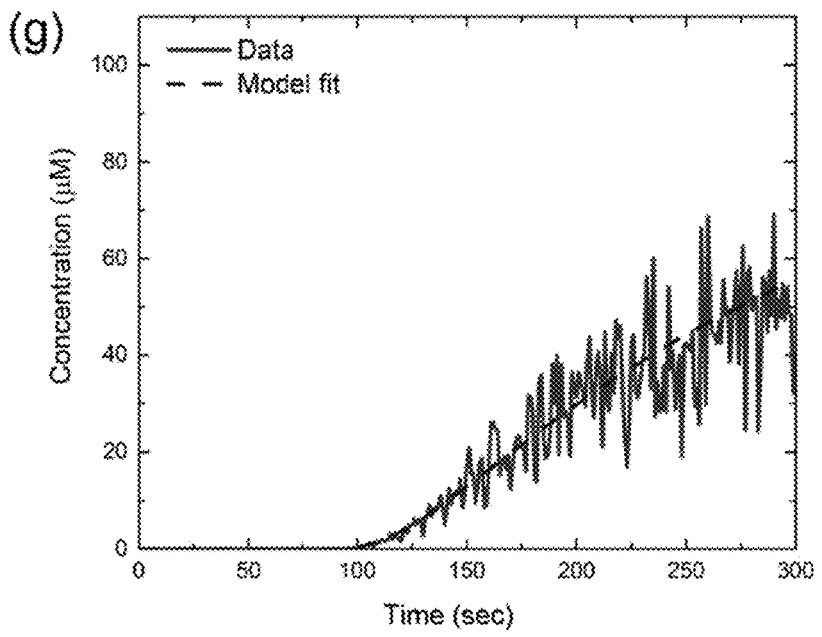

WIFF significantly enhances the SNR of the sensor response to analyte injection even for a 2.3 cm deep implant. Upon a 3 ml injection of 1 mM riboflavin through a catheter implanted in the vicinity of the sensor, WIFF measurements revealed quenching of the 2f-component of the signal, while the time trace of f-component remained invariant (FIG. 3C, panel (i)). Using Eq. (4), WIFF then separates the sensor contribution from that of the background. Prior measurements on specimens without a sensor yield the G factor (Eq. 3) of the tissue to be 0.29±0.01 (in agreement with theoretical predictions). As a result, an 18±1% sensor quenching response was measured at a substantial implant depth of 2.3±0.1 cm (FIG. 3C, panel (ii)) compared to control injections of saline that remained invariant (FIG. 17). Similar results were obtained across n=5 replicas (FIGS. 18A-18B, and FIG. 14) to be further converted into actual riboflavin concentrations (FIG. 3C, panel (iii), see below, Table 1). From the same data set, one can also compare WIFF to a standard fluorescence geometry where excitation is performed by a single laser tuned to the absorption peak of the sensor. Response was measured with large confidence limits being 16±9%, underlining WIFF advantage. Importantly, WIFF represents a general method extendable to a wide range of sensors. For instance, WIFF produced similar results using sensors for $H_2O_2$ (FIG. 3D and FIGS. 20A-20G), an oxidative stress marker and a signaling molecule, and ascorbic acid (FIG. 3E and FIGS. 21A-21G), a vitamin and an essential nutrient. See, for example, V. B. Koman, N. R. von Moos, C. Santschi, V. I. Slaveykova, O. J. F. Martin, New insights into ROS dynamics: a multi-layered microfluidic chip for ecotoxicological studies on aquatic microorganisms, Nanotoxicology 10 (2016) 1041-1050; and D. P. Salem, X. Gong, A. T. Liu, V. B. Koman, J. Dong, M. S. Strano, Ionic Strength-Mediated Phase Transitions of Surface-Adsorbed DNA on Single-Walled Carbon Nanotubes, Journal of the American Chemical Society 139 (2017) 16791-16802, each of which is incorporated by reference in its entirety.

Figure 3F:
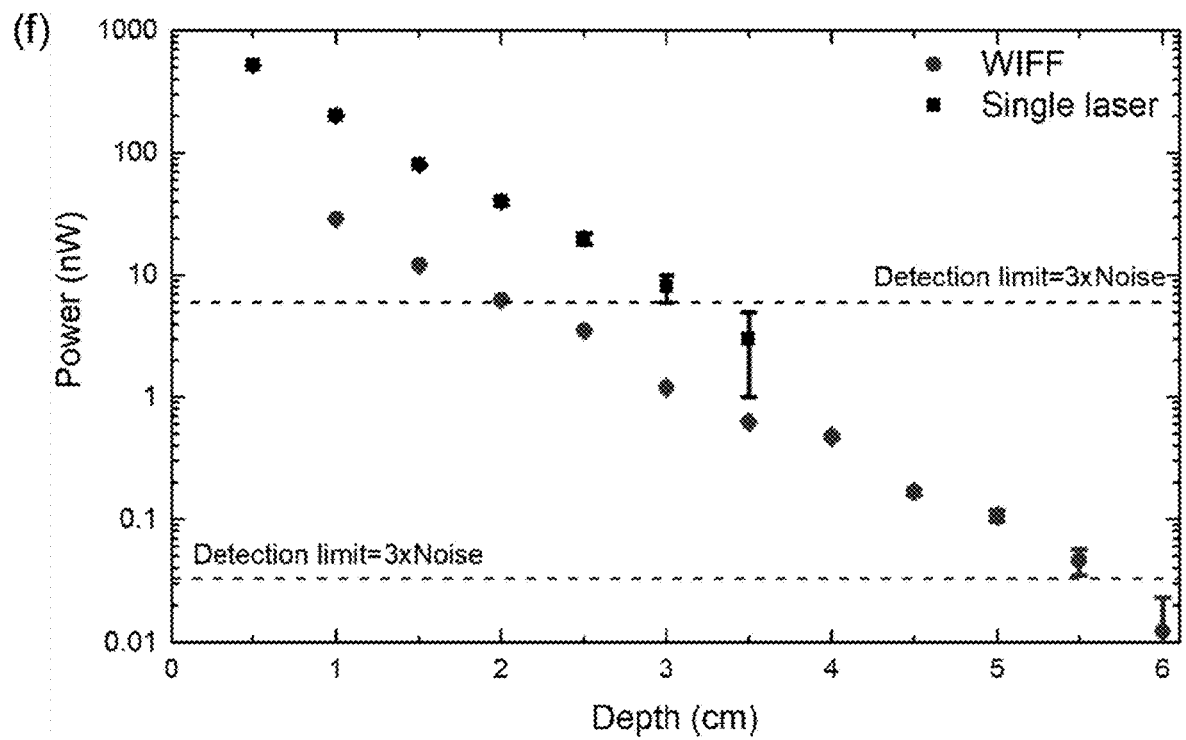
Figure 3G:
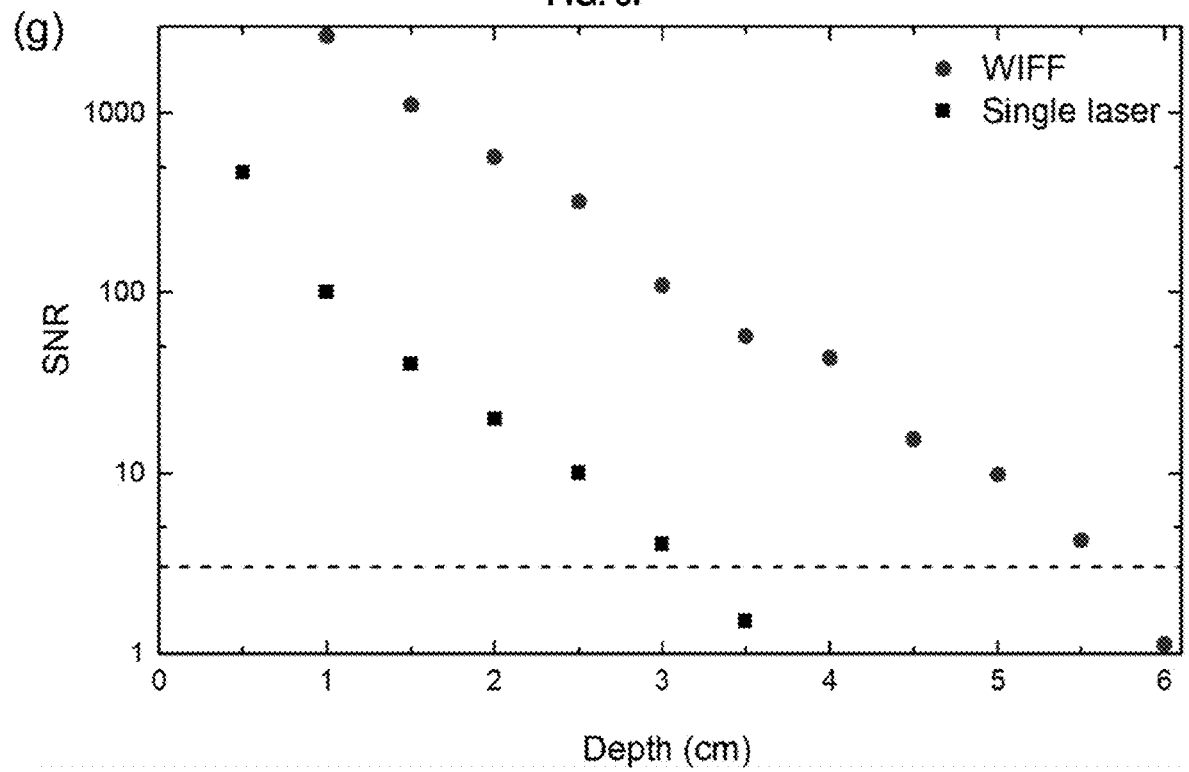
Figure 22A:
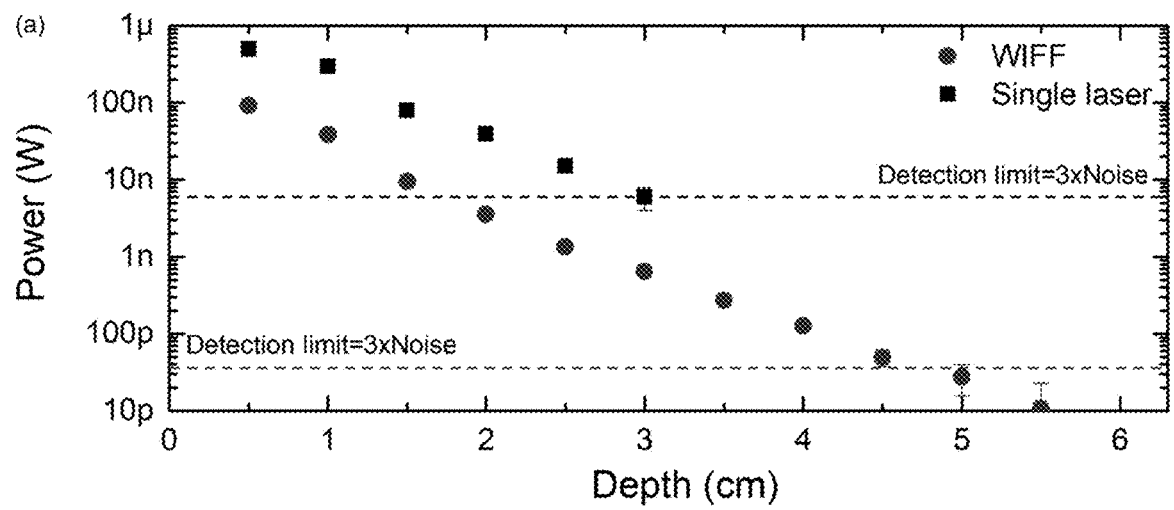
FIGS. 22A-22B depict optical signal detection from the phantom tissue. The signal (FIG. 20A) and SNR (FIG. 20B) of a sensor (5×5×2 mm$^3$ gel with 10 mg/l (GT)$_{15}$-SWNTs) implanted at various depth into a phantom tissue that mimics a mouse brain (n=5). Although WIFF decreases signal intensity ~6.5, it also dramatically reduces the measurement error, allowing to extend the detection range to 4.8 cm depth. Light excitation 730 nm, emission collection >1100 nm. WIFF is performed at the central wavelength of 730 nm with 50 nm modulation width. Dashed lines correspond to SNR of 3.
Figure 22B:
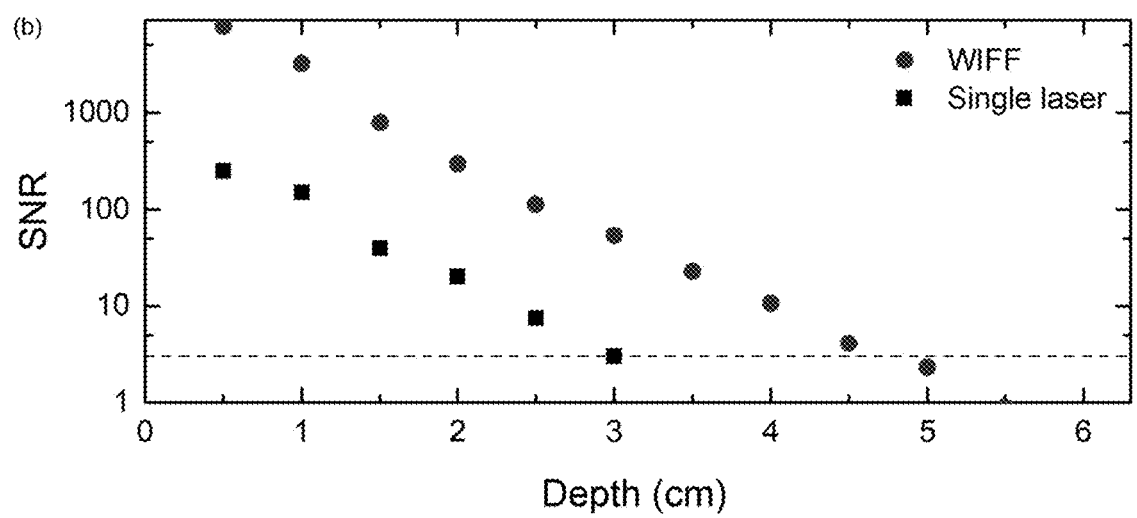
Figure 23:
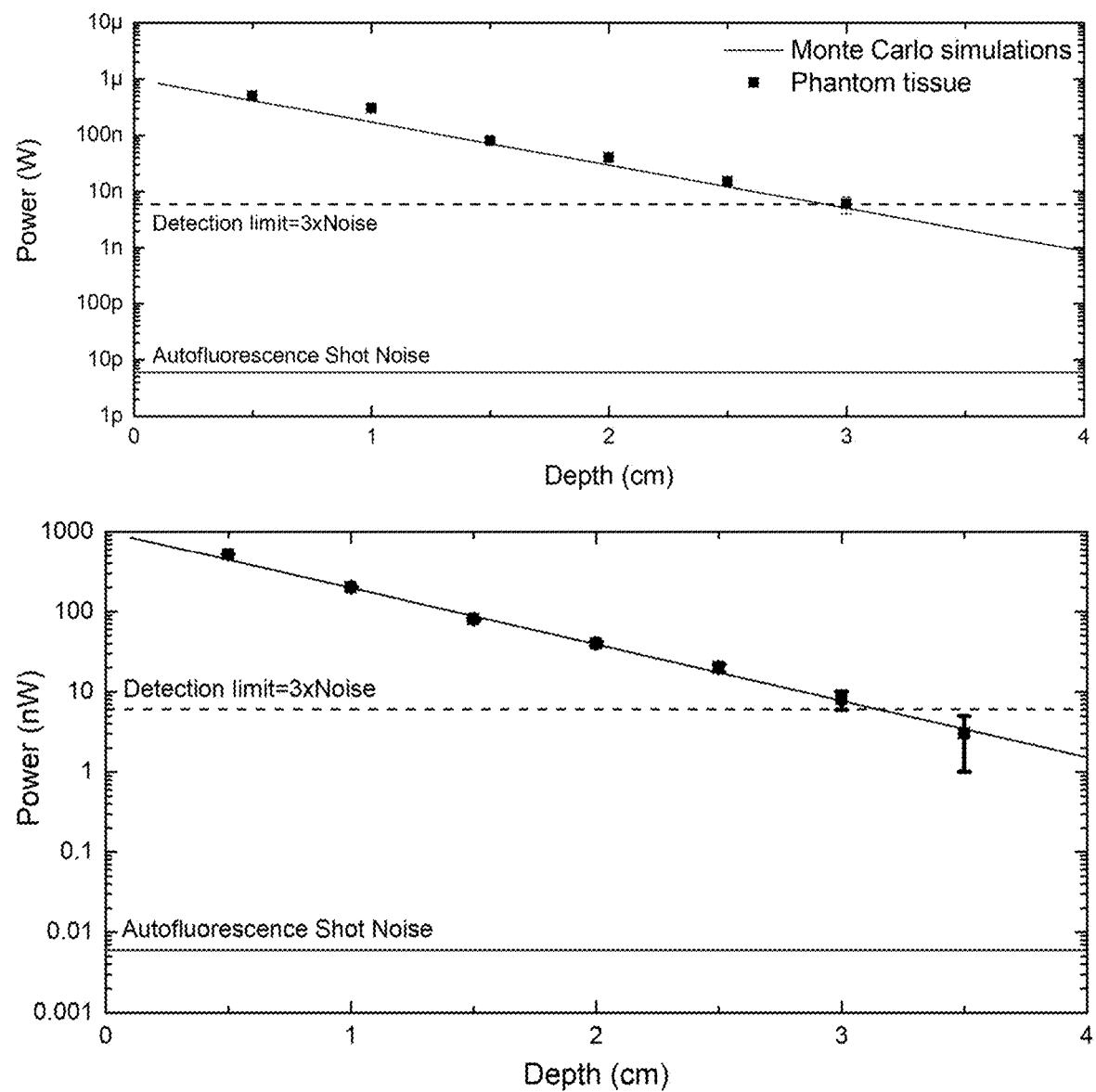

Significantly reducing noise levels, WIFF allows detecting implant signals from several centimeters deep—thicknesses comparable to those needed to monitor biochemical environments in multiple organs of the human body. See, for example, N. M. Iverson, P. W. Barone, M. Shandell, L. J. Trudel, S. Sen, F. Sen, V. Ivanov, E. Atolia, E. Farias, T. P. McNicholas, N. Reuel, N. M. A. Parry, G. N. Wogan, M. S. Strano, In vivo biosensing via tissue-localizable near-infrared-fluorescent single-walled carbon nanotubes, Nature Nanotechnology 8 (2013) 873, which is incorporated by reference in its entirety. To illustrate, WIFF was applied to sensors implanted at different depths into chicken breast tissue (FIG. 3F) and phantom tissue (FIGS. 22A-22B). Single laser measurements demonstrate that the signal drops exponentially with an attenuation coefficient of 1.62 cm$^{-1}$ (1.76 cm$^{-1}$) for chicken breast tissue (phantom tissue). Photomigration Monte Carlo simulations of light propagation in the simulated random media were compared with these data, verifying the absence of spurious reflections that would exhibit deviations from the exponential scaling (FIG. 23). At a depth of 3.2 cm (2.9 cm) for chicken breast tissue (phantom tissue), the signal dropped to several nW with SNR being close to 3, reaching the limit of detection. See, for example, H.-P. Loock, P. D. Wentzell, Detection limits of chemical sensors: Applications and misapplications, Sensors and Actuators B: Chemical 173 (2012) 157-163, which is incorporated by reference in its entirety. The application of WIFF reduced noise level by 182 times from 2 nW to 11 pW, approaching the read noise of the detector. This improvement yielded a 27-fold SNR increase over the case of a single laser excitation (FIG. 3G). This SNR boost enabled the ability to pick up sensor signals from extremely deep implants, up to 5.5±0.1 cm in chicken breast and 4.8±0.1 cm in the tissue phantom.

Role of Autofluorescence in WIFF Performance

Figure 4A:
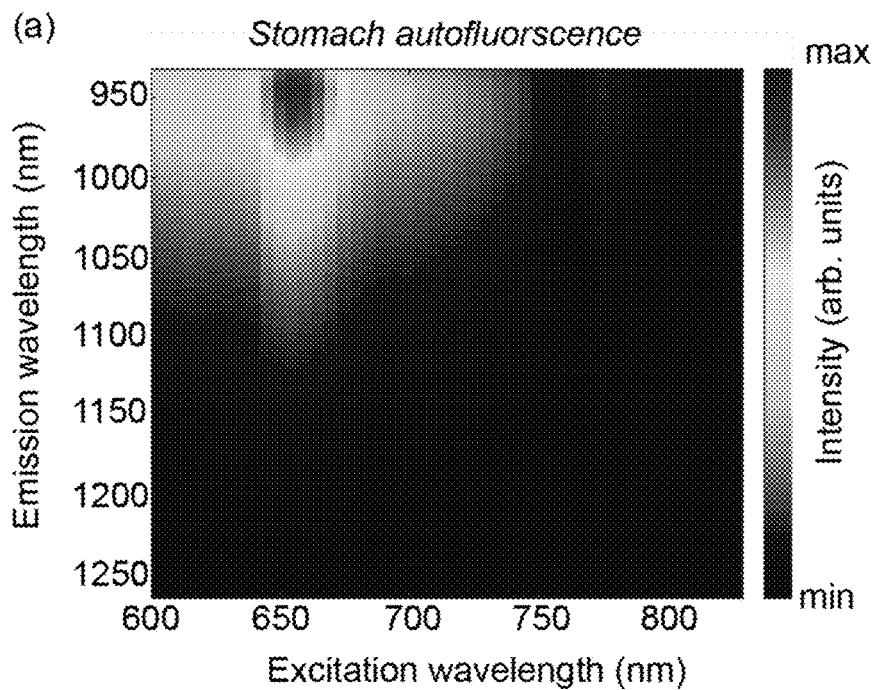
FIGS. 4A-4I depict elucidation of the effect of autofluorescence on WIFF and deep tissue detection.
Figure 4B:
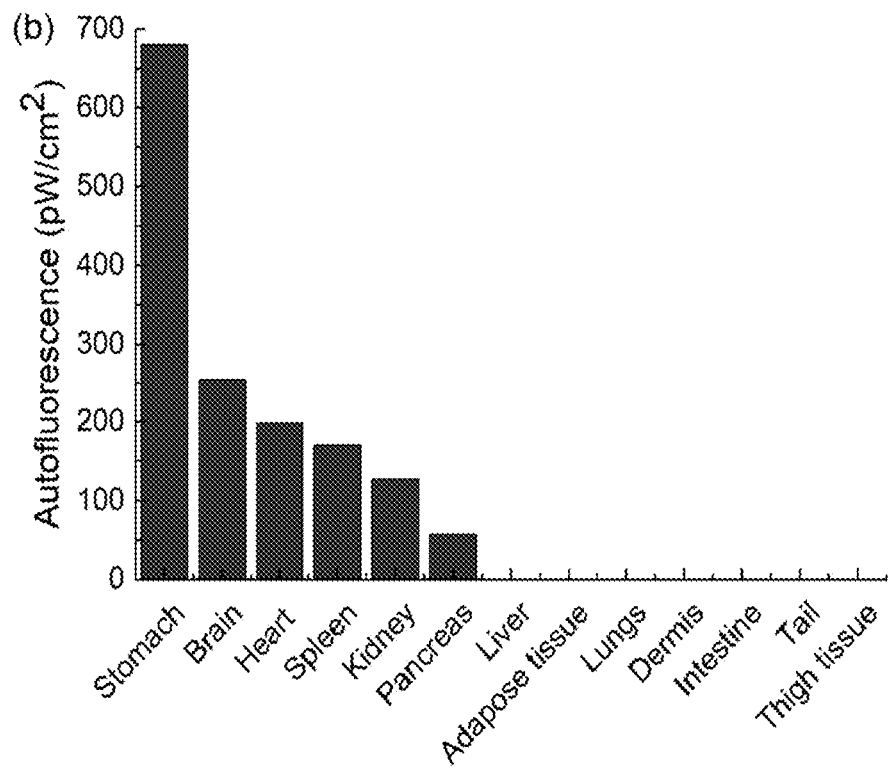
Figure 4C:
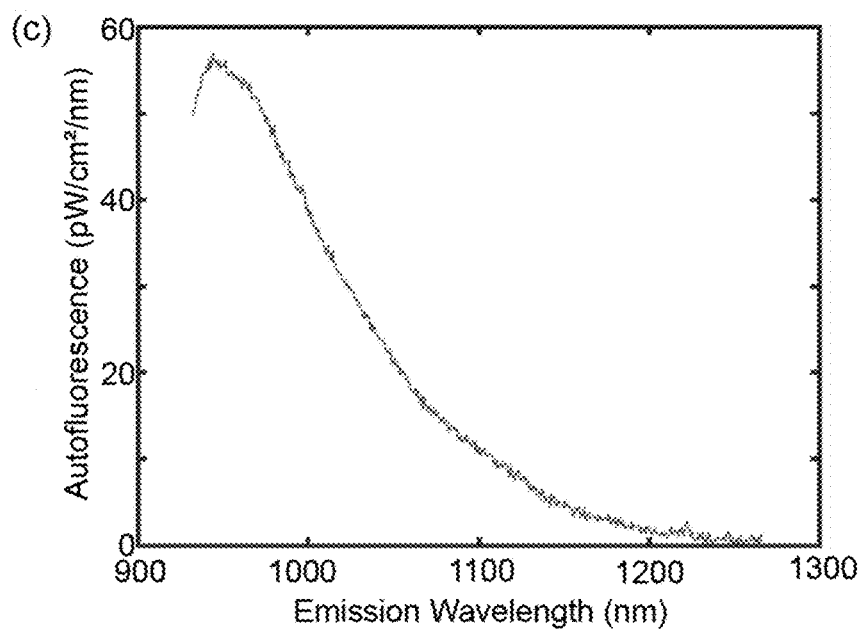
Figure 24:
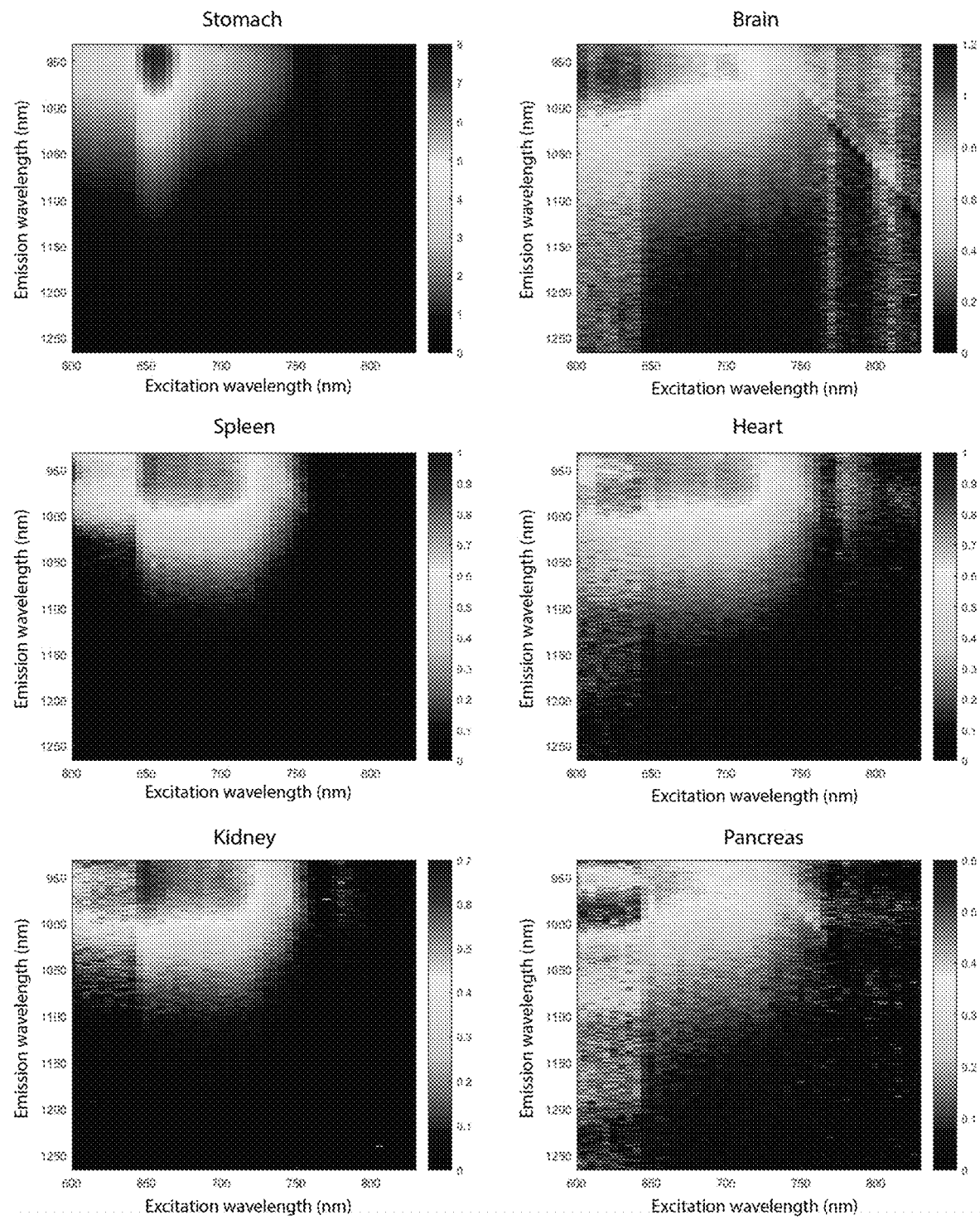
FIG. 24 depicts tissue autofluorescence characterization. Representative excitation-emission maps of various mouse organs. Excitation power was ~1 mW/cm$^2$, integration time 60 sec. Color bars are in arbitrary units that are common across all scans. While chlorophyll dominates spectral features, exact identification remains challenging as a plant-based diet may bring several other components. For the red end of the spectrum, these are azulene, phycocyanin, phycoerythrin, porphyrins, and quinones. See, for example, L. Donaldson, Autofluorescence in Plants, Molecules 25 (2020) 2393, which is incorporated by reference in its entirety. Additionally, several endogenous compounds can also contribute, such as hamatoporphyrin and lipopigments, in this spectral range. See, for example, B. del Rosal, I. Villa, D. Jaque, F. Sanz-Rodríguez, In vivo autofluorescence in the biological windows: the role of pigmentation, Journal of Biophotonics 9 (2016) 1059-1067, which is incorporated by reference in its entirety.
Figure 25:
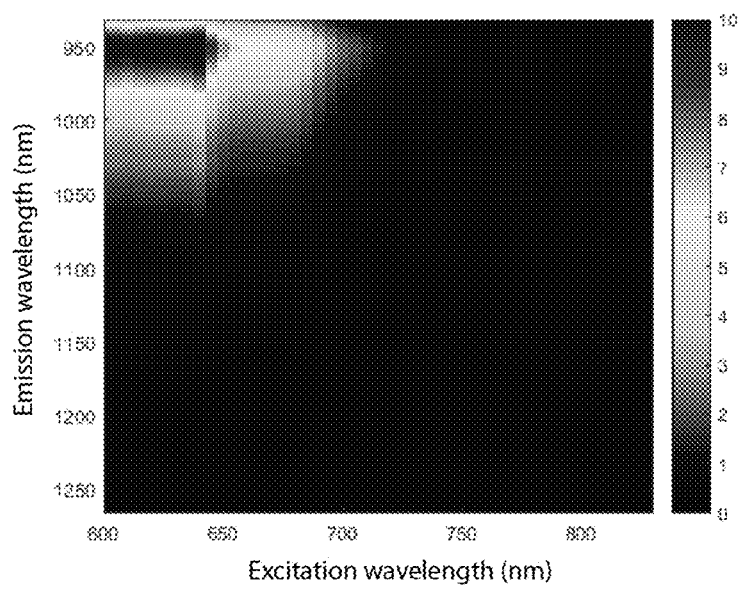
FIG. 25 depicts a chlorophyll excitation map. Excitation-emission map of 9 µg/ml chlorophyll b at the excitation power ~1 mW/cm$^2$. The integration time is 10 sec.
Figure 26A:
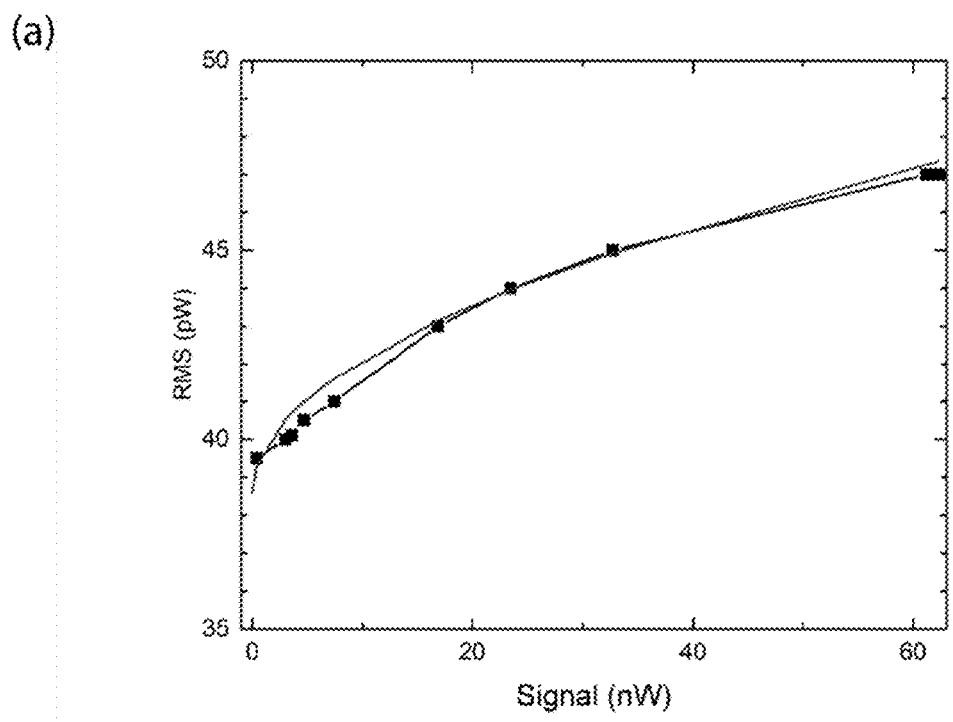
FIGS. 26A-26C depicts noise characterization of the detector and a laser.
Figure 26B:
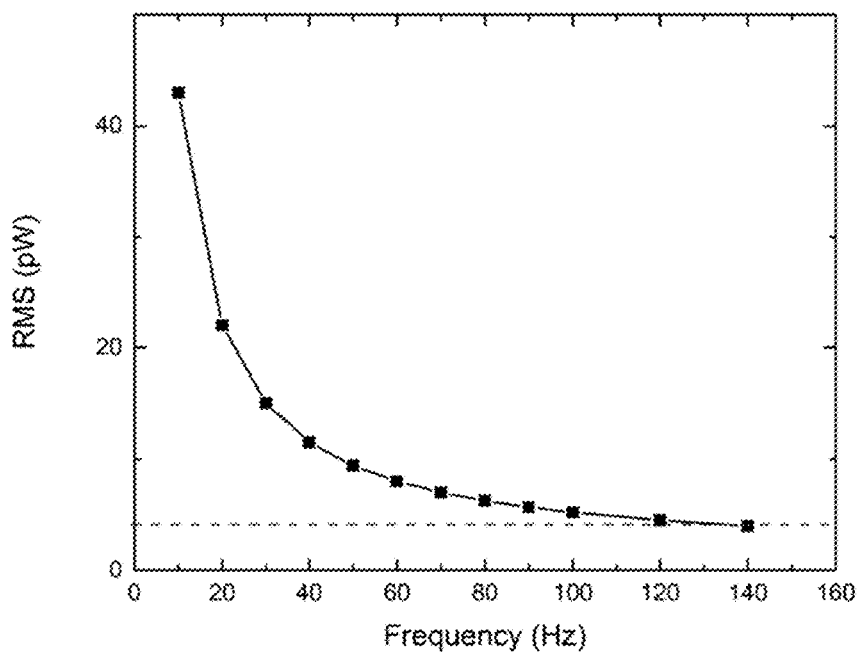
Figure 26C:
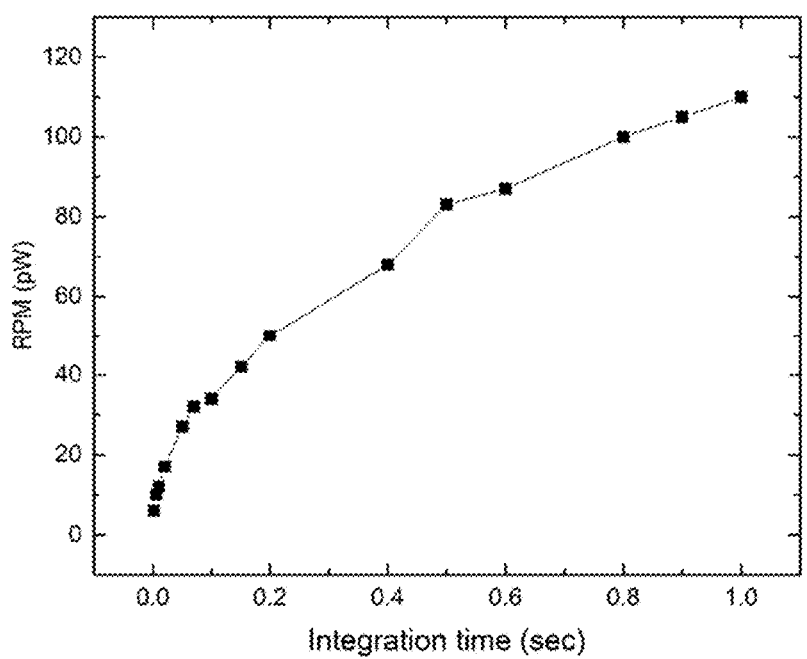
Figure 27A:
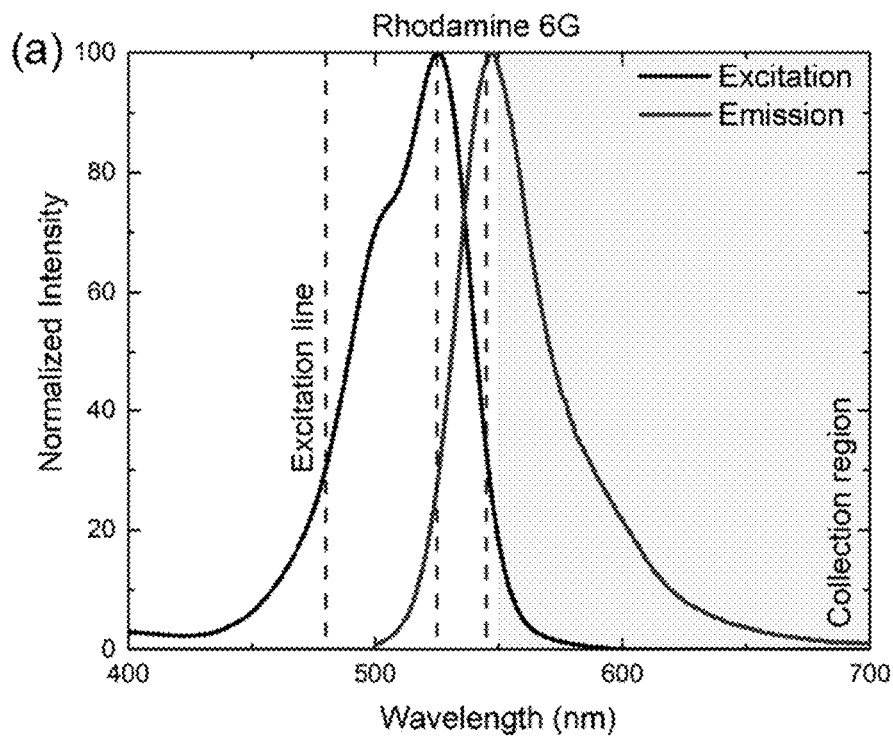
FIGS. 27A-27K depict modulation conditions for fluorescent dyes.
Figure 27B:
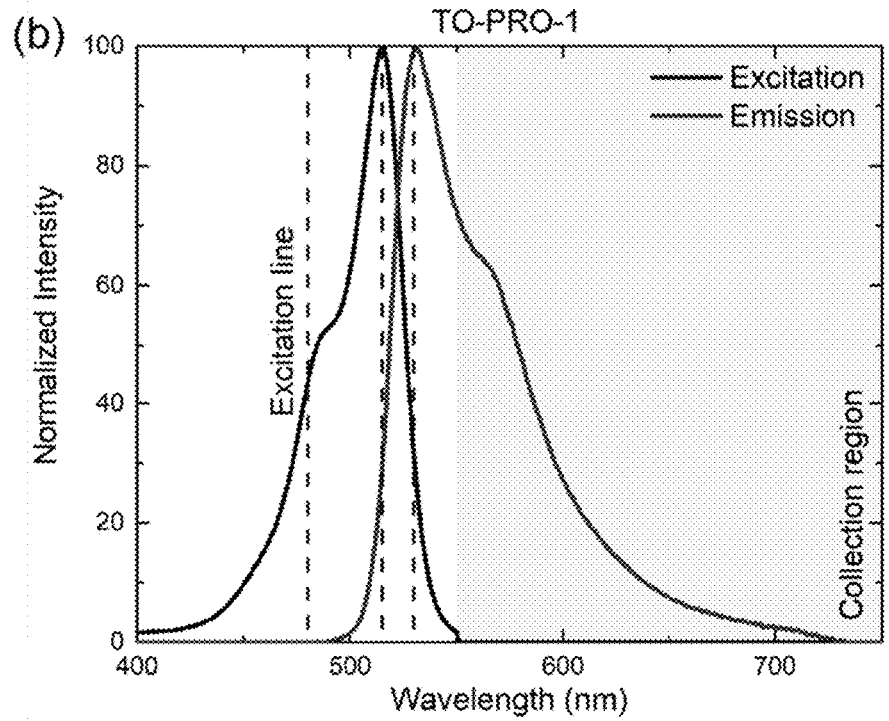
Figure 27C:
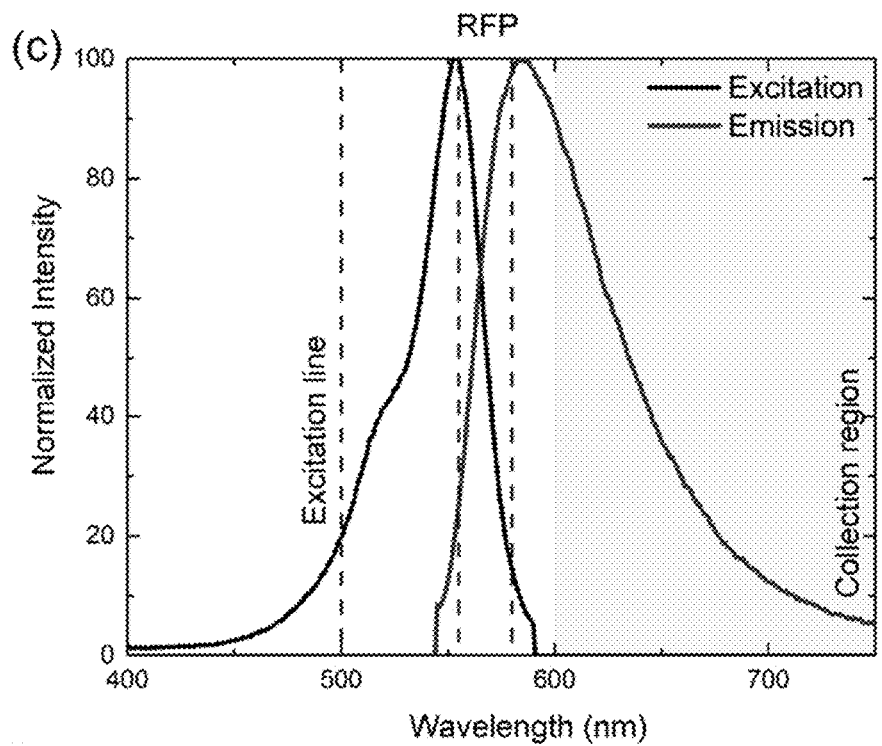
Figure 27D:
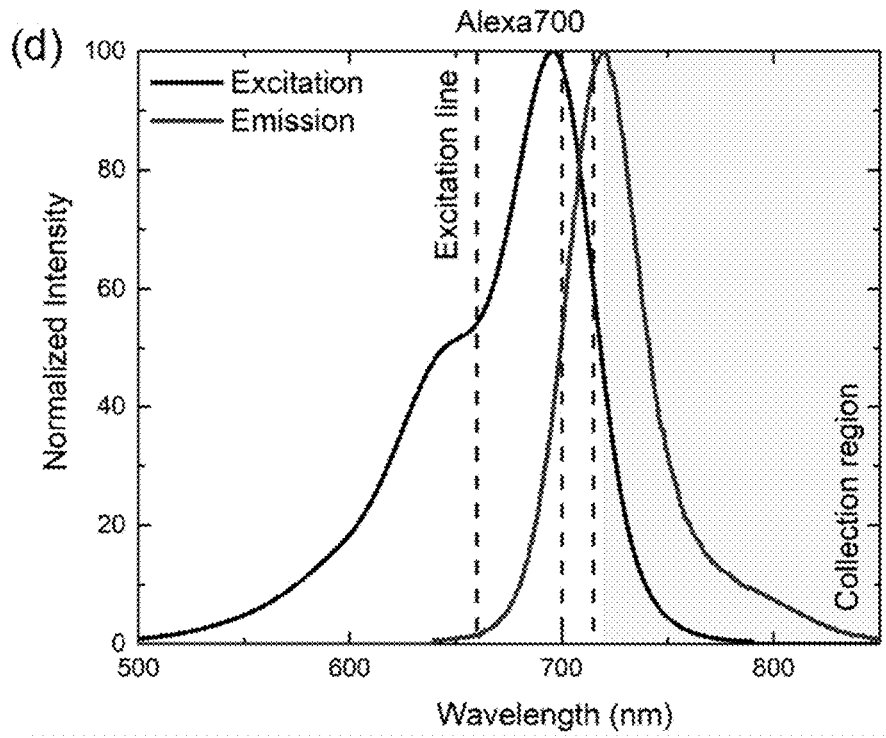
Figure 27E:
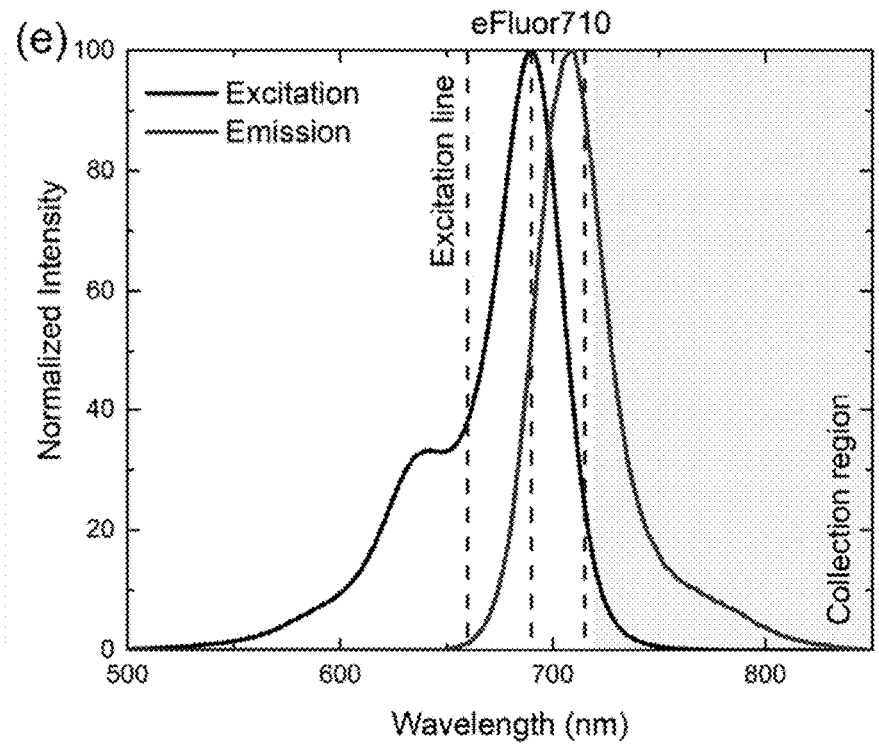
Figure 27F:
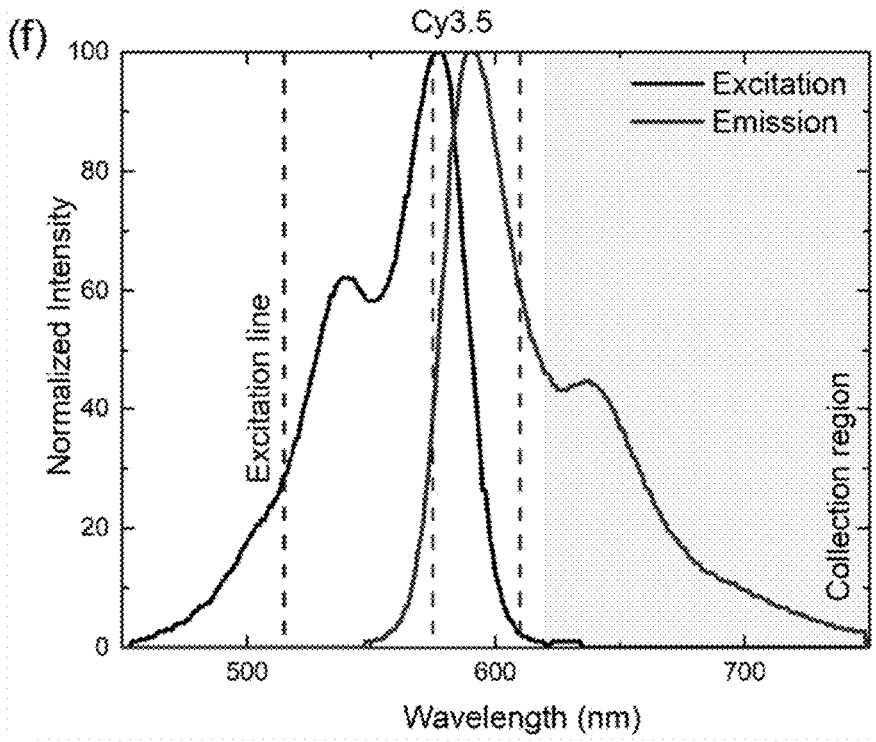
Figure 27G:
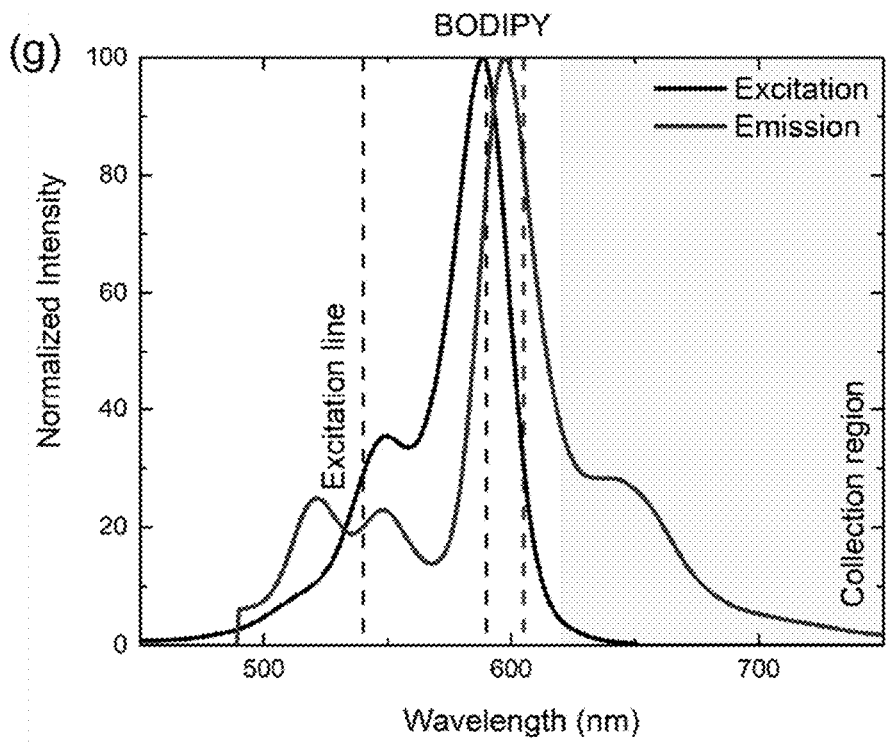
Figure 27H:
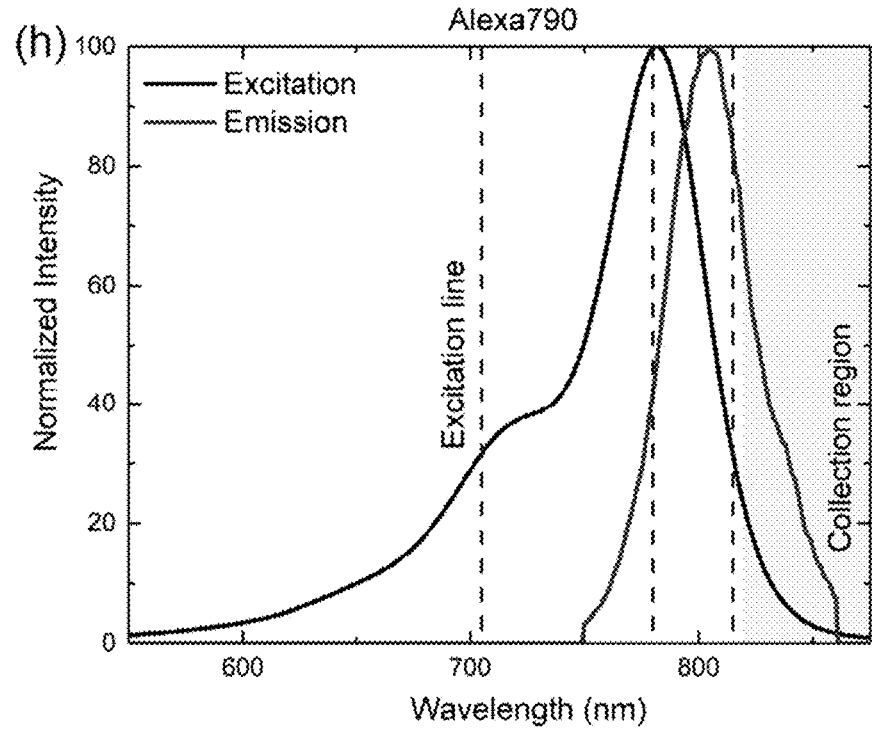
Figure 27I:
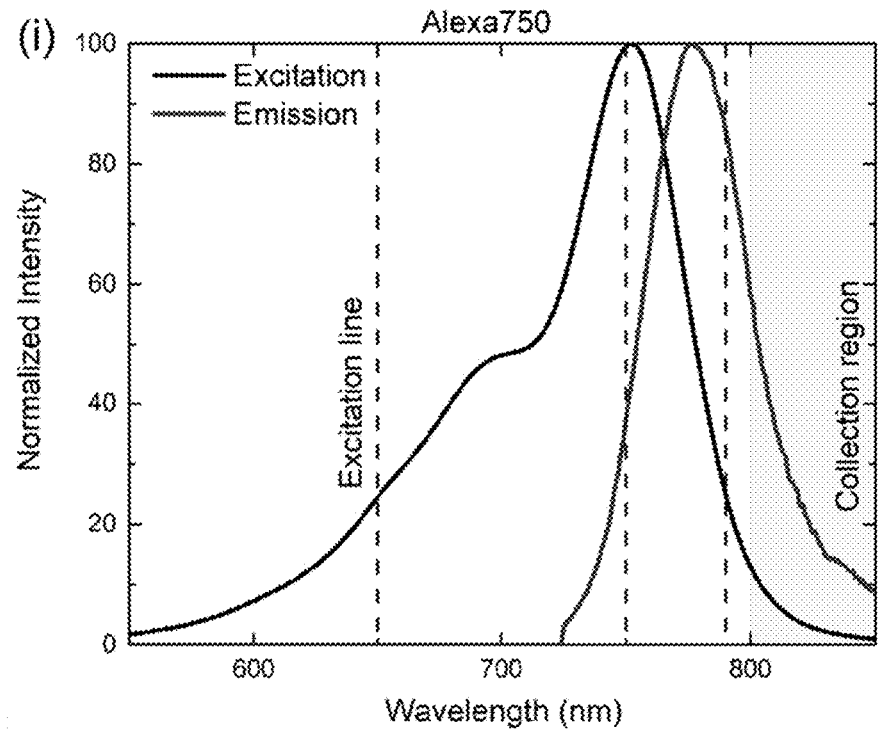
Figure 27J:
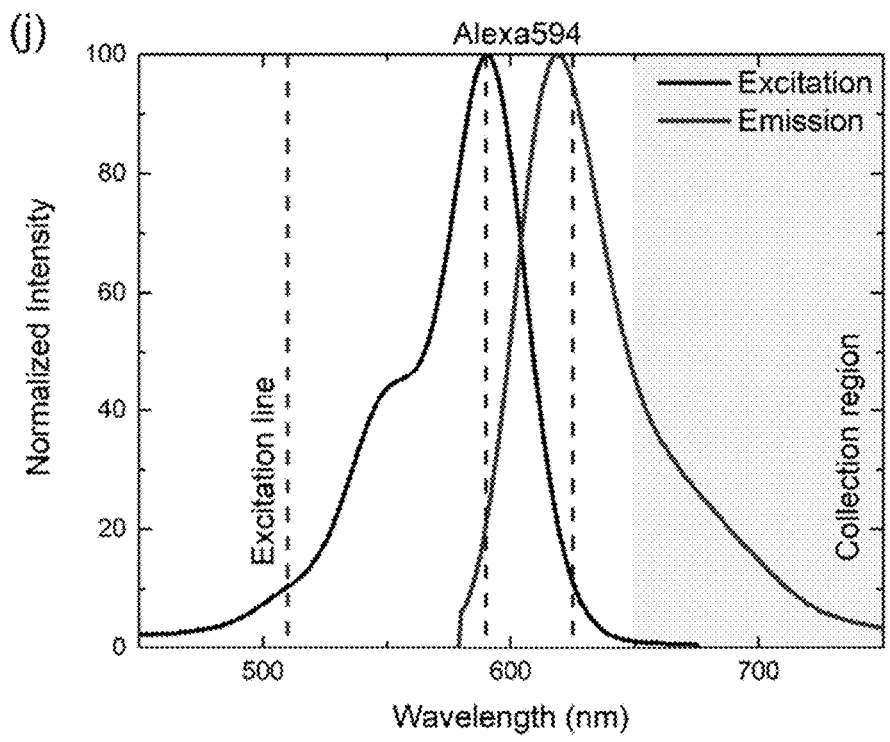
Figure 27K:
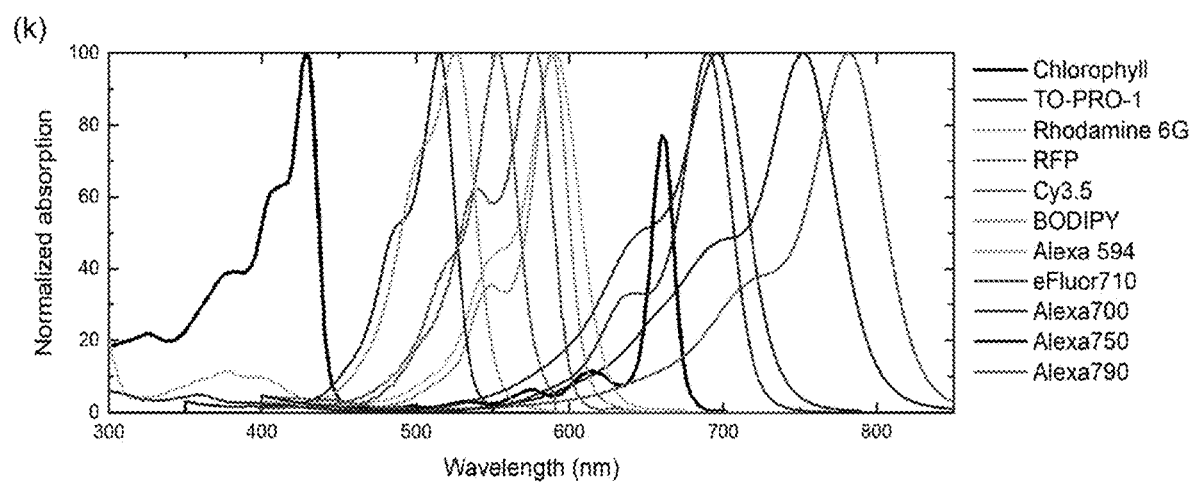
Figure 28A:
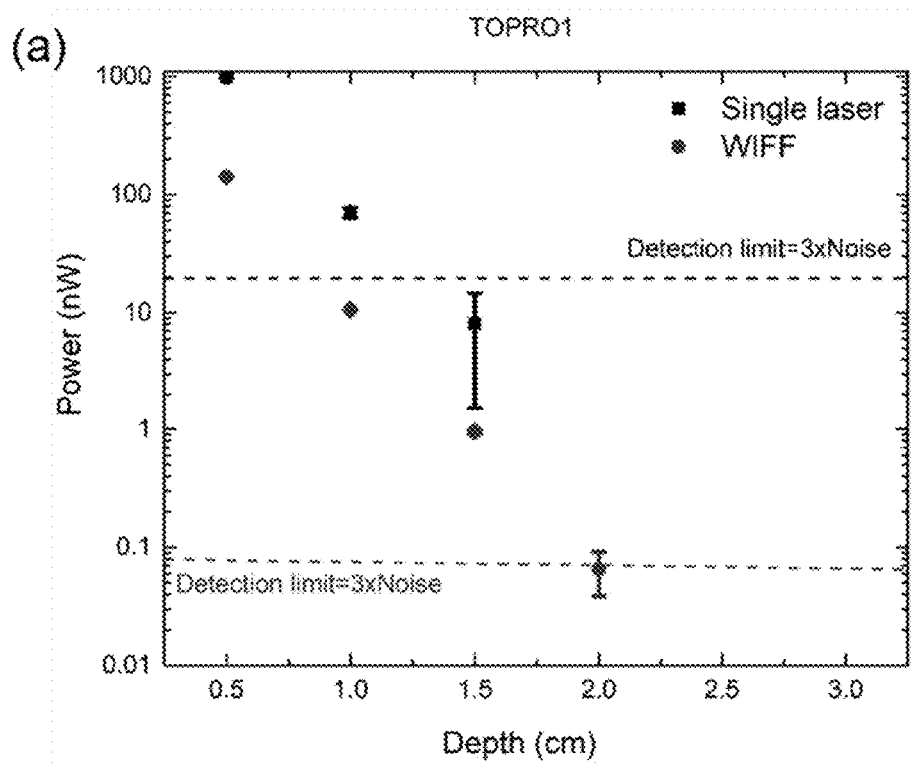
FIGS. 28A-28H depict implantation of fluorescent dyes. Signals of sensors (5×5×2 mm$^3$ chamber) implanted at various depth inside the phantom tissue (n=3): 10 µM of TO-PRO-1 (FIG. 28A), 2 µM of Alexa 700 (FIG. 28B), and 2 µM of Alexa 750 (FIG. 28C) with the extracted SNR values (FIG. 28D) (FIG. 28F), respectively.
Figure 28B:
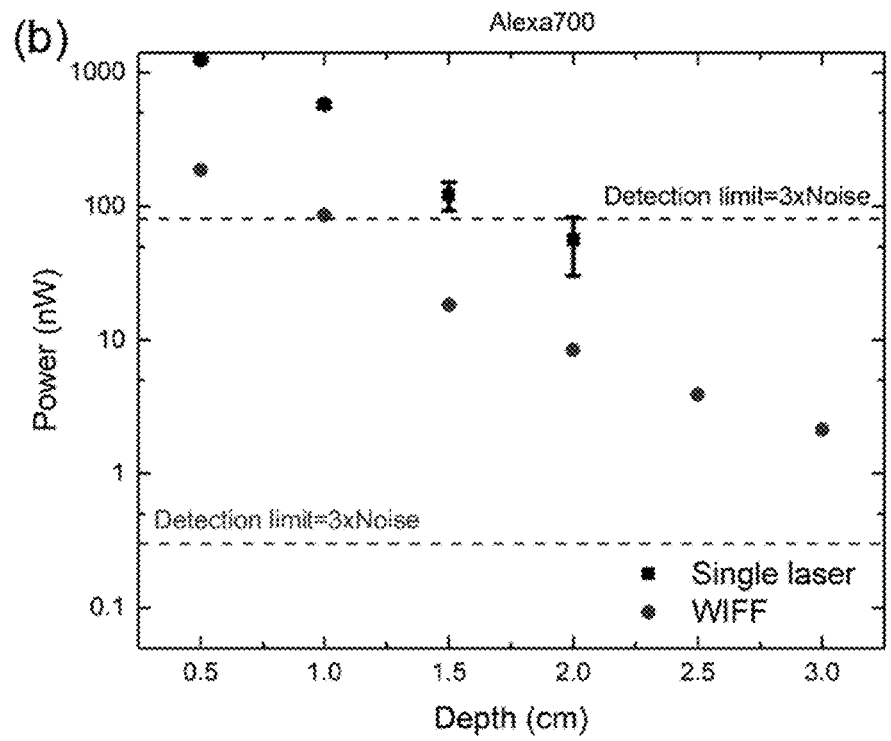
Figure 28C:
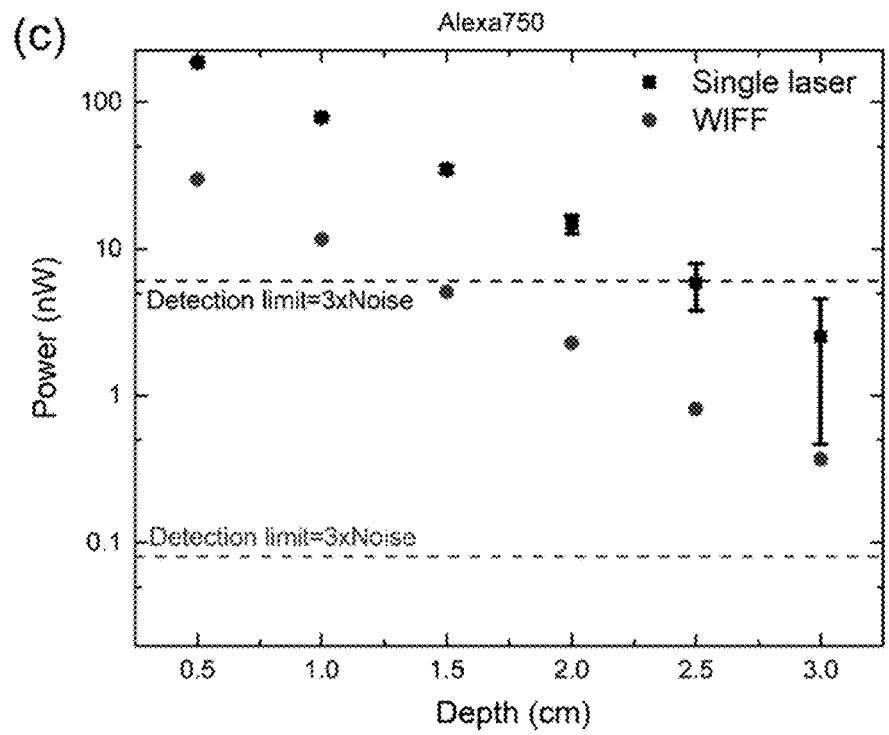
Figure 28D:
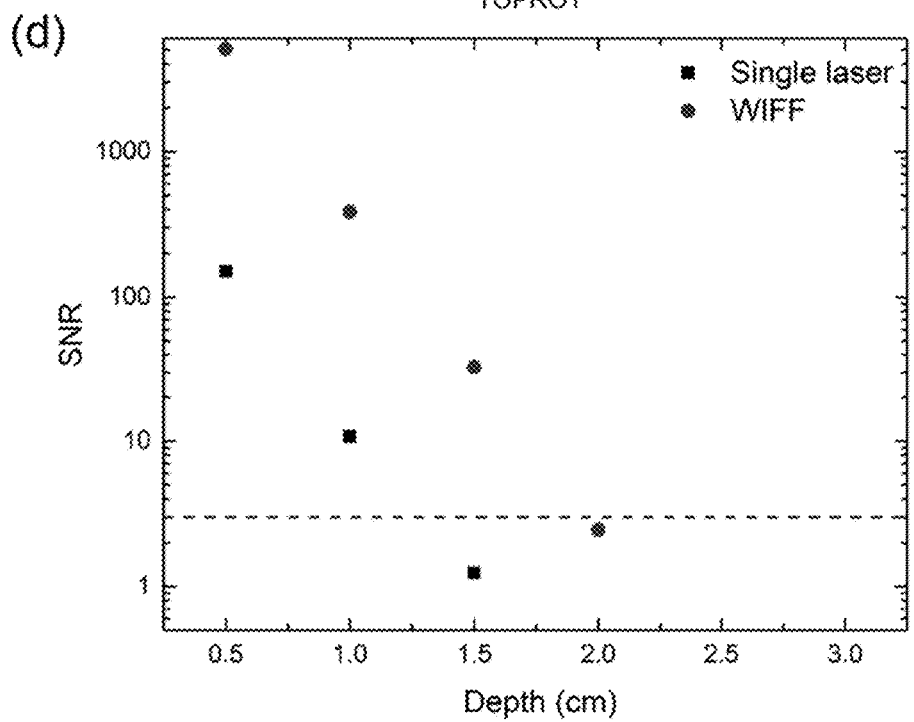
Figure 28E:
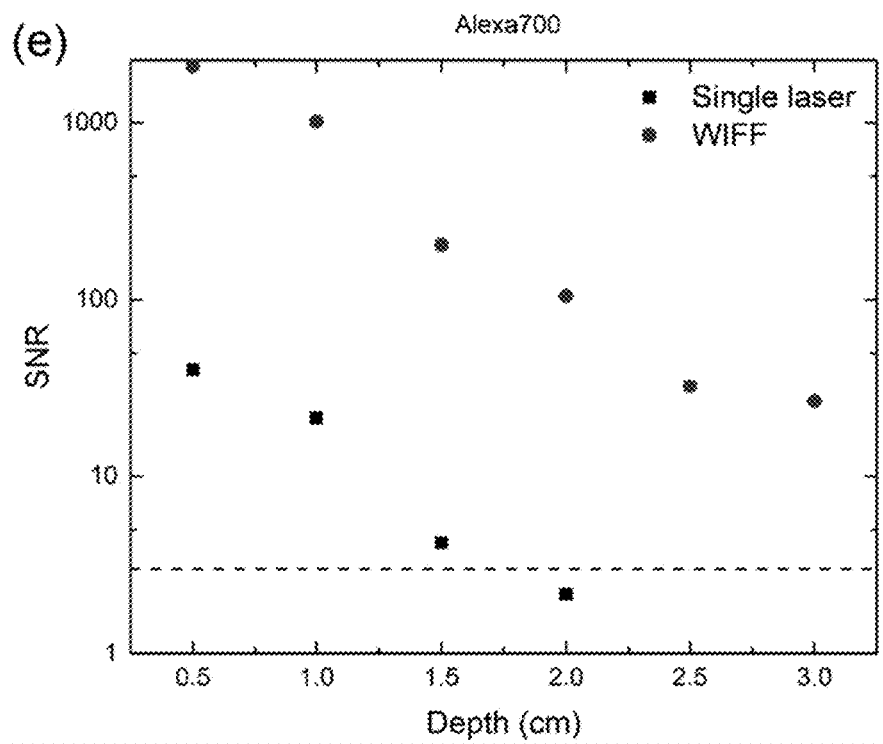
Figure 28F:
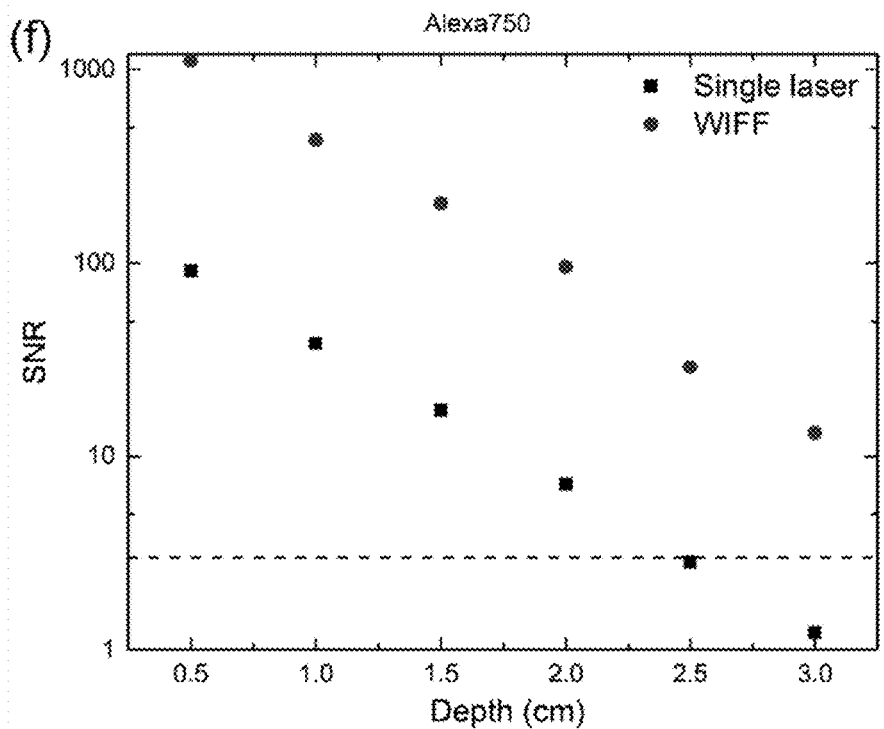
Figure 28G:
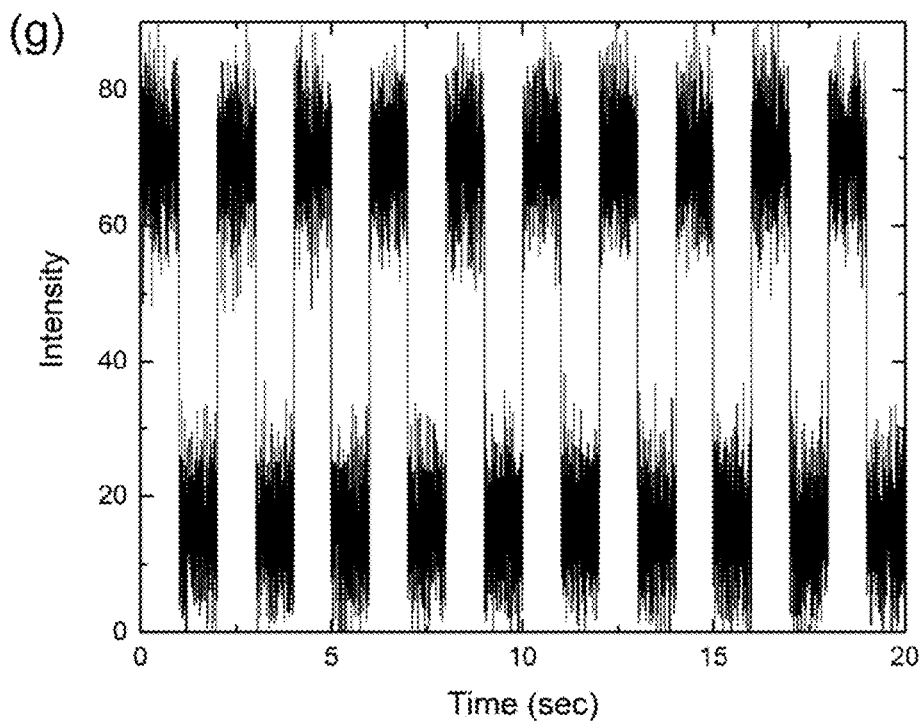
Figure 28H:
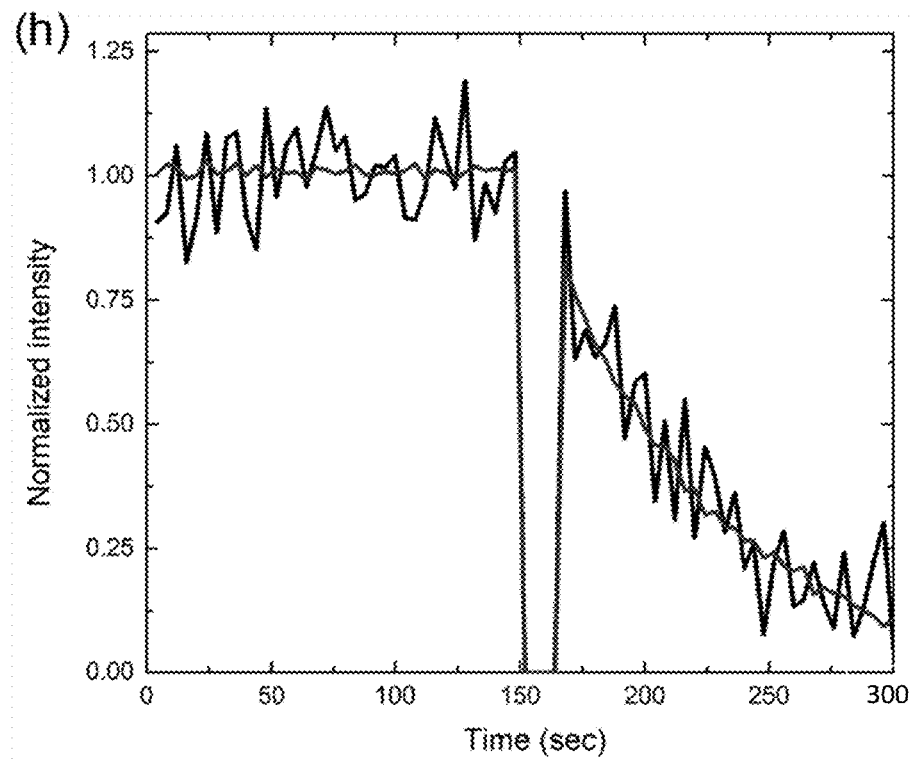
Figure 29A:
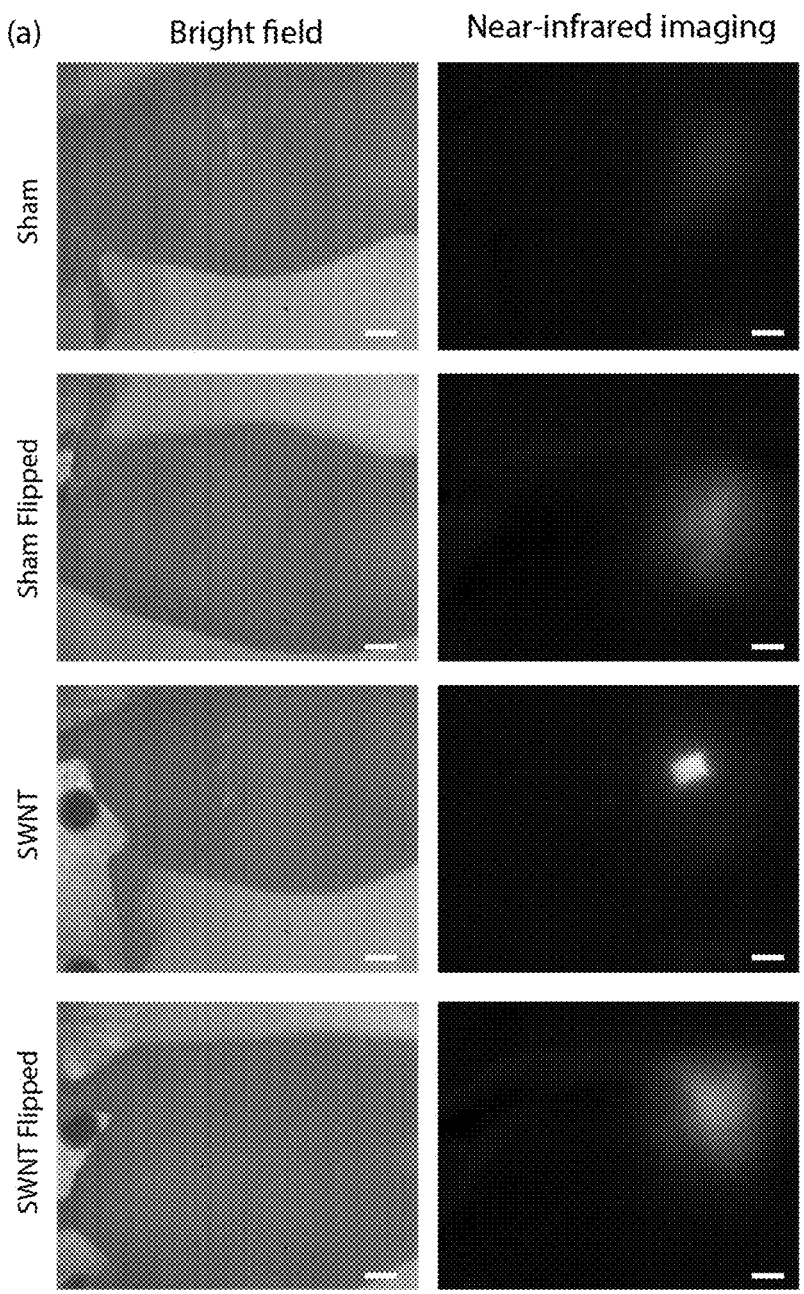
FIGS. 29A-29C depict in vivo imaging. Gels (5×5×2 mm$^3$ gel with 10 mg/l (GT)$_{15}$-SWNTs) were implanted subcutaneously into a mouse near the stomach area.
Figure 29B:
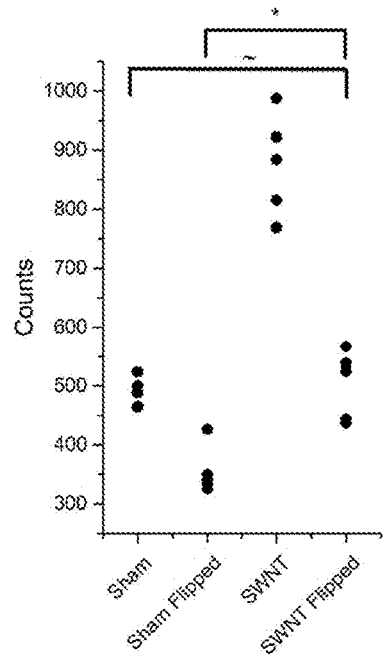
Figure 29C:
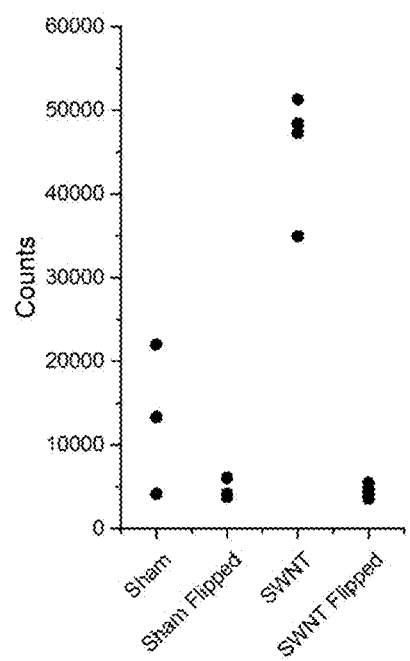
Figure 30A:
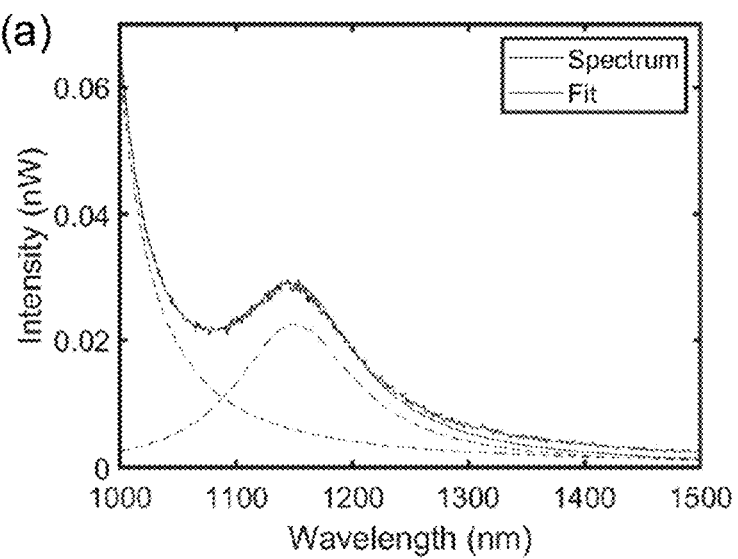
FIGS. 30A-30D depict comparing WIFF with a spectral deconvolution method. Simulated spectral graphs of a sensor signal with a background of various relative powers: 1× (FIG. 30A), 5× (FIG. 30B), and 10× (FIG. 30C) with SNR for WIFF and spectral deconvolution (FIG. 30D). Background ratio represents the ratio between the total power of the background to that of the sensor. Red dashed lines correspond to sensor and background components. The Black dashed line corresponds to SNR of 3. WIFF was performed around the central wavelength that coincides with the sensor absorption peak and 50 nm modulation width. The excitation linewidth was taken to be 5 nm. The extracted parameters were normalized to experimental values obtained for a sensor (5×5×2 mm$^3$ gel with 10 mg/l (GT)$_{15}$-SWNTs) implanted at 3 cm depth into the chicken breast tissue as in FIG. 3f. The noise levels for the signal and the background were estimated to both be 8 pW for the background ratio of 1, and scaled accordingly for other points. SNR was calculated as the ratio between the sensor 2f-component and noise contributions from both 2f-components from background and signal. To calculate spectral features, lossless dispersion was assumed over 600 g/mm grating with 1.0 nm optical resolution coupled to the detector with the same sensitivity as for WIFF. The spectral shot noise was scaled accordingly. A nonlinear curve fitting was performed with the least-squares solver to extract signal intensity. Noise levels were estimated from the confidence intervals of fitting and the distance between the estimated and true levels. The deconvolution method allows for signal retrieval below the background ratio of 6, while WIFF retrieves signals up to 507-times lower as compared to the background (in close agreement with experiments in FIGS. 3A-3G, where autofluorescence background is estimated to be 25 nW, while signals of 40 pW were successfully detected).
Figure 30B:
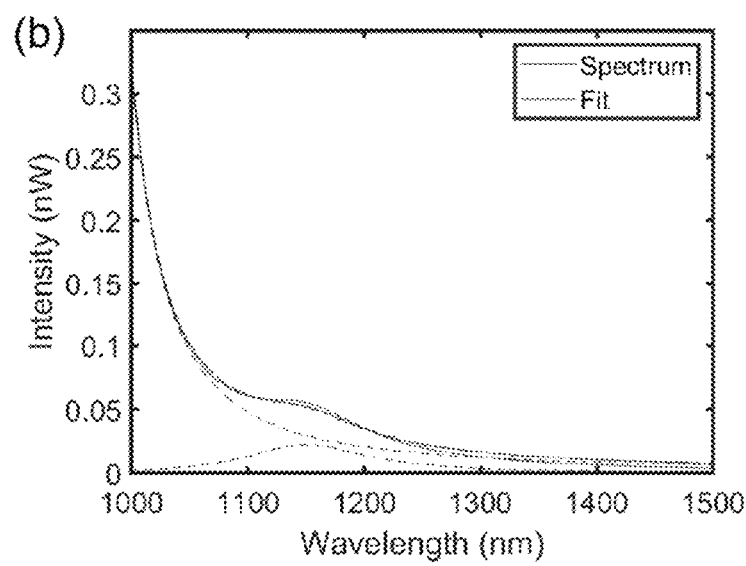
Figure 30C:
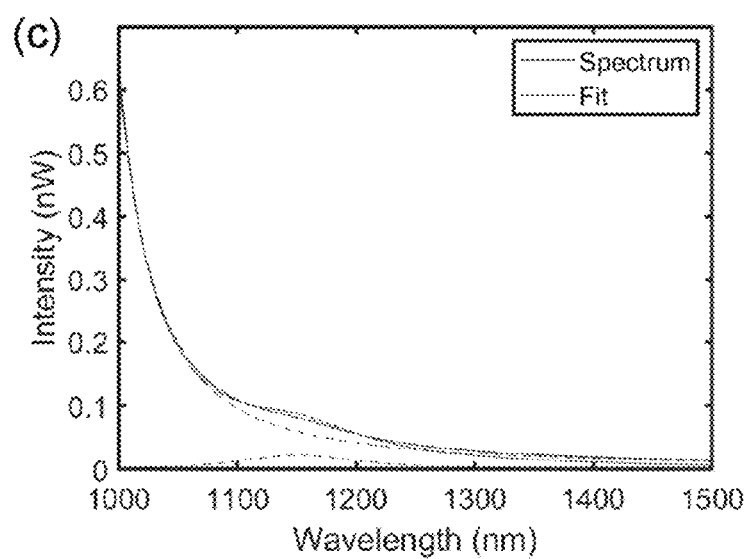
Figure 30D:
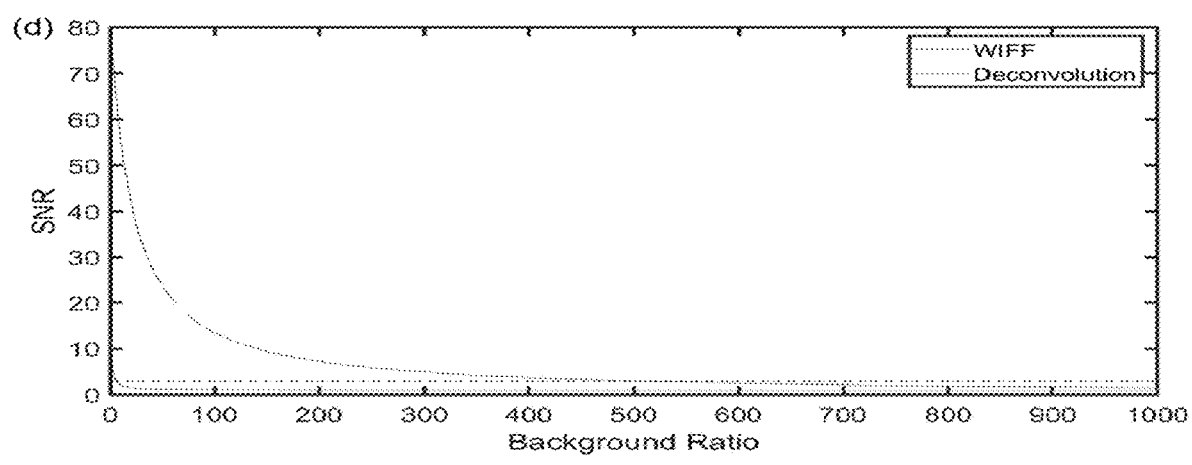

To quantitatively understand the role of tissue autofluorescence on WIFF performance, the autofluorescent background was measured in the near-infrared range from 12 organs of freshly-sacrificed SKH1-E mice. Mice on alfalfa-rich diets were chosen because of their ubiquitous use in biomedical research. The profiles from all organs (FIG. 4A and FIG. 24) display a strong band around 650 nm excitation and 950 nm emission—a feature partially attributed to chlorophyll (FIGS. 26A-26C). See, for example, Krasnovsky Jr, Y. Kovalev, Spectral and kinetic parameters of phosphorescence of triplet chlorophyll a in the photosynthetic apparatus of plants, Biochemistry (Moscow) 79 (2014) 349-361, which is incorporated by reference in its entirety. Unsurprisingly, it was found that the digestive organs to exhibit the highest autofluorescence, but the brain and heart ranked 2$^{nd}$ and 3$^{rd}$ in intensity (FIG. 4B). Because of this, an alfalfa-free diet can significantly reduce organ autofluorescence in mice. See, for example, Y. Inoue, K. Izawa, S. Kiryu, A. Tojo, K. Ohtomo, Diet and Abdominal Autofluorescence Detected by in Vivo Fluorescence Imaging of Living Mice, Molecular Imaging 7 (2008) 7290.2008.0003, each of which is incorporated by reference in its entirety. The autofluorescence band has a spectral tail that extends up to 1200 nm and, therefore, even interferes with near-infrared probes (FIG. 4C). The sensor signal itself does not determine the limit but rather the SNR, where autofluorescence contributes to various noises (FIGS. 27A-27K and see below).

Figure 4D:
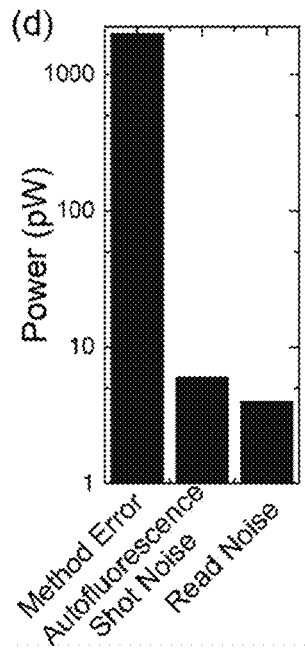

The noise level of 2 nW extracted from measurements in FIGS. 3A-3G was found to be significantly higher (FIG. 4D) than the autofluorescence shot noise (estimated to be 6 pW) and the read noise of the detector (with RMS of 4 pW). The required background subtraction for this measurement manifests in the method error as the sensor signal $P_s$ is computed as the difference between two measurements with ($P_{s+b}$) and without ($P_b$) an implanted sensor:

$$P_s = P_{s+b} - P_b. \tag{5}$$

In practice, this method error appears to dominate the noise contribution at large implantation depths. Accordingly, WIFF eliminates the need for background subtraction in Eq. (5), significantly reducing the noise level as shown above.

Figure 4E:
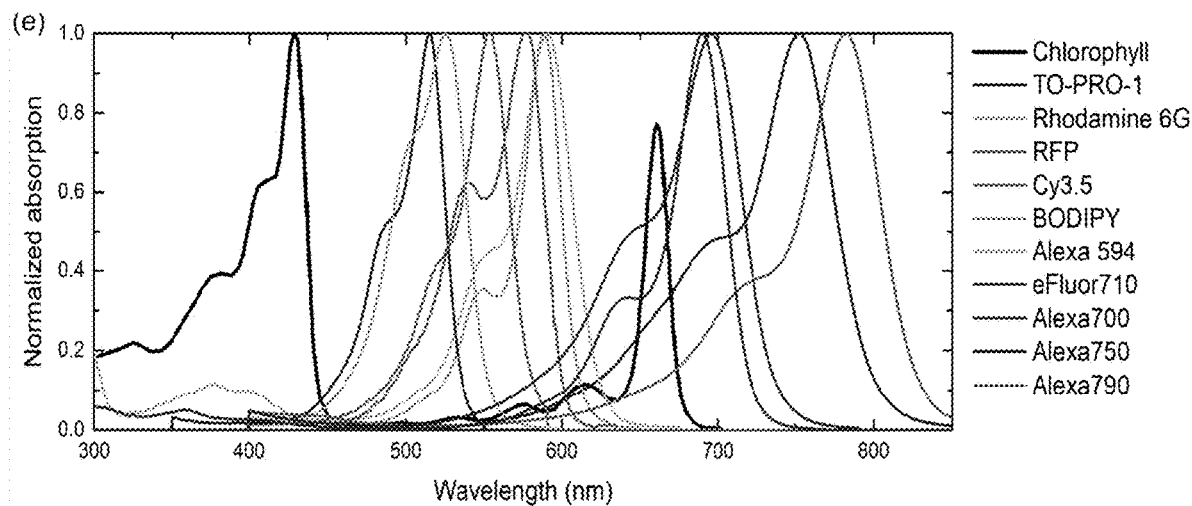
Figure 4F:
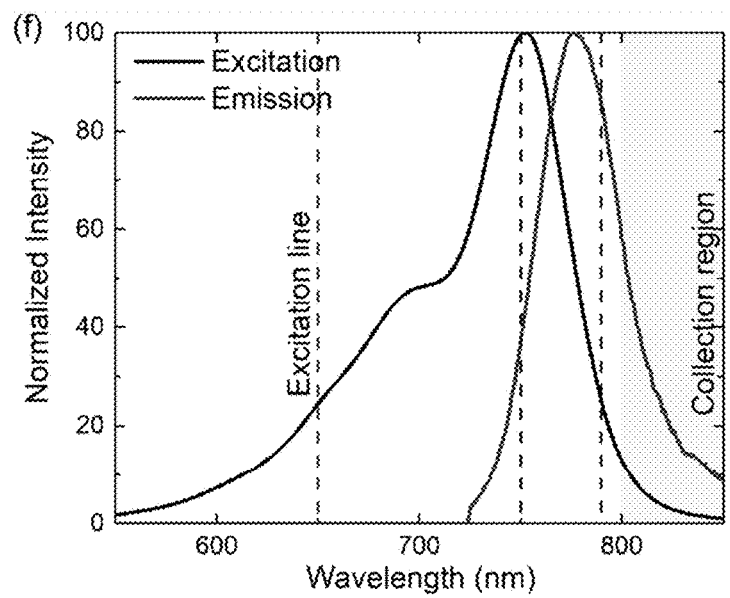
Figure 4G:
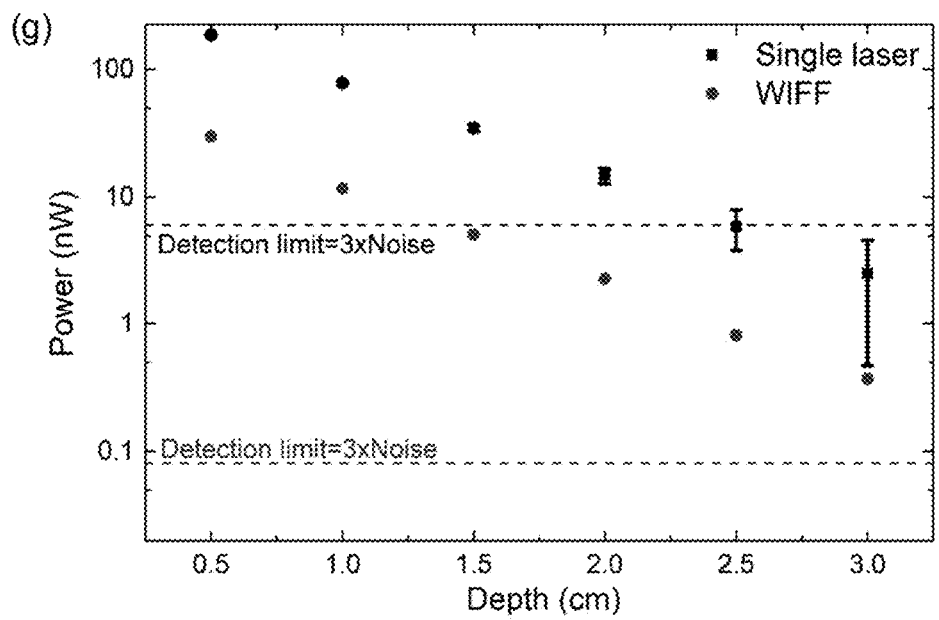
Figure 4H:
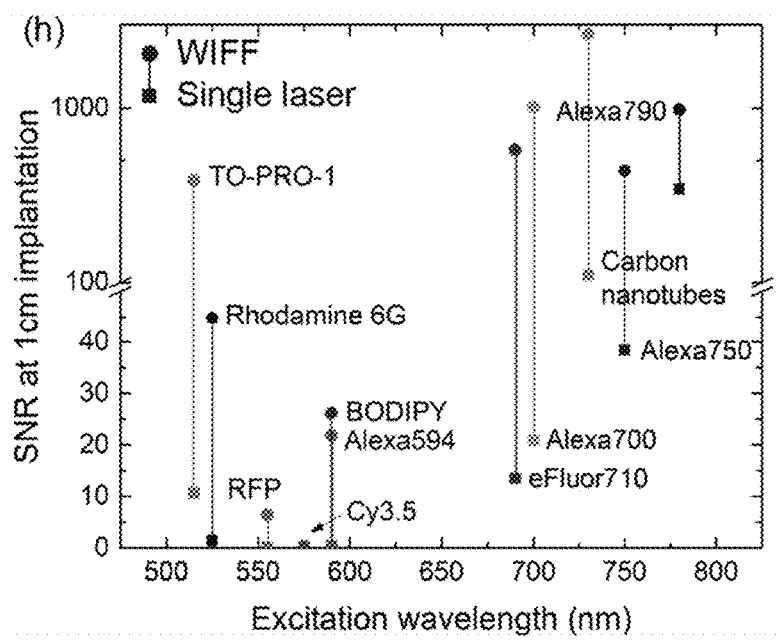
Figure 4I:
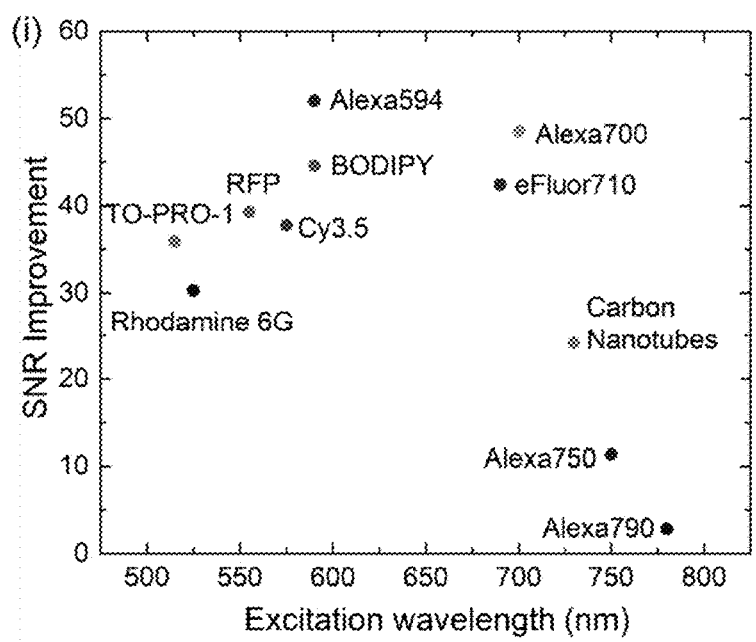

To explore the performance of WIFF across a broad spectral range, the technique was applied to ten fluorescent dyes commonly used in biological assays: TO-PRO-1, Rhodamine 6G, Cy3.5, BODIPY, RFP, Alexa 594, Alexa 700, Alexa 750, Alexa 790, and eFluor 710. Dyes were chosen such that their absorption peaks do not overlap with tissue autofluorescence peaks (FIG. 4E). For every dye, a supercontinuum laser with a tunable filter was used to perform excitation modulation around the respective absorption peak, observing the fluorescence modulation bearing 2f-component (FIG. 4F and FIGS. 28A-28H). To understand SNR values of these measurements, consider that the sensor signal values are determined by a combination of multiple parameters: tissue properties (scattering and absorption), intrinsic dye properties (absorbance, quantum yield), and WIFF modulation efficiency (FIG. 4G and FIG. 29A-29C). On the other hand, the dominant noise in single laser measurements was dictated by the method error due to the presence of autofluorescence, while WIFF successfully eliminates it (FIG. 4H). Therefore, dyes that absorb close to the autofluorescence peak (Alexa 594, BODIPY, eFluor710, and Alexa 700) demonstrate the highest SNR improvement (with Alexa 594 reaching 52-fold) over a single laser approach (FIG. 4I).

In Vivo Sensing with WIFF

Figure 5A:
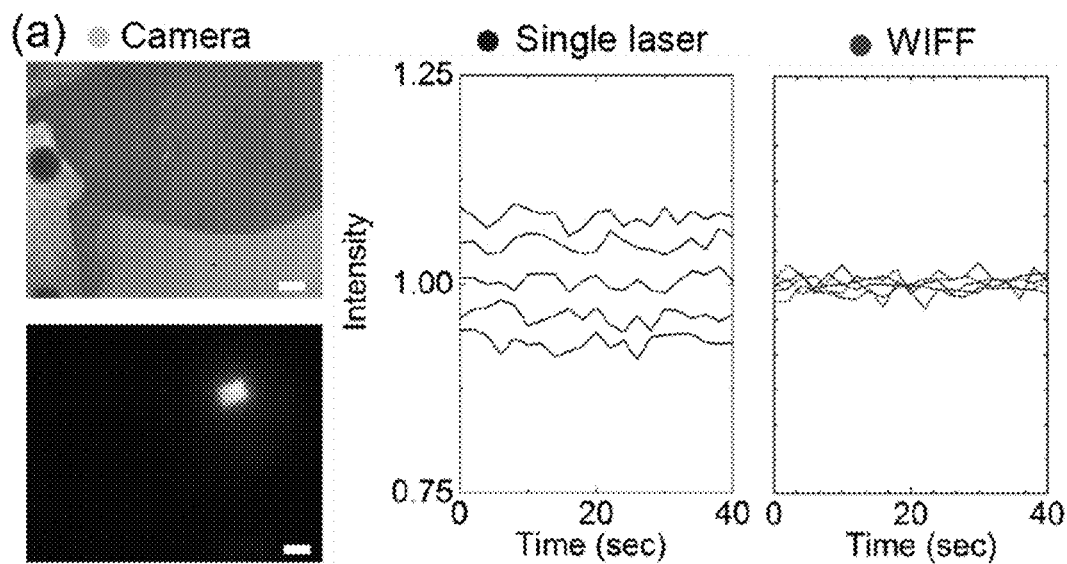
FIGS. 5A-5H depict in vivo sensing.
Figure 5B:
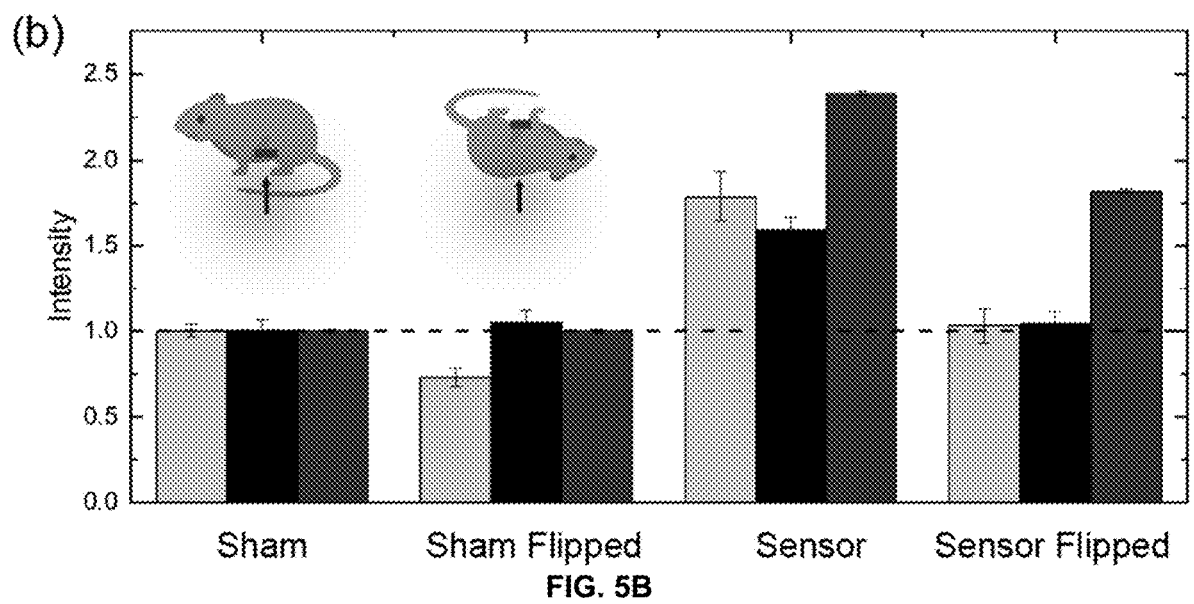

To evaluate WIFF in vivo, the sensitivity of single laser excitation with WIFF was compared in live SKH1-E mice (FIG. 5A). Model sensors embedded in a hydrogel were implanted subcutaneously on the ventral side of the anesthetized mouse approximately 1 mm under the skin. This geometry simulates the configuration of shallow implantation routinely employed for studies, such as persistent drug release, nanosensors for inflammation, and glucose sensing. See, for example, H. Kim, H. Park, S. J. Lee, Effective method for drug injection into subcutaneous tissue, Scientific Reports 7 (2017) 9613; N. M. Iverson, P. W. Barone, M. Shandell, L. J. Trudel, S. Sen, F. Sen, V. Ivanov, E. Atolia, E. Farias, T. P. McNicholas, N. Reuel, N. M. A. Parry, G. N. Wogan, M. S. Strano, In vivo biosensing via tissue-localizable near-infrared-fluorescent single-walled carbon nanotubes, Nature Nanotechnology 8 (2013) 873; and, each of which is incorporated by reference in its entirety. The nIR image exhibits a clear rectangular profile of the hydrogel implant (FIG. 5A). Over n=5 replicas, WIFF allows high fidelity detection of signals in two cases (FIG. 5B) compared to sham: (1) when the mouse is lying on its ventral side with the sensor facing the detector and (2) when the mouse is flipped to its dorsal side such that the light has an extraordinarily complex path through the entire body of the animal at approximately 1.5 cm. The sensor signal remains constant during 40 sec-long experiments with 1% noise levels, also indicating the invariance of G-factor to slight animal variation in these replicas. In contrast, measurements with single laser excitation show ~9% variance between replicas and cannot resolve the latter case (2) (with unpaired t-test of p=0.36 vs. sham). Finally, WIFF was compared with two other techniques used in biomedical sensing. First, near-infrared imaging resolves the implant from the ventral side, but not the dorsal side, being confounded by autofluorescence (FIGS. 30A-30D). Second, WIFF also demonstrates a dramatic advantage over spectroscopic measurements with subsequent deconvolution (FIGS. 30A-30D) that were previously suggested for autofluorescence elimination. See, for example, N. M. Iverson, P. W. Barone, M. Shandell, L. J. Trudel, S. Sen, F. Sen, V. Ivanov, E. Atolia, E. Farias, T. P. McNicholas, N. Reuel, N. M. A. Parry, G. N. Wogan, M. S. Strano, In vivo biosensing via tissue-localizable near-infrared-fluorescent single-walled carbon nanotubes, Nature Nanotechnology 8 (2013) 873, which is incorporated by reference in its entirety.

Figure 5C:
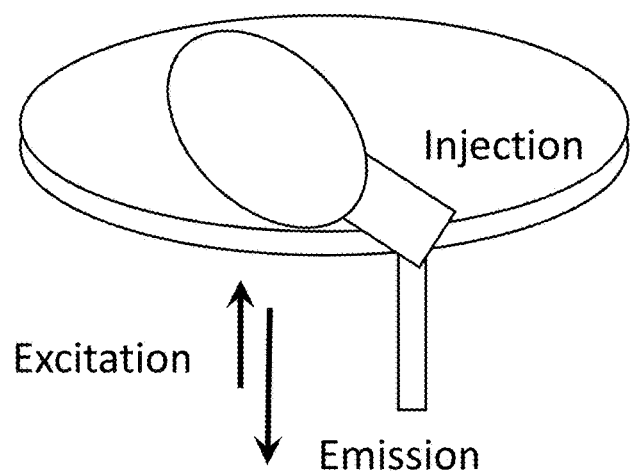
Figure 5D:
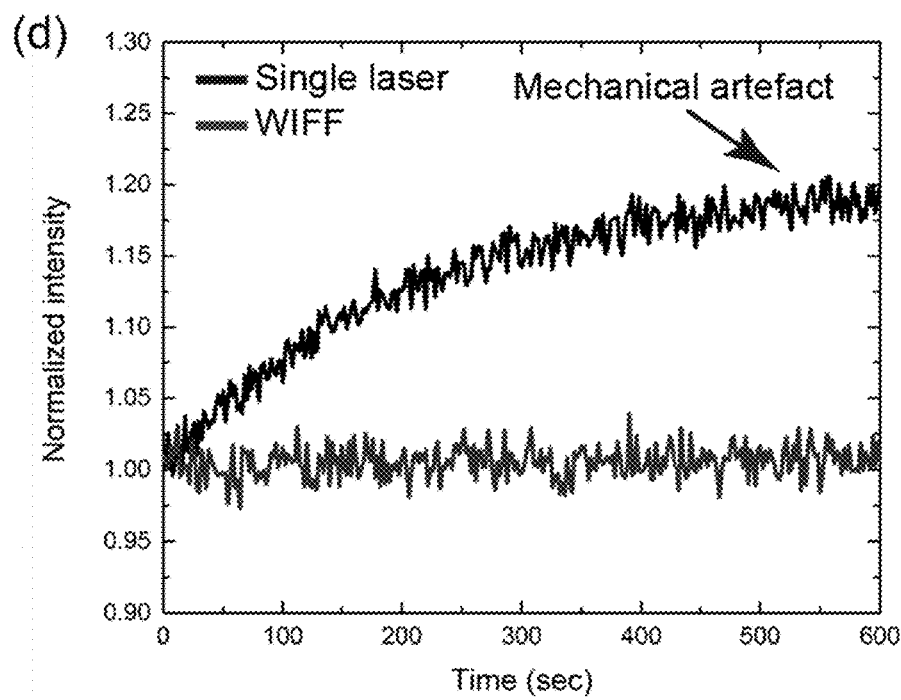
Figure 5E:
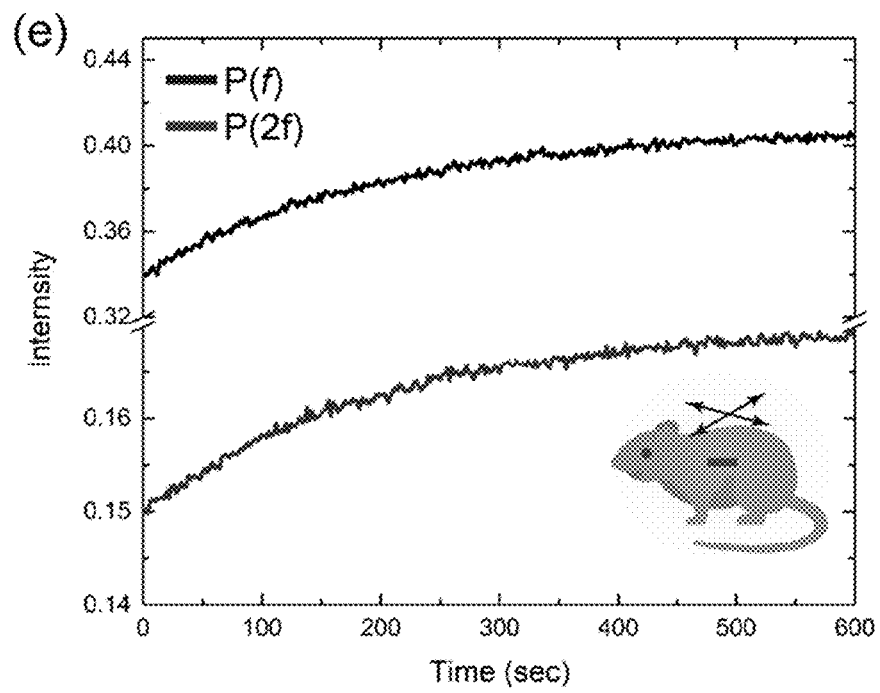

It was further illustrate how WIFF handles mechanical artefacts that can be detrimental for optical sensing. In this context, movement and breathing are unavoidable during the in vivo experiments. During a control injection of 100 μl saline in the vicinity of a subcutaneously-implanted sensor, the centroid of the implant shifted 2.5 mm increasing its imaging intensity by 43% as compared to before the injection (FIG. 5C). Measurements with single laser excitation demonstrated a signal drift of 20% over 600 sec as an artefact, while WIFF produced a completely stable intensity trace despite these perturbations (FIG. 5D). Here, WIFF utilizes the separated background signal as an internal reference. A detailed analysis of 2f and f-components depicts their simultaneous rise, canceling out such mechanical artefacts when using Eq. (4) (FIG. 5E). This self-referencing feature of WIFF is critical for fluorescent assays and sensors, allowing users to distinguish between signal artefacts associated with animal movements.

Figure 5F:
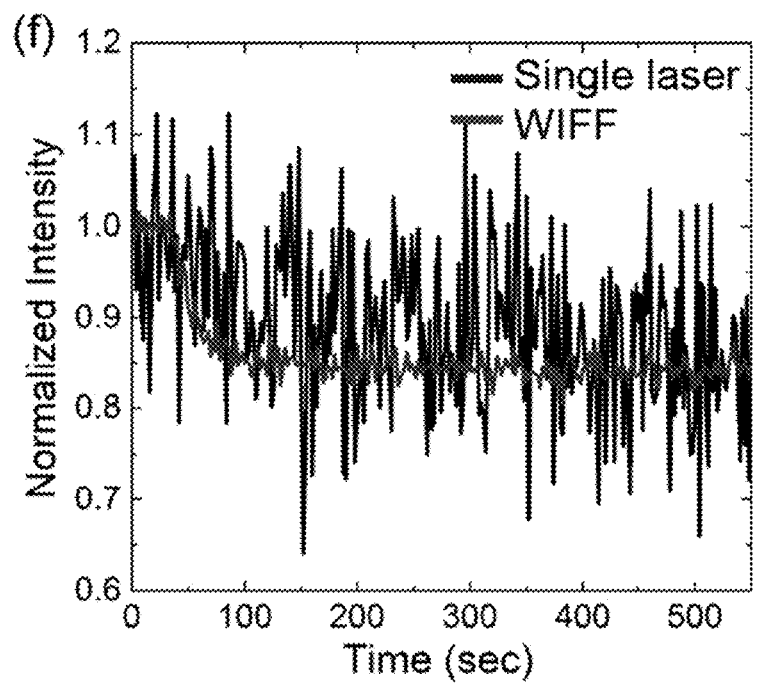
Figure 5G:
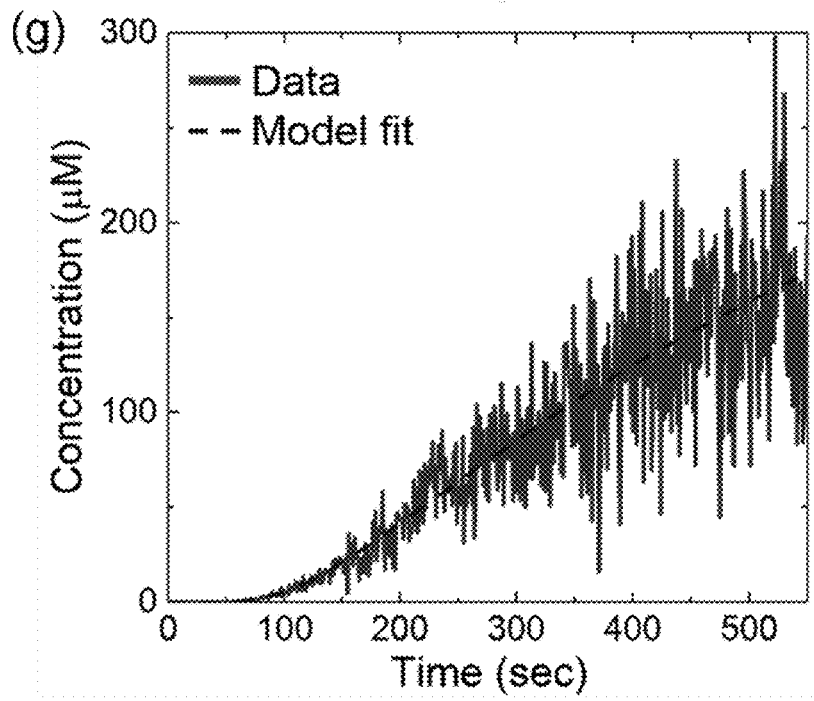
Figure 5H:
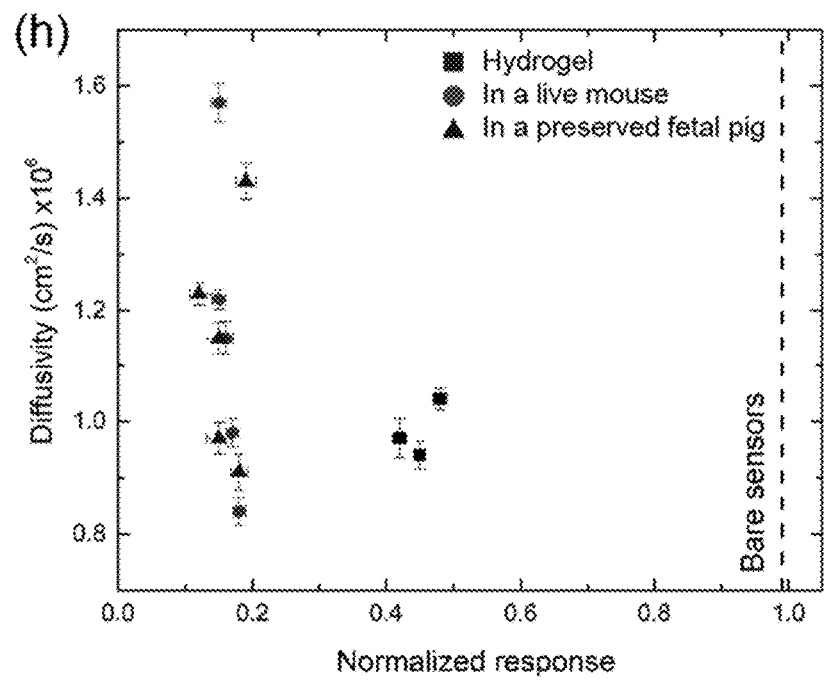
Figure 6A:
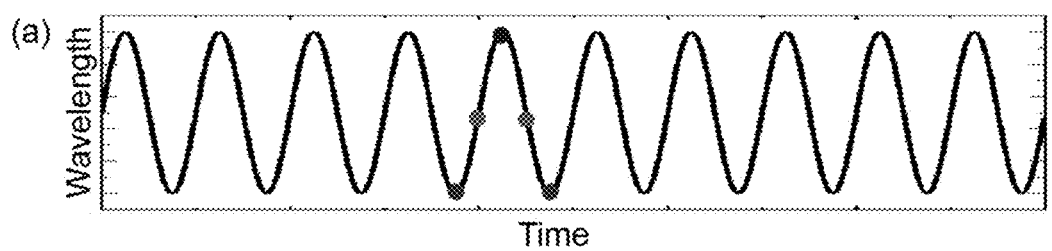
FIGS. 6A-6E depict graphs of wavelength modulation principle.
Figure 6B:
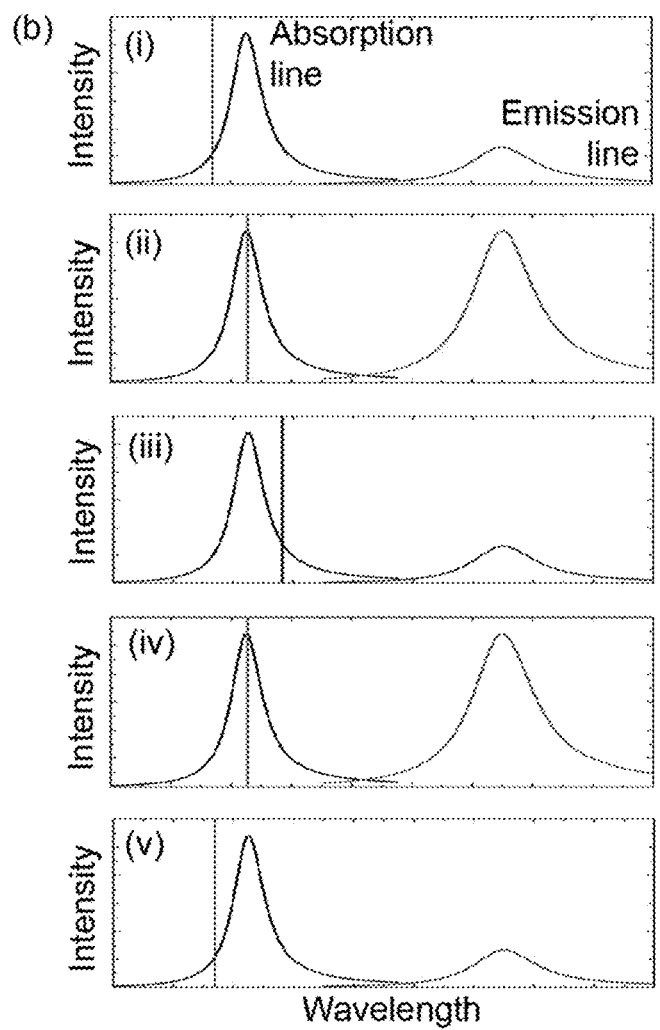
Figure 6C:
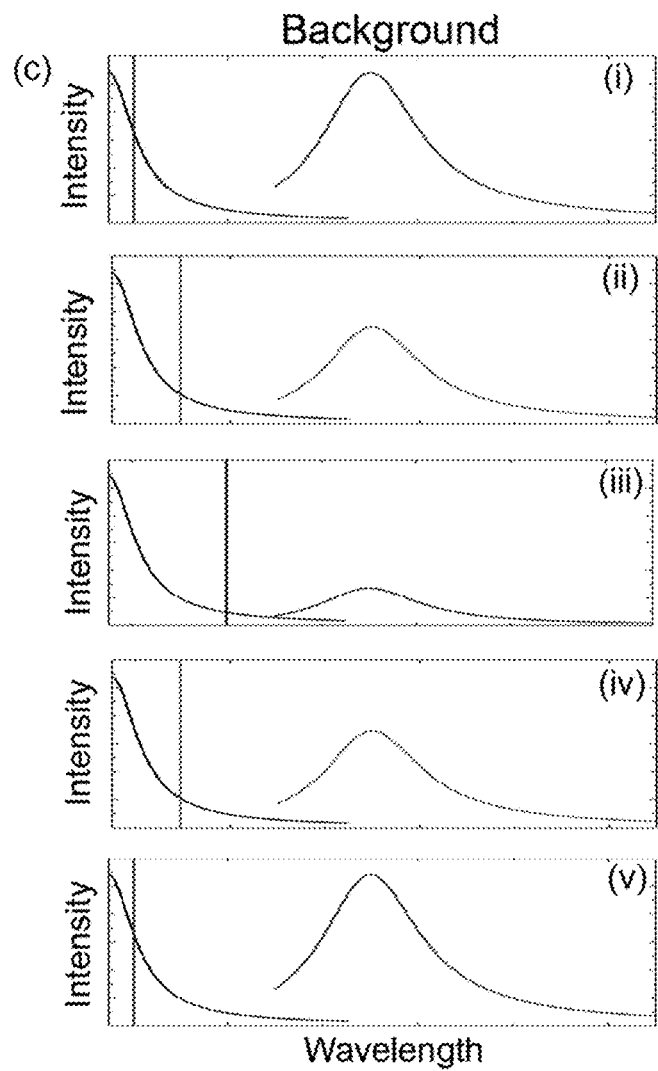
Figure 6D:
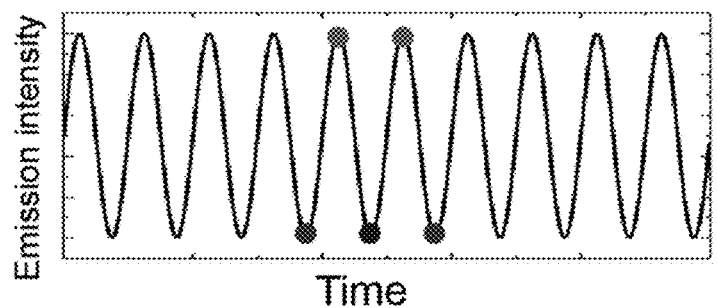
Figure 6E:
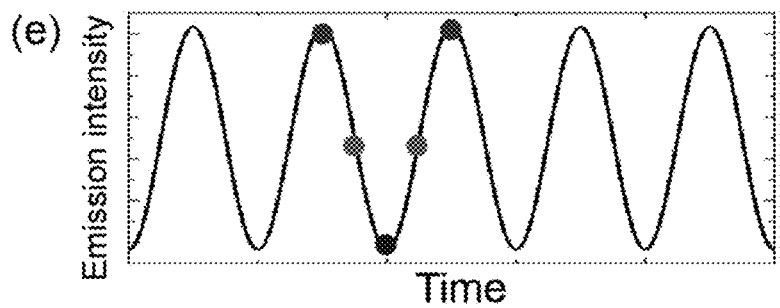
Figure 31:
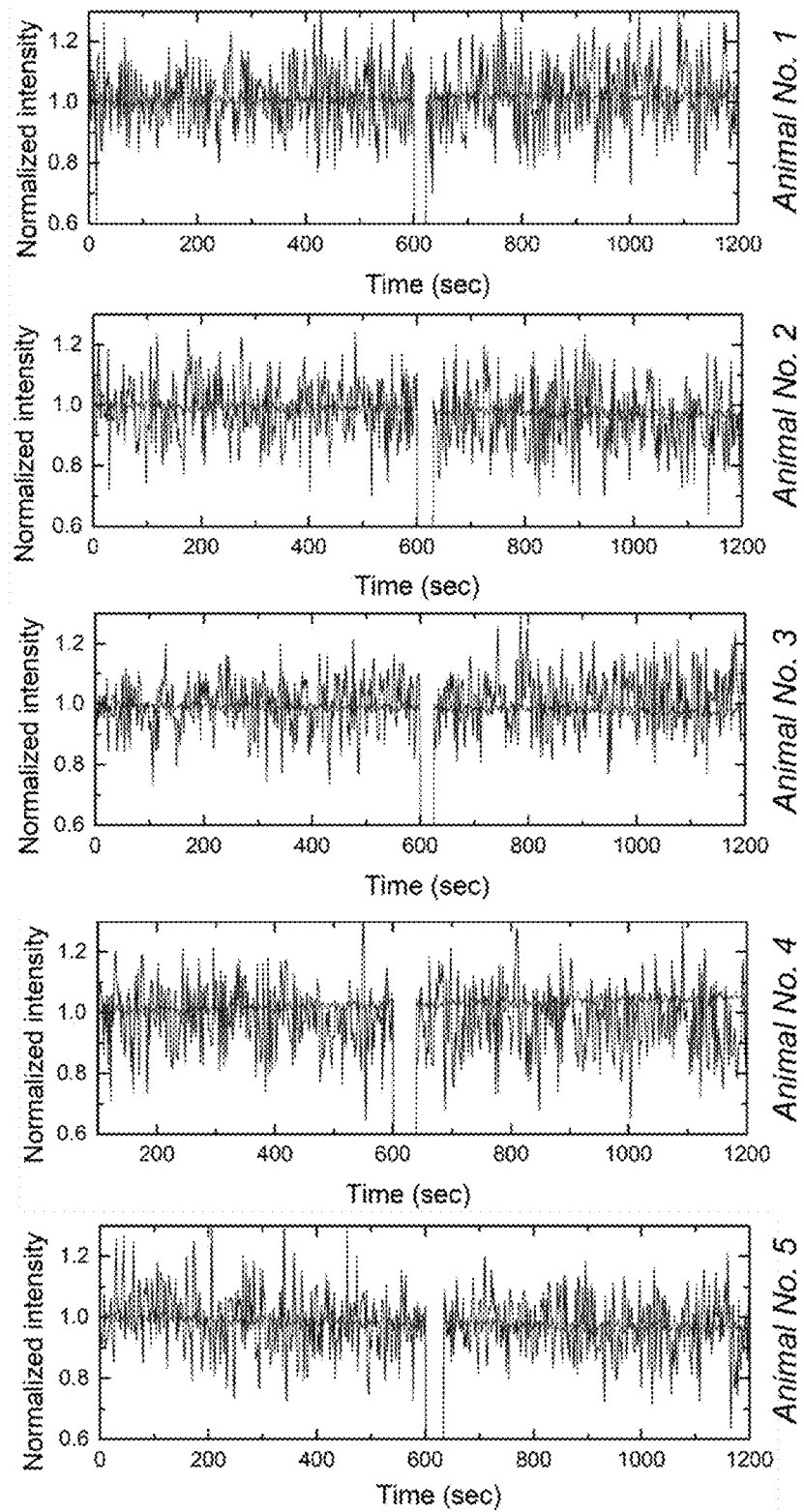
FIG. 31 depicts control experiments with mice. Normalized intensities for single laser (black) and WIFF (red), corrected for the background signal, show no drift above 4% over the course of experiments. Sensors ($10 \times 10 \times 2$ mm$^3$ gel with 20 mg/l $(AC)_{15}$-SWNTs)) were implanted into the intraperitoneal space of mice. Animals were monitored for 600 sec and then an injection of 1 ml of saline was performed through an implanted catheter.
Figure 32A:
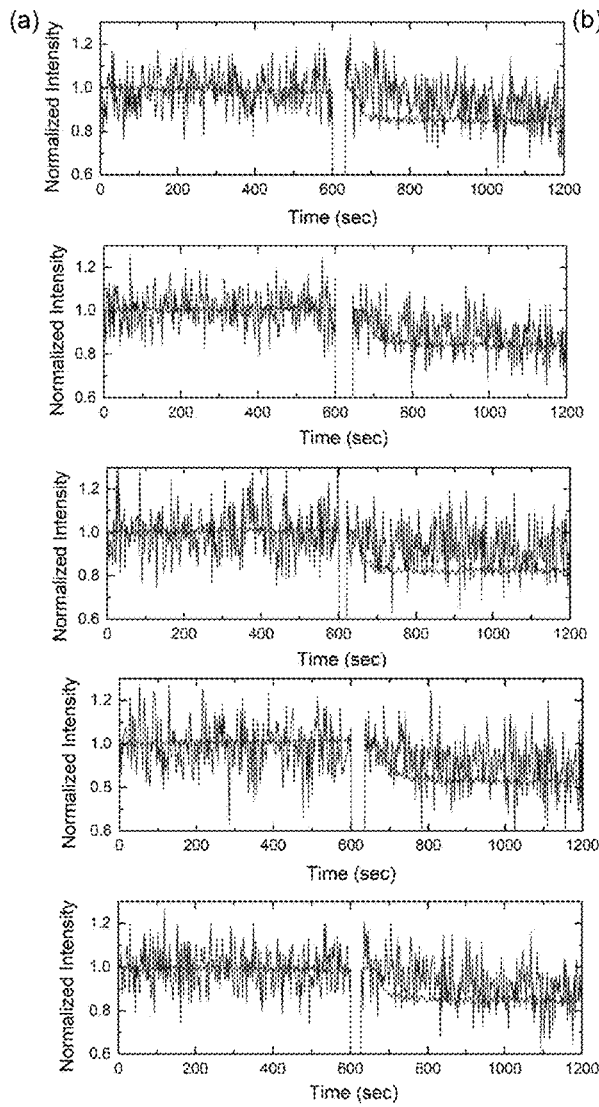
FIGS. 32A-32B depict sensing experiments with mice.
Figure 32B:
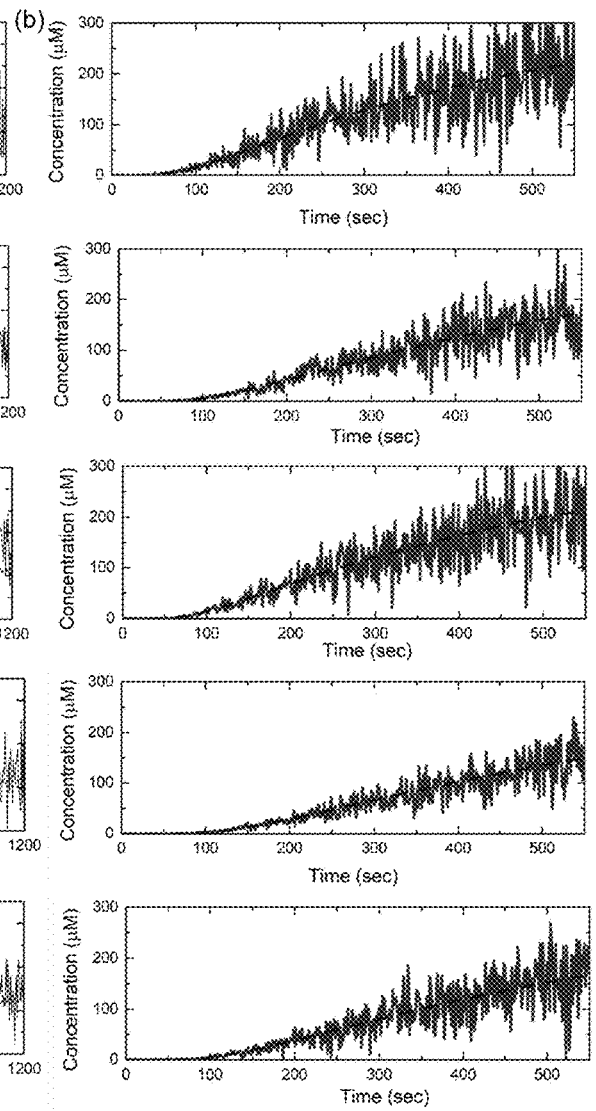
Figure 33:
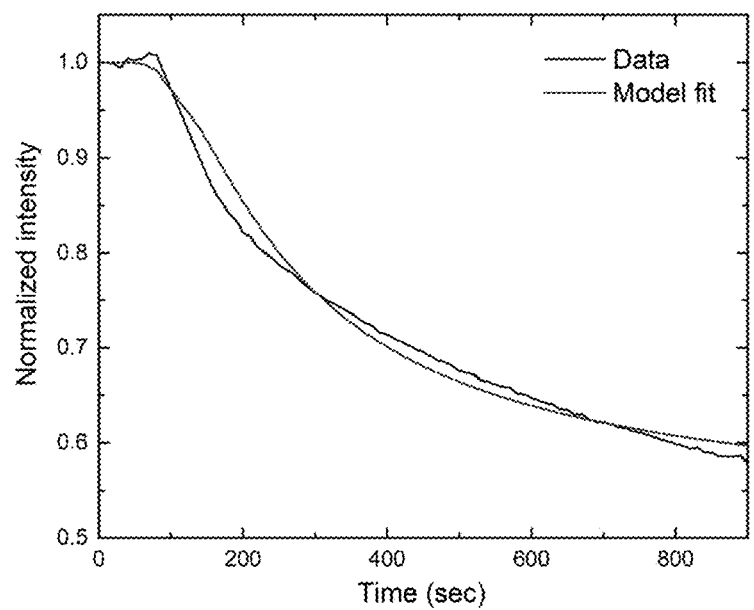
FIG. 33 depicts in vitro hydrogel dynamics. The normalized response of a sensor ($10 \times 10 \times 2$ mm$^3$ gel with 20 mg/l $(AC)_{15}$-SWNTs) in vitro upon the addition of 100 μM riboflavin at t=0. The black curve represents the measured data, while the red line is a fit to the diffusion equation, yielding a diffusion constant of $1.04 \times 10^{-6}$ cm$^2$/s.

The ultimate goal of fluorescent sensing is to detect analytes in vivo at the implantation point and wirelessly transmit the signal to the surface of the body. To demonstrate this capability, the sensor was implanted into the intraperitoneal space from the ventral side of an SKH1-E mouse. Upon the injection of 300 μM riboflavin through the catheter implanted nearby the sensor, 17% quenching was observed with the onset time of 51 sec after the injection (FIG. 5F), while the control showed no response after saline injection (FIG. 31). WIFF measurements demonstrate an average of 10 times noise improvement over single laser excitation (FIG. 32A-32B). The extracted concentration trace demonstrates a slow increase characteristic of the diffusion process (FIG. 5G), allowing us to estimate riboflavin diffusivities in the intraperitoneal space of live mice and preserved fetal pigs (FIG. 5H). These types of measurements are critical for many biomedical problems focused on tissue permeability, such as targeted delivery of therapeutics, and changes in vascular permeability related to disorders, either as the origin or manifestation of various diseases. See, for example, D. Rosenblum, N. Joshi, W. Tao, J. M. Karp, D. Peer, Progress and challenges towards targeted delivery of cancer therapeutics, Nature Communications 9 (2018) 1410; and H. Fukui, Increased Intestinal Permeability and Decreased Barrier Function: Does It Really Influence the Risk of Inflammation?, Inflammatory Intestinal Diseases 1 (2016) 135-145, each of which is incorporated by reference in its entirety. In this proof-of-concept, riboflavin perfused into the injection space with the extracted diffusivity values between 0.8 and $1.6 \times 10^{-6}$ cm$^2$/s, closely matching those in the hydrogel ($1.04 \times 10^{-6}$ cm$^2$/s, FIG. 33).

Figure 34A:
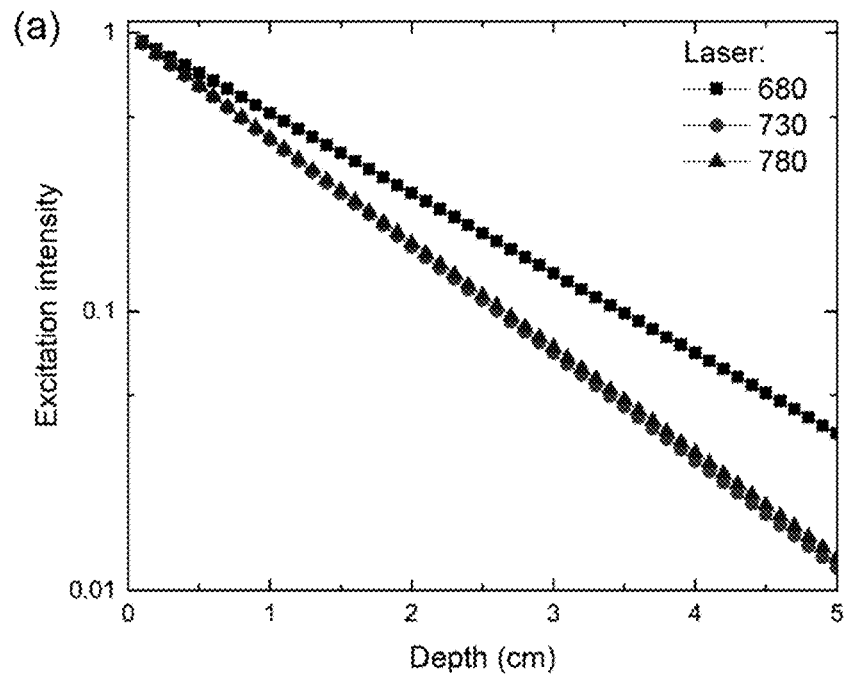
FIGS. 34A-34B depict wavelength dispersion due to tissue absorption.
Figure 34B:
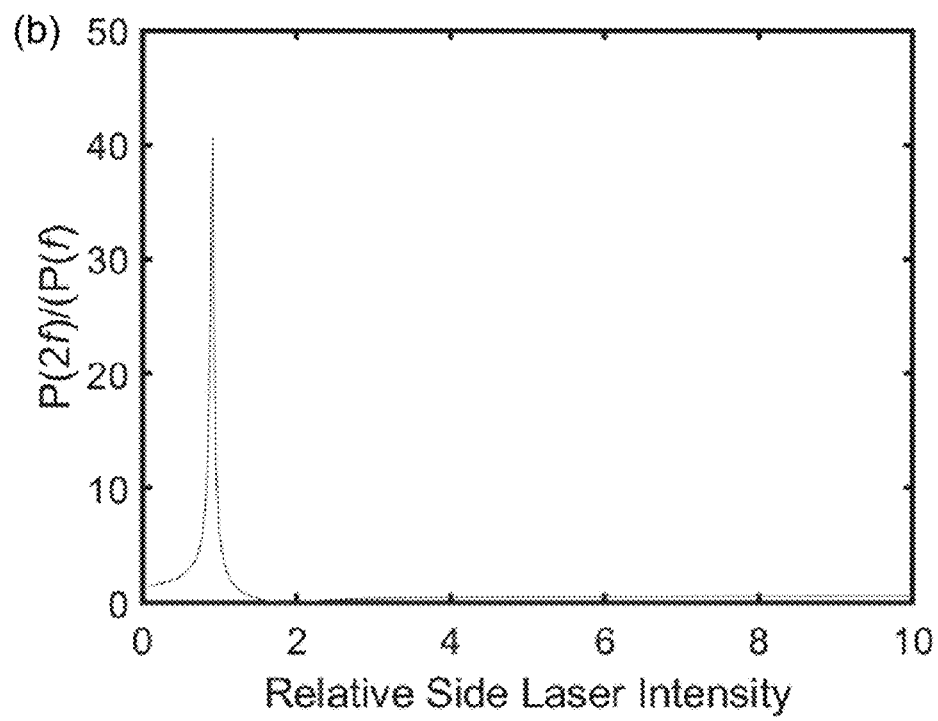

Finally, some limitations can be noted in that the excitation wavelengths themselves exhibit different tissue absorption that can distort the modulation pattern. This effect depends on the implantation depth and tissue absorption profile and can be mitigated by correcting the relative laser intensities (FIGS. 34A-34B). In the implementation of WIFF, care must be taken to appropriately fixate the sensor during the implantation, as WIFF, similar to other intensity-based fluorescent measurements, is unable to differentiate between untethered sensor movement and the sensor response itself.

In this work, a wavelength-induced frequency filtering (WIFF) was developed as a means of extending fluorescent biological assays to the in vivo environment, making the application of deep tissue sensing possible. WIFF overcomes the limitations of unfavorable intrinsic autofluorescence in the form of a method error and mechanical artefacts. This is achieved by an experimental system of cyclic wavelength excitation to separate the emission waveform from the autofluorescent background, lowering noise levels, and to simultaneously use this background as an internal reference, self-correcting for artefacts. As a result, WIFF allows us to detect signals from extraordinarily deep implants of up to 5.5±0.1 cm, demonstrating SNR improvements up to 52-fold in tissue phantoms, chicken tissue, preserved fetal pigs, and SKH1-E mouse model. The method can be readily applied to various fluorescent sensors that emit across the entire visible range, as illustrated for ten common fluorescent molecules used in biomedical assays. WIFF also brings the ability to perform real-time in vivo sensing with high fidelity, as demonstrated for $H_2O_2$, riboflavin, and ascorbic acid sensors. Such sensing traces capture the dynamics of local analyte concentrations to reveal diffusion constants related to the permeability of deep tissues. Overall, WIFF will allow for the development of new, in vivo assays in biomedical research by extending a large number of fluorescent probes to previously inaccessible in vivo environments. Real-time biochemical monitoring of such locations will be of great interest to the fields of fundamental biochemical research, personalized diagnostics, and the delivery of targeted therapeutics.

Methods

Tissue autofluorescence measurements. The excitation-emission maps of the tissue samples were obtained using the excitation from supercontinuum source (EXW-12, NKT Photonics) with a tunable filter (LLTF CONTRAST-SR-VIS-HP8, Photon Inc) on the inverted microscope (AxioVision, Zeiss) using 20× air objective coupled to the near-infrared camera (InGaAs OMA V, Princeton Instruments) through a spectrometer (SP2500, PI-Action). Typical integration time was 60 sec for one excitation wavelength with several mW of power on the sample. The setup was intensity calibrated.

Carbon nanotube sensors preparation. Raw HiPCO SWNTs were purchased from NanoIntegris (Lot #HR27-104). All ssDNA oligonucleotides were purchased from Integrated DNA Technologies. Carbon nanotube suspension for $H_2O_2$ (ascorbic acid) detection was prepared by mixing 1 mg of $(GT)_{15}$ $((ACCA)_7)$ oligonucleotide and 0.25 mg of HiPCO SWNT. All suspensions were diluted to 1 mL of 50 mM NaCl. For riboflavin detection, 1 mg of $(AC)_{15}$ oligonucleotide was used instead. The mixture was sonicated with a 3 mm probe tip (Cole-Parmer) for 20 min at 40% amplitude in an ice bath. The sample was then centrifuged twice at 16,000 g for 90 minutes each to remove unsuspended SWNT bundles. The concentration of the SWNT suspension was determined using its absorbance at 632 nm and an extinction coefficient of 0.036 (mg/L)$^{-1}$ cm$^{-1}$. Unless otherwise stated, (9,4) and (8,6) chiralities were excited in a sample that have absorption peaks at 720 and 735 nm, respectively, as a model sensor. Carbon nanotubes were selected as they are routinely used as near-infrared sensors, because of their single-molecule sensitivity, corona-modulated selectivity, and resistance to photobleaching. See, for example, A. A. Boghossian, J. Zhang, P. W. Barone, N. F. Reuel, J.-H. Kim, D. A. Heller, J.-H. Ahn, A. J. Hilmer, A. Rwei, J. R. Arkalgud, C. T. Zhang, M. S. Strano, Near-Infrared Fluorescent Sensors based on Single-Walled Carbon Nanotubes for Life Sciences Applications, ChemSusChem 4 (2011) 848-863; J. Zhang, M. P. Landry, P. W. Barone, J.-H. Kim, S. Lin, Z. W. Ulissi, D. Lin, B. Mu, A. A. Boghossian, A. J. Hilmer, A. Rwei, A. C. Hinckley, S. Kruss, M. A. Shandell, N. Nair, S. Blake, F. Şen, S. Şen, R. G. Croy, D. Li, K. Yum, J.-H. Ahn, H. Jin, D. A. Heller, J. M. Essigmann, D. Blankschtein, M. S. Strano, Molecular recognition using corona phase complexes made of synthetic polymers adsorbed on carbon nanotubes, Nature Nanotechnology 8 (2013) 959; M. P. Landry, S. Kruss, J. T. Nelson, G. Bisker, N. M. Iverson, N. F. Reuel, M. S. Strano, Experimental tools to study molecular recognition within the nanoparticle corona, Sensors (Basel) 14 (2014) 16196-16211; A. Hendler-Neumark, G. Bisker, Fluorescent Single-Walled Carbon Nanotubes for Protein Detection, Sensors (Basel) 19 (2019) 5403; M. P. Landry, H. Ando, A. Y. Chen, J. Cao, V. I. Kottadiel, L. Chio, D. Yang, J. Dong, T. K. Lu, M. S. Strano, Single-molecule detection of protein efflux from microorganisms using fluorescent single-walled carbon nanotube sensor arrays, Nature Nanotechnology 12 (2017) 368; H. Jin, D. A. Heller, M. Kalbacova, J.-H. Kim, J. Zhang, A. A. Boghossian, N. Maheshri, M. S. Strano, Detection of single-molecule H2O2 signaling from epidermal growth factor receptor using fluorescent single-walled carbon nanotubes, Nature Nanotechnology 5 (2010) 302; G. Bisker, N. A. Bakh, M. A. Lee, J. Ahn, M. Park, E. B. O'Connell, N. M. Iverson, M. S. Strano, Insulin Detection Using a Corona Phase Molecular Recognition Site on Single-Walled Carbon Nanotubes, ACS Sensors 3 (2018) 367-377; and G. Bisker, J. Dong, H. D. Park, N. M. Iverson, J. Ahn, J. T. Nelson, M. P. Landry, S. Kruss, M. S. Strano, Protein-targeted corona phase molecular recognition, Nature Communications 7 (2016) 10241, each of which is incorporated by reference in its entirety.

Phantom tissue preparation. A phantom tissue was fabricated with parameters close to those of a mouse brain as it was found to have the second-highest autofluorescence level after stomach, making the problem of autofluorescence relevant when dealing with such tissue. Additionally, brain sensing poses an important biomedical problem. To simulate the light propagation in such tissue, approximate values have been taken from Jacques, et al. to be: $\mu_{abs}$=0.02 cm$^{-1}$, $\mu_{sca}$=17 cm$^{-1}$ at the $\lambda_{exc}$=730 nm excitation and $\mu_{abs}$=0.09 cm$^{-1}$ and $\mu_{sca}$=2 cm$^{-1}$ at $\lambda_{em}$=1150 nm emission. See, for example, S. L. Jacques, Optical properties of biological tissues: a review, Physics in Medicine and Biology 58 (2013) R37-R61, which is incorporated by reference in its entirety.

The tissue absorption in the region of interest is dominated by water. Hence, a water solution closely mimics absorption properties of the brain tissue. According to Flock et al., adding 0.7% intralipid allows us to achieve $\mu_{sca}$=17 cm$^{-1}$ at 730 nm and 2 cm$^{-1}$ at 1150 nm. See, for example, S. T. Flock, S. L. Jacques, B. C. Wilson, W. M. Star, M. J. C. van Gemert, Optical properties of intralipid: A phantom medium for light propagation studies, Lasers in Surgery and Medicine 12 (1992) 510-519, which is incorporated by reference in its entirety. The match between experimental measurements and Monte Carlo simulations proves that the phantom tissue has properties similar to those in the simulation. To introduce autofluorescence, 0.15 mg/l of chlorophyll was added, which corresponds to the brain autofluorescence when excited at 730 nm. The mixture of chlorophyll, intralipid was complemented by 1% agarose heated to 90° C. to dissolve agarose and slowly cooled down to room temperature, which solidified the mixture into the gel. The mixtures were molded in 3D-printed forms of various thicknesses.

The chicken breast tissue was purchased frozen from the supermarket and was not found to have any autofluorescence. To recreate the properties of living tissues, the tissue was soaked in 0.15 mg/l chlorophyll solution overnight. For Monte Carlo simulations, the following parameters were estimated: $\mu_{abs}$=0.02 cm$^{-1}$, $\mu_{sca}$=12 cm$^{-1}$ at the $\lambda_{exc}$=730 nm excitation and $\mu_{abs}$=0.08 cm$^{-1}$ and $\mu_{sca}$=1.9 cm$^{-1}$ at $\lambda_{em}$=1150 nm emission.

The fetal pigs (Nasco, LS03783) were purchased preserved in propylene glycol. A 10×10 mm piece of hydrogel was implanted into the intraperitoneal space through a ventral incision. A 2.5" catheter was implanted in the intraperitoneal space through the same incision. The abdominal muscles and skin were closed using sutures. During imaging 3 mL of 1 mM riboflavin (or saline for controls) was injected into the intraperitoneal space through the catheter after collecting fluorescent baseline for 10 minutes. The specific amount of the analyte was chosen to make sure to fill the space where a sensor was implanted, while high enough concentration was used to ensure reasonable diffusion times.

Monte Carlo simulations. To simulate light propagation through a tissue, a probabilistic approach based on a Monte Carlo scheme was used. See, for example, V. B. Koman, C. Santschi, O. J. F. Martin, Maximal absorption regime in random media, Opt. Express 24 (2016) A1306-A1320, each of which is incorporated by reference in its entirety. Incident light is treated as wavepackets instead of single photons to simulate absorption along the optical path. Between two successive scattering events, the wavepacket travels in a straight line losing its energy through absorption of the tissue, characterized by $\mu_{abs}$, according to Beer-Lambert's law. The mean free path of light $l_{free}$ between two successive scattering events is found as $l_{free}$=1/($\mu_{sca}$(1−g)) with g=<cos θ> the average scattering angle or anisotropy parameter, taken to be 0.9 in this work. The distance between two consecutive scattering events p follows the random distribution expressed by p=−$l_{free}$ log Σ, where Σ is sampled uniformly between 0 and 1. When a wavepacket is scattered, it changes its direction with the scattering probability function q(θ) given by the Henyey-Greenstein distribution:

$$q(\theta) = \frac{1-g^2}{4\pi(1+g^2-2g\cos\theta)^{3/2}}.$$

Wavepackets were traced sequentially until they reach the box simulation boundaries (a 10×10×10 cm$^3$ box) or until there energy decreases by a factor 10$^{12}$. The simulation box is divided into cells with 0.1×0.1×0.1 cm$^3$, recording the absorbed energy from every wavepacket. To achieve a reasonable approximation of a realistic system, 10$^8$ wavepackets were launched for every simulation. Light emission process is simulated in the separate code with a wavepacket originating in every simulation cell. The sensor signal is determined as the light intensity reaching the surface of the tissue multiplied by the quantum yield and the excitation intensity of light absorbed by cells where the sensor is implanted. Tissue autofluorescence is determined as the light intensity reaching the surface of the tissue multiplied by the quantum yield taken from the experiment and the excitation intensity of light absorbed by all cells of the tissue except where the sensor is implanted.

Optical measurements. Optical measurements were performed in the reflection configuration. A laser (730 nm, LDX-3430-730 Optronics) was focused using cylindrical and spherical lenses onto the tissue sample with an 800 nm short-pass filter to cut out the laser tail. The laser was controlled by current and temperature modules (Thorlabs, USA). The reflected signal was collected through a dichroic mirror (850 nm long pass) and 1000 nm and 1100 nm long-pass filters using a collimating lens onto a near-infrared photodetector (PDF10C, Thorlabs). Measuring spectral response was used to ensure that no signature of laser reflection present—that is often confused with autofluorescence. A stack of multiple bandpass filters (with typical O.D. of 6-7) was necessary to efficiently filter out signals that are 10-12 orders of magnitude weaker as compared to the incident light. A slanted configuration between filters was introduced to ensure the absence of the cavity effect that would otherwise occur between reflective surfaces, decreasing filtering capabilities. The optical signal was chopped (SR540, Stanford Research Systems) at 100 Hz and the modulated signal was read out by the lock-in amplifier (SR830, Stanford Research Systems). The detector was intensity calibrated, which matched very well with values provided by the supplier (R=1 A/W, gain=$10^8$ kV/A). The detector operated at 500 Hz collection frequency with post-measurement co-adding. For experiments with implants, the sensor signal was calculated as the difference between two measurements from a sample with and without a sensor (background). The background was replicated n=5 times. Typically, a standard variation of 6-10% was observed between background replicas, associated with tissue movement during handling.

To understand the contributions of various noise components, the photodetector behavior (FIGS. 8A-8F) was studied. Upon increasing the illumination power, the photodetector noise increases with the shot noise. Finding the shot noise to reach 5 pW before saturating the detector (t=0.002 sec), the read noise contribution was backed out to be 39 pW. The latter consists of the so-called white and pink components. The application of a lock-in amplifier reduces the read noise, decreasing the pink noise, to the white noise with RMS of 4 pW at 100 Hz. Finally, SNR can also be improved at the expense of the integration time: the signal grows faster than noise as t increases (FIGS. 8A-8F).

To perform wavelength modulation, two lasers were added to the above system: 680 nm, LDX-3230-680, and 780 nm LDX-3215-760, both from Optronics. Mechanical shutters (Thorlabs, USA) were programmed to open in sequential order. Special care was taken to align the excitation paths of three lasers to illuminate the same area on a sample. The incident power on the sample was just below the damage threshold (~300 mW/cm$^2$) with an illumination area of 10 cm$^2$ and fluorescence was collected in the 1100-1300 nm spectral range. In this work, carbon nanotubes' quantum efficiency was estimated to be 1%, the implant typically had 0.01 optical density at 730 nm excitation, while the fluorescent light was collected with 10% efficiency based on the solid angle calculations. In cases when autofluorescence is weak as compared to the signal (specific or thin tissues), the f-component of the signal will be mostly determined by the sensor and not the background. Hence, the technique cannot use f-component as a reference point in this case.

For dyes emitting in the visible range, the excitation was performed using the supercontinuum source and the tunable filter as above. The detection was performed using Si photodetector (APD120A, Thorlabs) that was intensity calibrated. Dye solutions were contained in a chamber made of two glass slides and an o-ring sealed with vacuum grease (~5×5×2 mm$^3$ total volume). Chambers were implanted into phantom tissue. Due to the ratio between the fluorescent intensity and autofluorescence various dyes were implanted at different depths. The following dyes were implanted at 1 cm: TO-PRO-1, Rhodamine 6G, Alexa 700, and eFluor 710. The following dyes were implanted at 1.5 cm: Alexa 750, Alexa 790. The following dyes were implanted at 0.5 cm depth: Alexa 594, BODIPY, and RFP. The Cy3.5 dye was implanted at 0.5 cm depth in the phantom tissue that has reduced chlorophyll content (0.015 mg/l). For dyes implanted at 0.5 cm, SNR at 1 cm was estimated numerically using the respective values measured at 0.5 cm and Monte Carlo simulations. The optical properties of the phantom tissue were matched to those of the brain tissue at the wavelength of excitation, following procedures described above. A needle was inserted through an o-ring to deliver analytes into the chamber. The following dye concentrations were used in 10 µM: TO-PRO-1, Rhodamine 6G, Cy3.5, BODIPY, RFP, Alexa 594, while Alexa 700, Alexa 750, Alexa 790, eFluor 710 were used in 2 µM.

Standoff imaging. The wide field of view imaging setup uses a Princeton Instruments OMA V InGaAs detector to capture a 2D image of an SKH1-E mouse with the hydrogel. The detector is cooled to −100° C. using liquid N$_2$. The detector was affixed with a Nikon AF Micro-Nikkor 60 mm f/2.8D lens to focus the image. A FELH 900 nm long-pass filter (Thorlabs) was placed between the lens and the detector to filter out excitation light. The nanotube embedded hydrogel was excited using a 785 nm Invictus laser with a power density of 20 mW/cm$^2$. The images obtained by this setup were corrected by subtracting the dark current of the detector at the given exposure time. The typical integration time was 1 sec.

Hydrogel preparation. The nanotube embedded hydrogels were prepared using polyethylene glycol diacrylate from Alfa Aesar using a PEG chain length of 8000 Da (PEG8000DA). The UV triggered initiator was 2-hydroxy-4'-(2-hydroxyethoxy)-2-methylpropiophenone from Sigma Aldrich and was dissolved in a stock solution of 7 mg/mL in water before polymerization. The hydrogel precursor solution had a final concentration of polymer 10% (w/v), 20 mg/L SWNT, and 2.5% (v/v) of saturated initiator solution all dissolved in 1×PBS. The hydrogel precursor solution is held under a flowing N$_2$ atmosphere for 30 minutes to remove dissolved oxygen. After degassing, the solution is pipetted into glass molds and returned to the nitrogen atmosphere. The molds are then exposed to 365 nm UV light (UVP Blak-Ray XX-15BLB) for 45 minutes to polymerize. Afterwards, the hydrogels were removed from the molds and left to incubate in 1×PBS overnight to remove any unreacted monomer to free-floating SWNT. Then the PBS solution was exchanged to a fresh solution and the hydrogels were ready to use.

Animal Work. All following procedures performed were approved by the Committee on Animal Care (CAC) and the Division of Comparative Medicine (DCM) at the Massachusetts Institute of Technology. The mice used for this study are SKH1-E mice purchased from Charles River Laboratories. The SKH1-E line is a nude immunocompetent mouse line to simplify the imaging of fluorescent implants. All mice are purchased at 6 weeks old and any mice used in this study are between 8-24 weeks of age. For tissue autofluorescence: mice were sacrificed using $CO_2$ asphyxiation and the tissues of interest were resected. Note that autofluorescence fades away within a couple of hours after animal sacrifice. For in vivo implantations: hydrogels were sterilized before implantation by illumination with UV light for 30 minutes. Either a 10×10 $mm^2$ piece of hydrogel was implanted into the intraperitoneal space through a ventral incision or a 5×5 $mm^2$ piece was implanted subcutaneously. A 2.5" catheter was implanted in the intraperitoneal space through the same incision. The abdominal muscles and skin were closed using sutures. Before the operation, the mouse was anesthetized using 2% isoflurane gas and held under for the remainder of the surgery and the subsequent imaging. Additionally, analgesics were administered before implantation. During imaging, 1 mL of 300 µM riboflavin (or saline for controls) was injected into the intraperitoneal space through the catheter after collecting the fluorescent baseline for 10 minutes. Data was collected for 10 minutes post-injection.

1. Overview of Efforts to Circumvent Signal Attenuation

Historically, a sure way to boost fluorescent signal intensity has been to use stronger excitation power, facilitated by the development of compact lasers across the electromagnetic spectrum. See, for example, M. T. Hill, M. C. Gather, Advances in small lasers, Nature Photonics 8 (2014) 908-918, which is incorporated by reference in its entirety. However living tissue has limitations on allowable incident power, requiring alternative ways to improve the signal to noise ratio. See, for example, I.C.o.N.-I.R. Protection, REVISION OF GUIDELINES ON LIMITS OF EXPOSURE TO LASER RADIATION OF WAVELENGTHS BETWEEN 400 nm AND 1.4 µm, Health Physics 79 (2000) 431-440, which is incorporated by reference in its entirety. This has stimulated research on novel sensors and probes with high quantum yield, but these efforts do not necessarily intersect with high responsivity and specificity, and therefore, do not represent a general solution to these problems. See, for example, J. Yang, Y. Hu, J. Tan, L. Jia, Y.-H. Zhu, J.-S. Yu, Ultra-bright near-infrared-emitting HgS/ZnS core/shell nanocrystals for in vitro and in vivo imaging, Journal of Materials Chemistry B 3 (2015) 6928-6938; and K. Welsher, Z. Liu, S. P. Sherlock, J. T. Robinson, Z. Chen, D. Daranciang, H. Dai, A route to brightly fluorescent carbon nanotubes for near-infrared imaging in mice, Nature Nanotechnology 4 (2009) 773, each of which is incorporated by reference in its entirety. In contrast, improvements in excitation and collection signal efficiency can usually be applied across a wide number of already developed sensors. To this end, besides commercial advances in detector technologies, gain-modulated image-intensified CCD was shown to enhance fluorescent signals. See, for example, A. Godavarty, M. J. Eppstein, C. Zhang, S. Theru, A. B. Thompson, M. Gurfinkel, E. M. Sevick-Muraca, Fluorescence-enhanced optical imaging in large tissue volumes using a gain-modulated ICCD camera, Physics in Medicine and Biology 48 (2003) 1701-1720, which is incorporated by reference in its entirety. From the emission side, wavefront shaping techniques, that rely either on wavefront optical modulators or ultrasound encoders, improve excitation beam focusing inside random media, yet they are typically very slow with continuous measurements still to be demonstrated. See, for example, S. Kang, P. Kang, S. Jeong, Y. Kwon, T. D. Yang, J. H. Hong, M. Kim, K. D. Song, J. H. Park, J. H. Lee, M. J. Kim, K. H. Kim, W. Choi, High-resolution adaptive optical imaging within thick scattering media using closed-loop accumulation of single scattering, Nature Communications 8 (2017) 2157; J. W. Tay, P. Lai, Y. Suzuki, L. V. Wang, Ultrasonically encoded wavefront shaping for focusing into random media, Scientific Reports 4 (2014) 3918; and H. Yu, J. Park, K. Lee, J. Yoon, K. Kim, S. Lee, Y. Park, Recent advances in wavefront shaping techniques for biomedical applications, Current Applied Physics 15 (2015) 632-641, each of which is incorporated by reference in its entirety. To date, one unexplored avenue remains on whether wavelength modulation of the excitation source could aid in detecting signals from the implanted sensor.

2. Analytical Expressions for FFT for Sinusoidal Excitation

The intensity of the fluorescent signal is given by:

$$I_s = \int I(\lambda) \text{Abs}(\lambda) d\lambda \int QY(\lambda) Em(\lambda) d\lambda, \quad (S1)$$

where $I(\lambda)$ is the incident light, $\text{Abs}(\lambda)$ the absorption spectrum of the fluorophore, $QY(\lambda)$ fluorophore quantum yield, and $Em(\lambda)$ its emission spectrum. Throughout this work, signal was collected in the fixed region of interest, while exciting it by lasers with narrow linewidths. Therefore, Eq. S1 can be simplified to $I_s = C\text{Abs}(\lambda)$, where C is a constant.

a. Sensor Signal

Assume the absorption spectrum of the sensor as Lorentzian, $$I_S(\lambda) = A \frac{1}{(\lambda - \lambda_{11})^2 + \gamma^2}, \quad (S2)$$

where A is a constant, $\lambda_{11}$ peak center, $\gamma$ another constant that determines peak linewidth.

Taylor expansion:

$$I_S(\lambda) = A\left(\frac{1}{\gamma^2} - \frac{2}{\gamma^4}\frac{(\lambda-\lambda_{11})^2}{2} + \right. \quad (S3)$$
$$\left. \frac{24}{\gamma^6}\frac{(\lambda-\lambda_{11})^4}{24} - \frac{720}{\gamma^8}\frac{(\lambda-\lambda_{11})^6}{720} + \frac{40320}{\gamma^{10}}\frac{(\lambda-\lambda_{11})^8}{40320} + \cdots\right)$$

$$I_S(\lambda) = A\sum_{i=1}^{\infty}(-1)^{i-1}\left(\frac{1}{\gamma}\right)^{2i}(\lambda-\lambda_{11})^{2i-2}. \quad (S4)$$

For wavelength the sinusoidal modulation was used as the most general case. Indeed, it contains an infinite number of harmonics. As such, sinusoidal modulation can be reduced to any other modulation pattern (assuming it is symmetrical).

Here, one can restrict to the sixth-order expansion, which nicely fits the Lorentzian peak.

$$I_S(\lambda) = \frac{A}{\gamma^2}\left(1 - \frac{(W\sin(2\pi ft))^2}{\gamma^2} + \frac{(W\sin(2\pi ft))^4}{\gamma^4} - \frac{(W\sin(2\pi ft))^6}{\gamma^6} + \right. \quad (S5)$$
$$\left. \frac{(W\sin(2\pi ft))^8}{\gamma^8} - \frac{(W\sin(2\pi ft))^{10}}{\gamma^{10}} + \frac{(W\sin(2\pi ft))^{12}}{\gamma^{12}} - \frac{(W\sin(2\pi ft))^{14}}{\gamma^{14}}\right).$$

FFT becomes:

$$I_S = \frac{A}{\gamma^2}\pi\left[2\delta(y) + \frac{W^2}{\gamma^2}\left(\frac{\delta(y-2)+\delta(y+2)}{2} - \delta(y)\right) + \right.$$
$$\frac{W^4}{\gamma^4}\left(\frac{\delta(y-4)+\delta(y+4)}{8} - \frac{\delta(y-2)+\delta(y+2)}{2} + \frac{3\delta(y)}{4}\right) +$$
$$\frac{W^6}{\gamma^6}\left(\frac{\delta(y-6)+\delta(y+6)}{32} - 3\frac{\delta(y-4)+\delta(y+4)}{16} + \right.$$
$$\left. 15\frac{\delta(y-2)+\delta(y+2)}{32} - \frac{5\delta(y)}{8}\right) +$$
$$\frac{W^8}{\gamma^8}\left(\frac{\delta(y-8)+\delta(y+8)}{128} - \frac{\delta(y-6)+\delta(y+6)}{16} + 7\frac{\delta(y-4)+\delta(y+4)}{32} - \right.$$
$$\left. 7\frac{\delta(y-2)+\delta(y+2)}{16} + \frac{35\delta(y)}{64}\right) + \frac{W^{10}}{\gamma^{10}}\left(\frac{\delta(y-10)+\delta(y+10)}{512} - \right.$$
$$5\frac{\delta(y-8)+\delta(y+8)}{256} + 45\frac{\delta(y-6)+\delta(y+6)}{512} -$$
$$\left. 15\frac{\delta(y-4)+\delta(y+4)}{64} + 105\frac{\delta(y-2)+\delta(y+2)}{256} - \frac{63\delta(y)}{128}\right) +$$
$$\frac{W^{12}}{\gamma^{12}}\left(\frac{\delta(y-12)+\delta(y+12)}{2048} - 3\frac{\delta(y-10)+\delta(y+10)}{512} + \right.$$
$$33\frac{\delta(y-8)+\delta(y+8)}{1024} - 55\frac{\delta(y-6)+\delta(y+6)}{512} +$$
$$\left. 495\frac{\delta(y-4)+\delta(y+4)}{2048} - 99\frac{\delta(y-2)+\delta(y+2)}{256} + \frac{231\delta(Y)}{512}\right) +$$
$$\frac{W^{14}}{\gamma^{14}}\left(\frac{\delta(y-14)+\delta(y+14)}{8192} - 7\frac{\delta(y-12)+\delta(y+12)}{4096} + \right.$$
$$91\frac{\delta(y-10)+\delta(y+10)}{8192} - 91\frac{\delta(y-8)+\delta(y+8)}{2048} +$$
$$1001\frac{\delta(y-6)+\delta(y+6)}{8192} - 1001\frac{\delta(y-4)+\delta(y+4)}{4096} +$$
$$\left.\left. 3003\frac{\delta(y-2)+\delta(y+2)}{8192} - \frac{429\delta(y)}{1024}\right)\right]. \quad (S6)$$

The 2f component can be extracted as:

$$I_s(2f) = \frac{A\pi}{\gamma^2}\left[\frac{W^2}{2\gamma^2} - \frac{W^4}{2\gamma^4} + \frac{15W^6}{32\gamma^6} - \frac{7W^8}{16\gamma^8} + \frac{105W^{10}}{256\gamma^{10}} - \frac{99W^{12}}{256\gamma^{12}} + \frac{3003W^{14}}{8192\gamma^{14}}\right]. \quad (S7)$$

Note if the wavelength modulation is not performed around $\lambda_{11}$, the expression becomes even more complex. The modulation can be written as $\lambda=\lambda_{11}+W\sin(2\pi ft)+C$.

$$I_s(\lambda) = \frac{A}{\gamma^2} \quad (S8)$$
$$\left(1 - \frac{(W\sin(2\pi ft)+C)^2}{\gamma^2} + \frac{(W\sin(2\pi ft)+C)^4}{\gamma^4} - \frac{(W\sin(2\pi ft)+C)^6}{\gamma^6} + \right.$$
$$\frac{(W\sin(2\pi ft)+C)^8}{\gamma^8} - \frac{(W\sin(2\pi ft)+C)^{10}}{\gamma^{10}} +$$
$$\left. \frac{(W\sin(2\pi ft)+C)^{12}}{\gamma^{12}} - \frac{(W\sin(2\pi ft)+C)^{14}}{\gamma^{14}}\right)$$

The expression after FFT is quite bulky, so only the 2f component of it is provided:

$$I_s(2f) = \quad (S9)$$
$$\frac{A\pi}{\gamma^2}\left[\left(\frac{W^2}{2\gamma^2} - \frac{W^4}{2\gamma^4} + \frac{15W^6}{32\gamma^6} - \frac{7W^8}{16\gamma^8} + \frac{105W^{10}}{256\gamma^{10}} - \frac{99W^{12}}{256\gamma^{12}} + \frac{3003W^{14}}{8192\gamma^{14}}\right) + \right.$$
$$\frac{C^2}{W^2}\left(-\frac{3W^4}{\gamma^4} + \frac{15W^6}{2\gamma^6} - \frac{105W^8}{8\gamma^8} + \frac{315W^{10}}{16\gamma^{10}} - \frac{3465W^{12}}{128\gamma^{12}} + \frac{9009W^{14}}{256\gamma^{14}}\right) +$$
$$\frac{C^4}{W^4}\left(\frac{15W^6}{2\gamma^6} - \frac{35W^8}{\gamma^8} + \frac{1575W^{10}}{16\gamma^{10}} - \frac{3465W^{12}}{16\gamma^{12}} + \frac{105105W^{14}}{256\gamma^{14}}\right) +$$
$$\frac{C^6}{W^6}\left(-\frac{14W^8}{\gamma^8} + \frac{105W^{10}}{\gamma^{10}} - \frac{3465W^{12}}{8\gamma^{12}} + \frac{21021W^{14}}{16\gamma^{14}}\right) +$$
$$\frac{C^8}{W^8}\left(\frac{45W^{10}}{2\gamma^{10}} - \frac{495W^{12}}{2\gamma^{12}} + \frac{45045W^{14}}{32\gamma^{14}}\right) +$$
$$\left. \frac{C^{10}}{W^{10}}\left(-\frac{33W^{12}}{\gamma^{12}} + \frac{1001W^{14}}{2\gamma^{14}}\right) + \frac{C^{12}}{W^{12}}\frac{91W^{14}}{2\gamma^{14}}\right].$$

Notice that expression falls into Eq. (S7) when C=0.

b. Background Signal $$I_b(\lambda) = B\exp[-\alpha(\lambda-\lambda_0)], \quad (S10)$$

where B and $\alpha$ are constants, and $\lambda_0$ is the absorption peak center of the background signal. Taylor expansion gives:

$$I_b(\lambda) = B\sum_{i=0}^{\infty}\left(-\frac{\alpha(\lambda-\lambda_0)}{i!}\right)^i \approx \quad (S11)$$
$$B\left(1 - \alpha(\lambda-\lambda_0) + \frac{\alpha^2(\lambda-\lambda_0)^2}{2!} - \frac{\alpha^3(\lambda-\lambda_0)^3}{3!} + \frac{\alpha^4(\lambda-\lambda_0)^4}{4!} - \right.$$
$$\left. \frac{\alpha^5(\lambda-\lambda_0)^5}{5!} + \frac{\alpha^6(\lambda-\lambda_0)^6}{6!} - \frac{\alpha^7(\lambda-\lambda_0)^7}{7!} + \frac{\alpha^8(\lambda-\lambda_0)^8}{8!}\right).$$

At least eight orders are necessary to fit the original signal across the modulation region. Wavelength modulation takes the form of $\lambda=\lambda_{11}+W\sin(2\pi ft)$, yielding:

$$I_b(f) = B\pi\left[\alpha W - \alpha^2(\lambda_{11}-\lambda_0)W + \right. \quad (S12)$$
$$\alpha^3\frac{\frac{3W^3}{4} + 3W(\lambda_{11}-\lambda_0)^2}{6} - \alpha^4\frac{3(\lambda_{11}-\lambda_0)W^3 + 4W(\lambda_{11}-\lambda_0)^3}{24} +$$
$$\alpha^5\frac{\frac{5W^5}{8} + \frac{15W^3(\lambda_{11}-\lambda_0)^2}{2} + 5W(\lambda_{11}-\lambda_0)^4}{120} -$$
$$\alpha^6\frac{15W^3(\lambda_{11}-\lambda_0)^3 + \frac{15W^5(\lambda_{11}-\lambda_0)}{4} + 6W(\lambda_{11}-\lambda_0)^5}{720} +$$
$$\alpha^7\frac{\frac{35W^7}{64} + \frac{105W^5(\lambda_{11}-\lambda_0)^2}{8} + \frac{105W^3(\lambda_{11}-\lambda_0)^4}{4} + 7W(\lambda_{11}-\lambda_0)^6}{5040} -$$

$$I_b(2f) = B\pi\left[-\frac{\alpha^2 W^2}{4} + \alpha^3 \frac{W^2(\lambda_{11}-\lambda_0)}{4} - \alpha^4 \frac{\frac{W^4}{2}+3W^2(\lambda_{11}-\lambda_0)^2}{24} + \alpha^5 \frac{\frac{5W^4(\lambda_{11}-\lambda_0)}{2}+5W^2(\lambda_{11}-\lambda_0)^3}{120} - \alpha^6 \frac{\frac{15W^6}{32}+\frac{15W^4(\lambda_{11}-\lambda_0)^2}{2}+\frac{15W^2(\lambda_{11}-\lambda_0)^4}{2}}{720} + \alpha^7 \frac{\frac{105W^6(\lambda_{11}-\lambda_0)}{32}+\frac{35W^4(\lambda_{11}-\lambda_0)^3}{2}+\frac{21W^2(\lambda_{11}-\lambda_0)^5}{2}}{5040} - \alpha^8 \frac{\frac{7W^8}{16}+\frac{105W^6(\lambda_{11}-\lambda_0)^2}{8}+\frac{35W^4(\lambda_{11}-\lambda_0)^4+14W^2(\lambda_{11}-\lambda_0)^6}{2}}{40320}\right]$$

$$\left.\alpha^8 \frac{\frac{35W^5(\lambda_{11}-\lambda_0)^3+42W^3(\lambda_{11}-\lambda_0)^5+\frac{35W^7(\lambda_{11}-\lambda_0)}{8}+8W(\lambda_{11}-\lambda_0)^7}}{(40320)}\right]. \quad (S13)$$

Notice the G-factor, $I_b(2f)/I_b(f)$, does not depend on the intensity, but is only determined by the spectral parameter $\alpha$ (and hence animal model) and modulation parameter W. The G factor is simply a mathematical construct for referencing, not unique to WIFF. To account for the offset modulation, one needs to substitute $\lambda_{11}$ to $\lambda_{11}+C$ in Eqs. (S12, S13).

3. Analytical Expressions for FFT for Step-Wise Excitation

Three-laser excitation allows straightforwardly finding Fourier components. For the signal modulated around the absorption peak of the sensor, the peak value is: $I_s(\lambda_{11})=A/\gamma^2$ and the sidebands are $I_s(\lambda_{11}-W)=I_s(\lambda_{11}+W)=A/(W^2+\gamma^2)$. Then 2f-component can be found as:

$$I_s(2f) = \frac{A}{2\gamma^2} - \frac{A}{2(W^2+\gamma^2)}. \quad (S14)$$

Eq. S14 matches well the measurements presented in FIG. 2h.

Similarly, for off-center modulation:

$$I_s(2f) = \frac{A}{C^2+\gamma^2} - \frac{1}{4}\left(\frac{A}{(C+W)^2+\gamma^2} + \frac{A}{(C-W)^2+\gamma^2} + \frac{2A}{C^2+\gamma^2}\right). \quad (S15)$$

By putting the derivative $$\frac{\partial I_s(2f)}{\partial C}$$

equal to 0, one can find the condition for maxima and minima:

$$\frac{2C}{(C^2+\gamma^2)^2} - \frac{C+W}{((C+W)^2+\gamma^2)^2} - \frac{C-W}{((C-W)^2+\gamma^2)^2} = 0. \quad (S16)$$

There is no analytical solution for all the roots, but certain solutions can be found. In particular, when assuming $C^2 \gg \gamma^2$, which is reasonable for broad peaks of fluorescent sensors, one can see that C=0 is the solution, confirming that $I_s(2f)$ reaches a maximum at C=0. Furthermore, C=W is also a solution, corresponding to the first minimum. Eq. S16 matches very well the measurements presented in FIG. 2I.

4. Extracting Analyte Concentration from Sensor Response

The normalized intensity changes in calibration curves of sensors are fit by a cooperative equilibrium model:

$$\frac{\Delta I}{I_0} = a\frac{C^n}{C^n+K_D^n}, \quad (S17)$$

where n is a cooperativity coefficient, a is a proportionality constant to convert concentration to fluorescence, $K_D$ is the dissociation constant, and C is the concentration of an analyte in contact with sensors. The fitted parameters for the solution phase calibration curves are shown in Table S1.

The interaction between an analyte and the hydrogel sensor is further described with analyte diffusion. The mathematical model solves the following nondimensionalized unsteady diffusion model and boundary conditions:

$$\frac{\partial C}{\partial t} = D\frac{\partial^2 C}{\partial x^2} \quad (S18)$$

$$C(0, x) = 0$$

$$C(t, 0) = C_0$$

$$\frac{dC}{dx}(t, L) = 0$$

where x is a dimension of length, t is time, D is the effective diffusivity in the hydrogel, $C_0$ is the concentration boundary layer at the top of the gel, and L is the thickness of the gel where the no flux condition is maintained. The system of equations is nondimensionalized as follows:

$$\theta = \frac{C}{C_0}, X = \frac{x}{L}, \tau = \frac{t}{L^2/D} \quad (S19)$$

$$\frac{\partial \theta}{\partial \tau} = D\frac{\partial^2 \theta}{\partial X^2}$$

$$\theta(0, X) = 0$$

$$\theta(\tau, 0) = 1$$

$$\frac{d\theta}{dX}(\tau, 1) = 0$$

where $\tau$ is dimensionless time, X is a dimensionless distance, and $\theta$ is dimensionless concentration. The solution to this dimensionless system of equations is shown below:

$$\theta(X, \tau) = 1 - \sum_{n=0}^{\infty} \frac{2}{\lambda_n} e^{-\lambda_n^2 \tau} \sin(\lambda_n \tau) \quad \text{(S20)}$$

$$\lambda_n = (n + 0.5)\pi, \, n = 0, 1, 2, \ldots$$

The analyte is assumed to have fast kinetics with the sensor such that the sensor and the analyte are in equilibrium at all time points. Eq. S17 and S20 were used to fit intensity data to extract diffusion constants. The $K_D$ was allowed to vary due to the hydrogel potentially changing the corona phase and altering the equilibrium. The proportionality constant, a, was allowed to vary due to the data being collected over the entire emission range with an integrated fluorescent signal, instead of the 1D spectra as was in solution. The extracted parameters and the fit uncertainties were used to calculate actual analyte concentrations.

5. Understanding the Deep Tissue Detection Limit

The background is one of the factors that cause the depth limitation in optical sensing. To understand the deep tissue detection limits, consider what determines sensor and background signals. In an optically dense medium (FIG. 1C), the external excitation power ($P_0$) at wavelength $\lambda_{exc}$ reaching the sensor can be approximated to decay exponentially with depth (d):

$$P_{sensor} \approx (1-R)P_0 e^{-\mu(\lambda_{exc})d}, \quad \text{(S21)}$$

according to a wavelength-dependent extinction coefficient $\mu(\lambda_{exc})$. To account for light diffusion, $\mu$ takes a form of a function of scattering and absorption coefficients $\mu = f(\mu_{abs}, \mu_{sca})$. See, for example, A. N. Bashkatov, E. A. Genina, V. I. Kochubey, V. V. Tuchin, Optical properties of human skin, subcutaneous and mucous tissues in the wavelength range from 400 to 2000 nm, Journal of Physics D: Applied Physics 38 (2005) 2543-2555, which is incorporated by reference in its entirety. The excitation power $P_0$ cannot be increased above the damage threshold of biological tissue, typically of 300 mW/cm$^2$. See, for example, I.C.o.N.-I.R. Protection, REVISION OF GUIDELINES ON LIMITS OF EXPOSURE TO LASER RADIATION OF WAVELENGTHS BETWEEN 400 nm AND 1.4 µm, Health Physics 79 (2000) 431-440, which is incorporated by reference in its entirety. Similarly, decreasing the surface reflectivity at the air-tissue interface (R) only provides a linear advantage compared to the exponential signal decay. Excited at power $P_{sensor}$, the sensor fluorescence at wavelength $\lambda_{em}$ must travel back through the same media with extinction $\mu(\lambda_{em})$. In contrast to the excitation source, which can be collimated on the surface of a sample, the fluorescence is emitted isotropically from the sample surface. Thus, only a small fraction of the emitted signal can be detected ($P_s$), based on the relative solid angle of the detector:

$$P_s \approx P_{sensor} \cdot QY \cdot \Omega \cdot A e^{-\mu(\lambda_{em})d}, \quad \text{(S22)}$$

where a signal at the power $P_s$ must be detected, after accounting for the probe or sensor quantum yield (QY), the solid angle of the detector from the surface of a sample ($\Omega$), and absorbance (A). A common approach in biomedical optics is to use near-infrared probes because the scattering and absorption contributions to u are significantly reduced. See, for example, G. Hong, A. L. Antaris, H. Dai, Near-infrared fluorophores for biomedical imaging, Nature Biomedical Engineering 1 (2017) 0010, which is incorporated by reference in its entirety.

Several studies point to tissue autofluorescence as the dominant background signal, even in the near-infrared. See, for example, K. Welsher, Z. Liu, S. P. Sherlock, J. T. Robinson, Z. Chen, D. Daranciang, H. Dai, A route to brightly fluorescent carbon nanotubes for near-infrared imaging in mice, Nature Nanotechnology 4 (2009) 773; B. del Rosal, I. Villa, D. Jaque, F. Sanz-Rodríguez, In vivo autofluorescence in the biological windows: the role of pigmentation, Journal of Biophotonics 9 (2016) 1059-1067; and S. Diao, G. Hong, A. L. Antaris, J. L. Blackburn, K. Cheng, Z. Cheng, H. Dai, Biological imaging without autofluorescence in the second near-infrared region, Nano Research 8 (2015) 3027-3034, each of which is incorporated by reference in its entirety. Furthermore, the spectral properties of autofluorescence remain minimally studied, especially in the near-infrared. See, for example, A. M. Degrand, S. J. Lomnes, D. S. Lee, M. Pietrzykowski, S. Ohnishi, T. Morgan, A. Gogbashian, R. G. Laurence, J. V. Frangioni, Tissue-like phantoms for near-infrared fluorescence imaging system assessment and the training of surgeons, SPIE2006, which is incorporated by reference in its entirety. In fact, $P_s$ itself does not determine the limit but rather the signal-to-noise ratio (SNR):

$$SNR = \frac{\text{Signal}}{\text{Noise}} = \frac{P_s t}{\sqrt{P_s t + P_b t + P_{dark} t + N_{read}^2}}. \quad \text{(S23)}$$

Here, successful signal detection can be successful when SNR is greater than 3, as commonly assumed for chemical sensors. See, for example, H.-P. Loock, P. D. Wentzell, Detection limits of chemical sensors: Applications and misapplications, Sensors and Actuators B: Chemical 173 (2012) 157-163, which is incorporated by reference in its entirety. The scattered excitation light and tissue autofluorescence ($P_b$) as well as the signal received by the detector in the absence of any light ($P_{dark}$), both contribute to the shot noise, lowering SNR (FIG. S21). There are limits to the effectiveness of increased integration time (t) to overcome the instrument read noise, $N_{read}^2$. See, for example, P. J. Fish, Intrinsic Noise, in: P. J. Fish (Ed.), Electronic Noise and Low Noise Design, Macmillan Education UK, London, 1993, pp. 72-90, which is incorporated by reference in its entirety.

TABLE 1

Sensor parameters extracted from calibration curves for sensors in solution.

| Corona | Analyte | Cooperativity constant, n | Proportionality constant, a | Dissociation constant, $K_D$ (µM) |
|---|---|---|---|---|
| (ACCA)$_7$ | Ascorbic acid | 0.58 | 1.20 | 0.58 |
| (AC)$_{15}$ | Riboflavin | 0.66 | −0.99 | 0.40 |
| (GT)$_{15}$ | H$_2$O$_2$ | 0.77 | −0.84 | 85.2 |

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed is:

1. A system for monitoring a sensor, comprising:
   an excitation source directing a modulated excitation beam at an implanted sensor, the modulated excitation beam having a modulation frequency whereby a fluorescence excitation wavelength is modulated across an absorption cross-section of a target probe allowing the emission signal to be separated from the autofluorescent background; and
   a detector configured to monitor emission from the sensor, wherein the detector monitors emission at a multiple of the modulation frequency.

2. The system of claim 1, wherein the modulated excitation beam includes three distinct excitation wavelengths.

3. The system of claim 1, wherein the modulated excitation beam includes a first wavelength at or near a peak absorbance of the sensor and a second wavelength that is 20 nm to 60 nm shorter than the first wavelength.

4. The system of claim 3, wherein the modulated excitation beam further includes a third wavelength that is 20 nm to 60 nm longer than the first wavelength.

5. The system of claim 1, wherein the modulation frequency is less than 50 Hz, less than 40 Hz, less than 30 Hz, less than 20 Hz, less than 10 Hz, less than 5 Hz, less than 4 Hz, less than 3 Hz, less than 2 Hz, or less than 1 Hz.

6. The system of claim 1, wherein the detector evaluates a frequency that is 2, 3, 4, 5, 6, 7 or 8 times the modulation frequency.

7. The system of claim 1, wherein the detector monitors emission at a wavelength greater than 1000 nm.

8. The system of claim 1, wherein the excitation source is a continuum laser or a plurality of single wavelength lasers.

9. The system of claim 1, wherein the detector includes a band-pass filter.

10. The system of claim 1, wherein the sensor includes an emissive element.

11. The system of claim 10, wherein the emissive element is a fluorescent dye, a semiconductor nanocrystal or a carbon nanotube.

12. The system of claim 1, wherein the sensor includes a photoluminescent nanostructure embedded in a sensor hydrogel and an analyte-binding compound associated with the photoluminescent nanostructure.

13. The system of claim 12, wherein the analyte-binding compound includes a polymer.

14. A method of detecting an emission from a sensor, comprising:
    irradiating a sensor with a modulated excitation beam having a modulation frequency whereby a fluorescence excitation wavelength is modulated across an absorption cross-section of a target probe allowing the emission signal to be separated from the autofluorescent background; and
    detecting an emission from the sensor, wherein the detector monitors emission at a multiple of the modulation frequency.

15. The method of claim 14, wherein the modulated excitation beam includes three distinct excitation wavelengths.

16. The method of claim 14, wherein the modulated excitation beam includes a first wavelength at or near a peak absorbance of the sensor and a second wavelength that is 20 nm to 60 nm shorter than the first wavelength.

17. The method of claim 16, wherein the modulated excitation beam further includes a third wavelength that is 20 nm to 60 nm longer than the first wavelength.

18. The method of claim 14, wherein the modulation frequency is less than 50 Hz, less than 40 Hz, less than 30 Hz, less than 20 Hz, less than 10 Hz, less than 5 Hz, less than 4 Hz, less than 3 Hz, less than 2 Hz, or less than 1 Hz.

19. The method of claim 14, wherein the detector evaluates a frequency that is 2, 3, 4, 5, 6, 7 or 8 times the modulation frequency.

20. The method of claim 14, wherein the detector monitors emission at a wavelength greater than 1000 nm.

21. The method of claim 14, wherein the excitation source is a continuum laser or a plurality of single wavelength lasers.

22. The method of claim 14, wherein the detector includes a band-pass filter.

23. The method of claim 14, wherein the sensor includes an emissive element.

24. The method of claim 23, wherein the emissive element is a fluorescent dye, a semiconductor nanocrystal or a carbon nanotube.

25. The method of claim 14, wherein the sensor includes a photoluminescent nanostructure embedded in a sensor hydrogel and an analyte-binding compound associated with the photoluminescent nanostructure.

26. The method of claim 25, wherein the analyte-binding compound includes a polymer.

27. The method of claim 14, further comprising detecting photoluminescence from the sensor.

28. The method of claim 14, wherein the sensor is in tissue.

29. The method of claim 28, wherein the sensor is more than 3 cm beneath a surface of the tissue.

30. The method of claim 28, wherein the sensor is more than 5 cm beneath a surface of the tissue.

31. The method of claim 14, further comprising improving a signal to noise ratio compared to a single excitation source by a factor of at least 30.

* * * * *